(12) United States Patent
Hanna et al.

(10) Patent No.: US 8,486,927 B2
(45) Date of Patent: Jul. 16, 2013

(54) CRYSTALLINE FORMS OF LAMOTRIGINE

(75) Inventors: Mazen Hanna, Bradford (GB); Ning Shan, Tampa, FL (US); Miranda L. Cheney, Tampa, FL (US)

(73) Assignee: Thar Pharmaceuticals, Pittsburgh, PA (US)

( * ) Notice: Subject to any disclaimer, the term of this patent is extended or adjusted under 35 U.S.C. 154(b) by 475 days.

(21) Appl. No.: 12/291,517

(22) Filed: Nov. 10, 2008

(65) Prior Publication Data

US 2009/0176787 A1    Jul. 9, 2009

Related U.S. Application Data

(60) Provisional application No. 61/002,594, filed on Nov. 9, 2007.

(51) Int. Cl.
*A01N 43/00*    (2006.01)
*A61K 31/33*    (2006.01)

(52) U.S. Cl.
USPC .......................... 514/183; 514/242; 544/182

(58) Field of Classification Search
USPC .................................. 514/183, 242; 544/182
See application file for complete search history.

(56) References Cited

U.S. PATENT DOCUMENTS

| | | |
|---|---|---|
| 4,602,017 A | 7/1986 | Sawyer et al. |
| 4,847,249 A | 7/1989 | Sawyer et al. |
| 5,912,345 A | 6/1999 | Winter et al. |
| 5,925,755 A | 7/1999 | Lee |
| 5,942,510 A | 8/1999 | Floyd et al. |
| 6,111,101 A | 8/2000 | Vyas |
| 6,333,198 B1 | 12/2001 | Edmeades et al. |
| 2005/0032799 A1 | 2/2005 | Buxton et al. |
| 2005/0119265 A1 | 6/2005 | Parthasaradhi et al. |
| 2005/0171107 A1 | 8/2005 | Garti et al. |
| 2006/0003002 A1 | 1/2006 | Fikstad et al. |
| 2008/0139808 A1 | 6/2008 | Garti et al. |

FOREIGN PATENT DOCUMENTS

| | | |
|---|---|---|
| EP | 0 247 892 | 12/1987 |
| WO | WO 96/20935 | 7/1996 |
| WO | WO 01/49669 | 7/2001 |
| WO | WO 02/068398 | 9/2002 |

OTHER PUBLICATIONS

Sridhar, B. and K. Ravikumar, "Lamotriginium benzoate dimethylformamide solvate," Acta Cryst. E61:3805-3807 (2005).
Kubicki, M. and P.W. Codding, "Hydrogen bonding patterns in 3,5-diamino-6-aryl triazines," J. Mol. Struc. 570:53-60 (2001).

*Primary Examiner* — Brandon Fetterolf
*Assistant Examiner* — Jean Cornet
(74) *Attorney, Agent, or Firm* — Rakoczy Molino Mazzochi Siwik LLP

(57) ABSTRACT

The invention is directed to novel crystalline forms of lamotrigine. These novel crystalline forms of lamotrigine have improved dissolution and in-vivo absorption profile, as compared to pure lamotrigine. These novel crystalline forms of lamotrigine provide a substantial increase in the blood concentration of lamotrigine, as compared to pure lamotrigine when administered to a subject. These novel crystalline forms of lamotrigine also provide a slower, steady build up of lamotrigine blood concentration suitable for sustained release of lamotrigine in-vivo, as compared to pure lamotrigine.

14 Claims, 33 Drawing Sheets

CRYSTALLINE FORMS OF LAMOTRIGINE

CROSS-REFERENCE TO RELATED APPLICATIONS

The application claims the benefit under 35 U.S.C. §1.119 (e) of U.S. provisional application No. 61/002,594, filed Nov. 9, 2007, and incorporated herein by reference in its entirety.

FIELD OF THE INVENTION

The invention pertains to new forms of lamotrigine, which include lamotrigine co-crystals, salts, hydrous forms, solvates, hydrates and solvates of salts, mixtures thereof, as well as methods for their preparation and pharmaceutical compositions that include one or more of these new forms. These new forms of lamotrigine have an improved in-vivo absorption profile, as compared to pure lamotrigine, and thus can provide either a sustained release of lamotrigine, as compared to pure lamotrigine, or a substantial increase in blood concentration of lamotrigine, as compared to pure lamotrigine.

BACKGROUND OF THE INVENTION

Lamotrigine is known as 6-(2,3-dichlorophenyl)-1,2,4-triazine-3,5-diamine or 3,5-diamino-6-(2,3-dichlorophenyl)-1,2,4-triazine. The molecular formula of lamotrigine is $C_9H_7N_5Cl_2$, and its molecular weight is 256.09 g/mol. Lamotrigine is depicted by the following chemical structure:

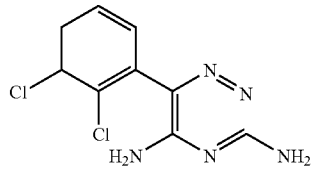 [SMILES: N=N/C(C1=C(Cl)C(Cl)CC=C1)=C(N)\N=C\N]

Lamotrigine is the active ingredient in Lamictal® marketed by GlaxoSmithKline. It is an anti-convulsant drug of the phenyltriazine class used in the treatment of epilepsy as well as in the treatment of psychiatric disorders such as bipolar disorder. Lamotrigine is indicated for the adjunctive treatment of partial and primary generalized tonic-clonic seizures and generalized seizures associated with Lennox-Gastaud syndrome. Lamotrigine is indicated for conversion to monotherapy in adults with partial seizures who are receiving treatment with anti-epileptic drugs carbamazepine, phenyloin, phenobarbital, primidone or valproate. Lamotrigine also acts as a mood stabilizer. Lamotrigine is also useful for the treatment of neuropathic pain, cluster headaches, migraines and affective disorders.

Lamotrigine is available as a compressed tablet and as a chewable dispersible tablet for oral administration. The chewable dispersible tablets can be swallowed, chewed, or dispersed in a small amount of liquid to form slurry. This formulation was developed to facilitate administration to mainly people with swallowing difficulties such as children and elderly patients.

The peak plasma concentrations of the existing marketed tablet occur anywhere from 1.4 to 4.8 hours following drug administration. One disadvantage of this is that the plasma concentration (pharmacokinetic profile (PK)) achieved with conventional tablets is cyclical, with relatively high peaks occurring after administration followed by low troughs occurring before the next administration of drug.

In particular for the treatment of epilepsy it is thought that too-low troughs in the peak plasma concentration may lead to breakthrough seizures, result in some adverse events (AE) occurring in some patients. Alternatively, a too-rapid rate of increase in plasma concentration in the initial stages before the peak plasma concentration is achieved may also affect the AE profile.

Until recently, it was not known where, in the gastrointestinal tract, lamotrigine is absorbed (U.S. Appl. Publ. No. 2005/0032799). In carrying out a regional absorption study it has recently been discovered that the extent of absorption of lamotrigine is consistent when the drug is delivered to any point in the gastrointestinal tract between the stomach and the ascending colon. The extent of absorption is similar whether the drug is delivered as a solid or as a solution.

Preparation of Lamotrigine and its Therapeutic Uses are Disclosed in U.S. Pat. No. 4,602,017.

Different synthetic methods of lamotrigine are described in WO 01/049669, U.S. Pat. Nos. 6,111,101, 6,333,198, 5,912,345, and EP 800521.

Lamotrigine is a white to pale cream-colored powder and has a $pK_a$ of 5.7. Lamotrigine is very slightly soluble in water (0.17 mg/mL at 25° C.) and slightly soluble in 0.1 M HCl (4.1 mg/mL at 25° C.).

Lamotrigine benzoate dimethylformamide solvate (Sridhar et al., Acta Cryst. (2005) E61, o-3805) and lamotrigine hydrogen phthalate dimethylformamide solvate (Sridhar et al., Mol. Cryst. Liq. Cryst. (2007) 461, 131) have been reported.

Various patents and references have attempted to solve use limitations caused by lamotrigine's poor solubility. See, e.g., U.S. Appl. Publ. No. 2005/0119265; Kubicki and Codding (J. Mol. Struct. (2001) 570, 53; WO 02/068398; EP 0,247,892; U.S. Pat. Nos. 5,912,345; 5,925,755; 4,847,249; and 5,942,510. In general, these approaches have involved different crystal forms, different salt forms, or reducing particle size. Some formulation approaches in the foregoing, particularly those involving certain salt forms, are undesirable for particular uses, such as parenteral, owing to their inherent lack of stability or acidity.

Because of the limitations related to the low aqueous solubility of lamotrigine, there is a need to develop novel forms of lamotrigine that have improved physico-chemical properties including aqueous solubility, which can be formulated for use in various delivery routes, including parenteral and oral administration.

BRIEF SUMMARY OF THE INVENTION

The present invention is directed towards generating new crystalline forms of larnotrigine. One aspect of the present invention includes novel water soluble molecular complexes of lamotrigine that includes co-crystals, salts, and solvates (e.g. hydrates and mixed solvates as well as solvates of salts), and mixtures containing such materials. In addition, the invention further includes methods for the preparation of such complexes. The invention further includes compositions suitable for pharmaceutical use and/or dosage forms containing the molecular complexes of lamotrigine. Specific molecular complexes pertaining to the disclosure include, but are not limited to, co-crystals of methylparaben, and nicotinamide. Specific salts pertaining to the disclosure include, but are not limited to, larnotrigine saccharinate, lamotrigine adipate and lamotrigine malate. Specific solvates pertaining to the disclosure include, but are not limited to, methanol solvate of lamotrigine nicotinate, lamotrigine methanolate form II, lamotrigine ethanolate hydrate, and lamotrigine hydrate form II.

The invention also includes the herein described crystalline forms that possess some adsorbed substances, such as water or solvent, within a portion of the crystal or sample. Obvious variants of the disclosed lamotrigine forms in the text, including those described by the drawings and examples, and processes for preparing them, will be readily apparent to the person of ordinary skill in the art having the present disclosure, and such variants are considered to be a part of the current invention.

According to one aspect of the invention, a crystalline form of lamotrigine is provided which when administered to a subject provides an in-vivo absorption profile with a substantial increase in blood concentration of lamotrigine as compared to pure lamotrigine.

According to another aspect of the invention, crystalline forms of lamotrigine selected from the group consisting of co-crystal lamotrigine:methylparaben form I, co-crystal lamotrigine:methylparaben form II, co-crystal lamotrigine:nicotinamide, salts of lamotrigine saccharinate, lamotrigine adipate, lamotrigine malate, methanol solvate of lamotrigine nicotinate salt, dimethanol solvate, ethanolate hydrate and hydrate of lamotrigine, are provided.

According to yet another aspect of the invention, there is provided a crystalline form of lamotrigine which is co-crystal lamotrigine:methylparaben form I which: a) has a PXRD diffraction pattern with peaks at about 7.19, 14.4, 16.7, 17.9, 20.75, 26.56, and 32.02+/−0.2 degrees two-theta; and/or b) has a PXRD diffraction pattern substantially as depicted in FIG. 1.

According to another aspect of the invention, there is provided a crystalline form of lamotrigine which is co-crystal lamotrigine:methylparaben form II which: a) has a PXRD diffraction pattern with peaks at about 15.53, 18.89, 20.74, 22.0, 23.08, 23.95 and 26.89+/−0.2 degrees two-theta; b) has a PXRD diffraction pattern substantially as depicted in FIG. 3; and/or c) is characterized by a DSC thermogram with an endothermic peak at about 162.4° C.

The invention also provides a crystalline form of lamotrigine wherein said crystalline form is co-crystal lamotrigine:nicotinamide which: a) has a PXRD diffraction pattern with peaks at about 7.79, 14.96, 17.18, 18.98, 23.21, 26.72 and 27.47+/−0.2 degrees two-theta; b) has a PXRD diffraction pattern substantially as depicted in FIG. 7; and/or c) is characterized by a DSC thermogram with an endothermic peak at about 167.2° C.

Yet another aspect of the invention is directed to a crystalline form of lamotrigine wherein said crystalline form is lamotrigine saccharinate which: a) has a PXRD diffraction pattern with peaks at about 5.19, 13.61, 14.96, 15.26, 24.10, 27.34 and 28.42+/−0.2 degrees two-theta; b) has a PXRD diffraction pattern substantially as depicted in FIG. 10; and/or c) is characterized by a DSC thermogram with an endothermic peak at about 262.56° C.

Another aspect of the invention is a crystalline form of lamotrigine which is lamotrigine adipate which: a) has a PXRD diffraction pattern with peaks at about 6.81, 18.09, 21.17, 22.81, 23.90, 25.56, and 28.20+/−0.2 degrees two-theta; and/or b) has a PXRD diffraction pattern substantially as depicted in FIG. 14.

A further aspect of the invention is a crystalline form of lamotrigine which is lamotrigine malate which: a) has a PXRD diffraction pattern with peaks at about 12.89, 19.49, 20.77, 21.76, 24.70, 26.44 and 29.47+/−0.2 degrees two-theta; and/or b) has a PXRD diffraction pattern substantially as depicted in FIG. 17.

The invention also provides a crystalline form of lamotrigine which is lamotrigine nicotinate methanolate which: a) has a PXRD diffraction pattern with peaks at about 11.54, 11.90, 16.65, 21.07, 21.85, 22.99 and 27.43+/−0.2 degrees two-theta; and/or b) has a PXRD diffraction pattern substantially as depicted in FIG. 20.

Another aspect of the invention is a crystalline form of lamotrigine which is lamotrigine dimethanolate which: a) has a PXRD diffraction pattern with peaks at about 9.17, 14.66, 15.65, 16.52, 19.99, 28.36 and 30.19+/−0.2 degrees two-theta; and/or b) has a PXRD diffraction pattern substantially as depicted in FIG. 23.

Yet a further aspect of the invention is a crystalline form of lamotrigine which is lamotrigine ethanolate hydrate which: a) has a PXRD diffraction pattern with peaks at about 11.21, 12.44, 20.37, 24.02, 26.07, 26.47, and 27.55+/−0.2 degrees two-theta; and/or b) has a PXRD diffraction pattern substantially as depicted in FIG. 26.

The present invention also provides a crystalline form of lamotrigine which is lamotrigine hydrate which: a) has a PXRD diffraction pattern with peaks at about 13.28, 15.95, 20.59, 23.53, 26.65, 28.27 and 30.76+/−0.2 degrees two-theta; b) has a PXRD diffraction pattern substantially as depicted in FIG. 29; and/or c) is characterized by a DSC thermogram with an endothermic peak at about 218.25° C.

Another aspect of the present invention is a pharmaceutical composition comprising an effective amount of one or more of the crystalline forms of lamotrigine disclosed herein and a pharmaceutically acceptable excipient.

Yet another aspect of the present invention is a crystalline form of lamotrigine which when administered to a subject provides an improved in-vivo absorption profile with a sustained release of lamotrigine as compared to pure lamotrigine.

The foregoing and other features and advantages of the disclosed technology will become more apparent from the following detailed description, which proceeds with reference to the accompanying drawings. Such description is meant to be illustrative, and not limiting, of the invention.

DETAILED DESCRIPTION OF THE INVENTION

Figure 1:
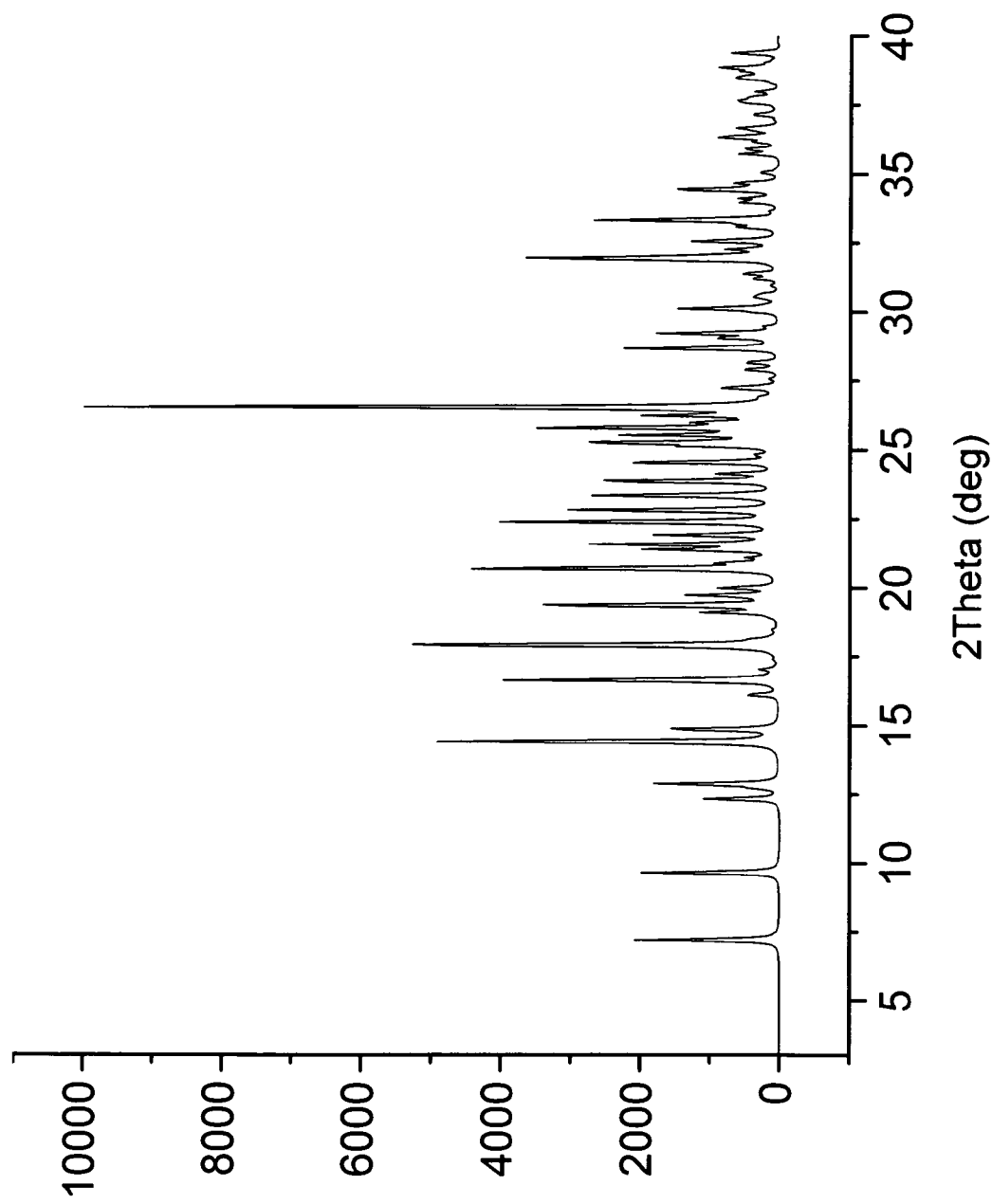
FIG. 1—Calculated PXRD diffractogram of a co-crystal comprising lamotrigine and methylparaben (Form I).
Figure 2:
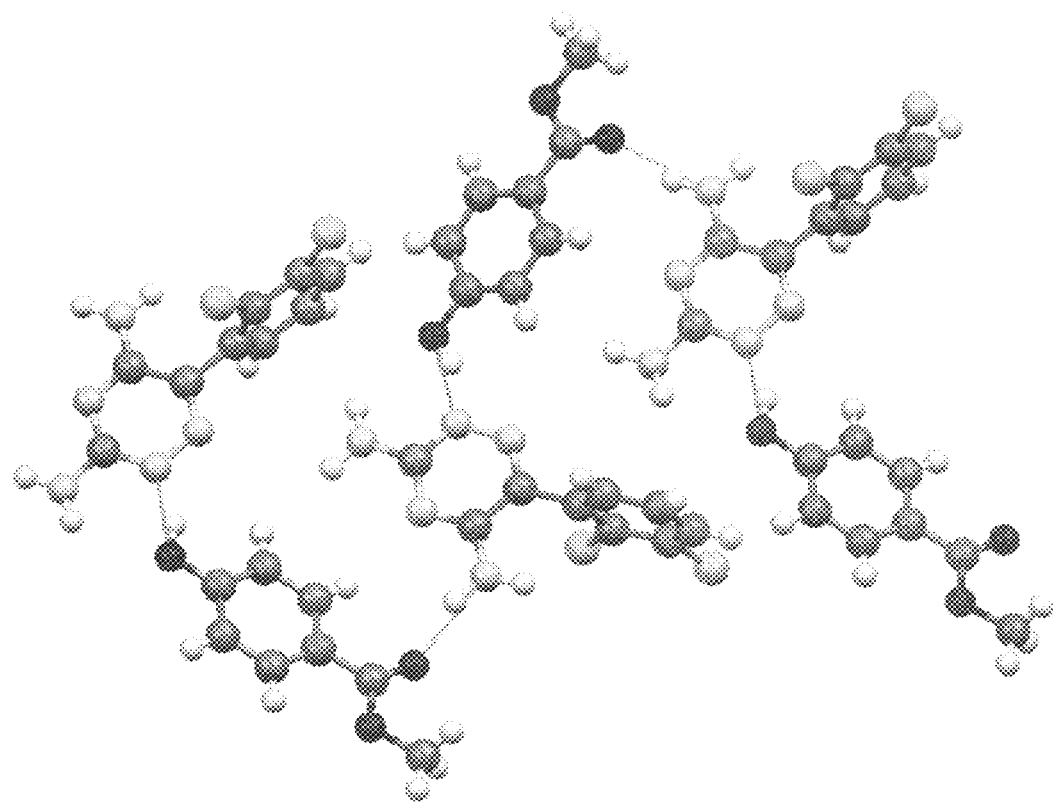
FIG. 2—Packing diagram for lamotrigine:methylparaben co-crystal (Form I).

In general, active pharmaceutical compounds in pharmaceutical compositions can be prepared in a variety of different forms. Such compounds can be prepared so as to have a variety of different chemical forms including chemical derivatives, solvates, hydrates, co-crystals and/or salts. Such compounds can also be prepared to have different physical forms. For example, they may be amorphous, may have different crystalline polymorphs, or may exist in different solvation or hydration states. The discovery of new crystalline forms of a pharmaceutically useful compound may provide an opportunity to improve the performance characteristics of a pharmaceutical product. Additionally it expands the array of resources available for designing, for example, a pharmaceutical dosage form of a drug with a targeted release profile or other desired characteristics.

A specific characteristic that can be targeted includes the crystal form of an active pharmaceutical compound. By altering the crystal form it therefore becomes possible to vary the physical properties of the target molecule. For example, crystalline polymorphs typically have different aqueous solubility from one another, such that a more thermodynamically stable polymorph is less soluble than a less thermodynamically stable polymorph. In addition to water solubility, pharmaceutical polymorphs can also differ in properties such as shelf-life, bioavailability, morphology, vapor pressure, density, color, and compressibility. Accordingly, it is desirable to improve the properties of an active pharmaceutical compound by forming molecular complexes such as a co-crystal, a salt, a solvate or a hydrate with respect to solubility, rate of dissolution, bioavailabilty, stability, $C_{max}$, $T_{max}$, down stream processibility (including compressibility, flowability and ease of particle size manipulation), hygroscopicity, crystallization of amorphous compounds, decrease in polymorphic form diversity, toxicity, taste, production costs, and manufacturing methods.

For oral delivery, it is frequently advantageous to have novel crystalline forms of drugs that possess improved properties, including increased aqueous solubility and stability. It is also desirable in general to increase the dissolution rate of such forms, increase bioavailability, and provide a more rapid onset to quicken the therapeutic effect. It is also useful to have a crystal form of lamotrigine which, when administered to a subject, reaches a peak plasma level faster and has a longer lasting therapeutic plasma concentration, when compared to other forms on a dose-for-dose basis.

By "crystalline forms" of lamotrigine it is meant co-crystals, salts, solvates and hydrates of lamotrigine. The crystalline forms of lamotrigine of the present disclosure can give rise to improved properties of lamotrigine. For example, a new crystal form of lamotrigine is particularly advantageous if it can improve the aqueous solubility of lamotrigine. Additionally, the crystal properties conferred upon the new crystal forms of lamotrigine are also useful when the bioavailability of lamotrigine is improved and its plasma concentration and/or serum concentration improved. This is particularly advantageous for orally delivered lamotrigine formulations. A number of novel lamotrigine crystalline forms have been synthesized, characterized, and disclosed herein. The techniques and approaches set forth in the present disclosure can further be used by the person of ordinary skill in the art to prepare obvious variants thereof, said variants considered to be part of the inventive disclosure.

Lamotrigine form I, supplied by Jai Radhe Sales, India with purity of 99.79% was used without further purification for all experiments as the starting material to produce the co-crystal forms described in this disclosure. All other analytical grade chemicals were supplied by Sigma-Aldrich and used without further purification.

Several techniques have been used to observe the crystalline forms, as later described. The particular methodology used in such analytical techniques should be viewed as illustrative, and not limiting in the context of data collection. For example, the particular instrumentation used to collect data may vary; routine operator error or calibration standards may vary; sample preparation method may vary (for example, the use of the KBr disk or Nujol mull technique for IR analysis). For the single crystal analysis in particular, depending on the nature and size of the crystal; degree of crystal perfectness; software program used; refinement method selected; temperature of data collection; and other variables inherent in single crystal x-ray diffraction analysis, replicate crystal structure attempts may lead to differences between the data reported in the present disclosure (such as that involving space group, atomic bond distances, and the like) and later results. Such variations are routinely encountered, without indicating a material change in the nature of the overall crystal form, and thus forms exhibiting such variances should be deemed to be a part of the present invention.

Furthermore, for PXRD, the intensity of the peaks can differ from sample to sample, due to, among other things, orientation effects. In some crystal habits certain orientations are preferred which enhance some diffraction peaks and reduce others. We describe below as "major" or "strongest" peaks the largest peaks in the samples we measured. However, these peaks may not be the largest peaks in some samples or preparations due to the orientation effects. The peak positions, on the other hand, are largely unaffected by orientation effects. Furthermore, while we have provided the relative locations of the peaks, these locations can differ by up to +/−0.5 degrees two-theta, preferably by up to +/−0.2 degrees two-theta, depending on how the X-ray powder diffraction machine is calibrated.

Single Crystal X-Ray Diffraction (Single Crystal XRD):

Suitable single crystals were selected and analyzed for x-ray analysis. Data was collected on a Bruker-AXS SMART APEX CCD diffractometer with monochromatized Mo KR radiation ($\lambda$=0.71073 Å). Data was collected at 100 K. Lattice parameters were determined from least-squares analysis, and reflection data were integrated using the program SAINT. Structures were solved by direct methods and refined by full matrix least squares based on F2 using SHELXTL. All non-hydrogen atoms were refined with anisotropic displacement parameters.

Powder X-Ray Diffraction (PXRD):

Lamotringe:methylparaben co-crystal form II, lamotrigine:nicotinamide co-crystal, lamotringine saccharinate, and lamotrigine hydrate form II were observed by a D-8 Bruker X-ray Powder Diffraction using Cu K$\alpha$ ($\lambda$=1.540562 Å), 50 kV, 40 mA. The data was collected over an angular range of 3° to 40° 2$\theta$ in continuous scan mode using a step size of 0.01° 2$\theta$ and a scan speed of 1.0°/min.

Calculated PXRD:

Calculated PXRD diffractograms were generated from the single crystal structures using Mercury 1.5 (Cambridge Crystallographic Data Centre, UK) for the following complexes: lamotrigine:methylparaben form I, lamotrigine adipate, lamotrigine malate, lamotrigine nicotinate methanolate, lamotrgine dimethanolate, and lamotrigine ethanolate hydrate.

Differential Scanning Calorimetry (DSC):

Differential Scanning Calorimetry was performed on a Perkin Elmer Diamond DSC.

Fourier Transform Infrared Spectroscopy (FTIR):

IR analysis was performed on a Perkin Elmer Spectrum 100 FT-IR spectrometer equipped with a solid-state ATR accessory.

Ultraviolet-Visible Spectroscopy (UV/Vis):

UV/Vis analysis was performed on a Perkin Elmer Lambda 25 UV/Vis spectrometer.

Accordingly, in a first aspect, the present invention includes co-crystals of lamotrigine and methylparaben (forms I and II), such that the lamotrigine and methylparaben are capable of co-crystallizing from a solution phase under crystallization conditions or from the solid-state, for example, through grinding or heating.

Co-crystals of lamotrigine and methylparaben have been observed by their x-ray single crystal structures, x-ray powder diffraction patterns, differential scanning calorimetry curves and/or infra-red absorption spectra.

The co-crystal of lamotrigine and methylparaben form I has been evaluated by the single crystal x-ray diffraction data as shown in Example 1.

The co-crystal of lamotrigine and methylparaben form I has been evaluated by a calculated PXRD diffractogram shown in FIG. 1.

The co-crystal of lamotrigine and methylparaben form II has been evaluated by the single crystal x-ray diffraction data as shown in Example 3.

Figure 3:
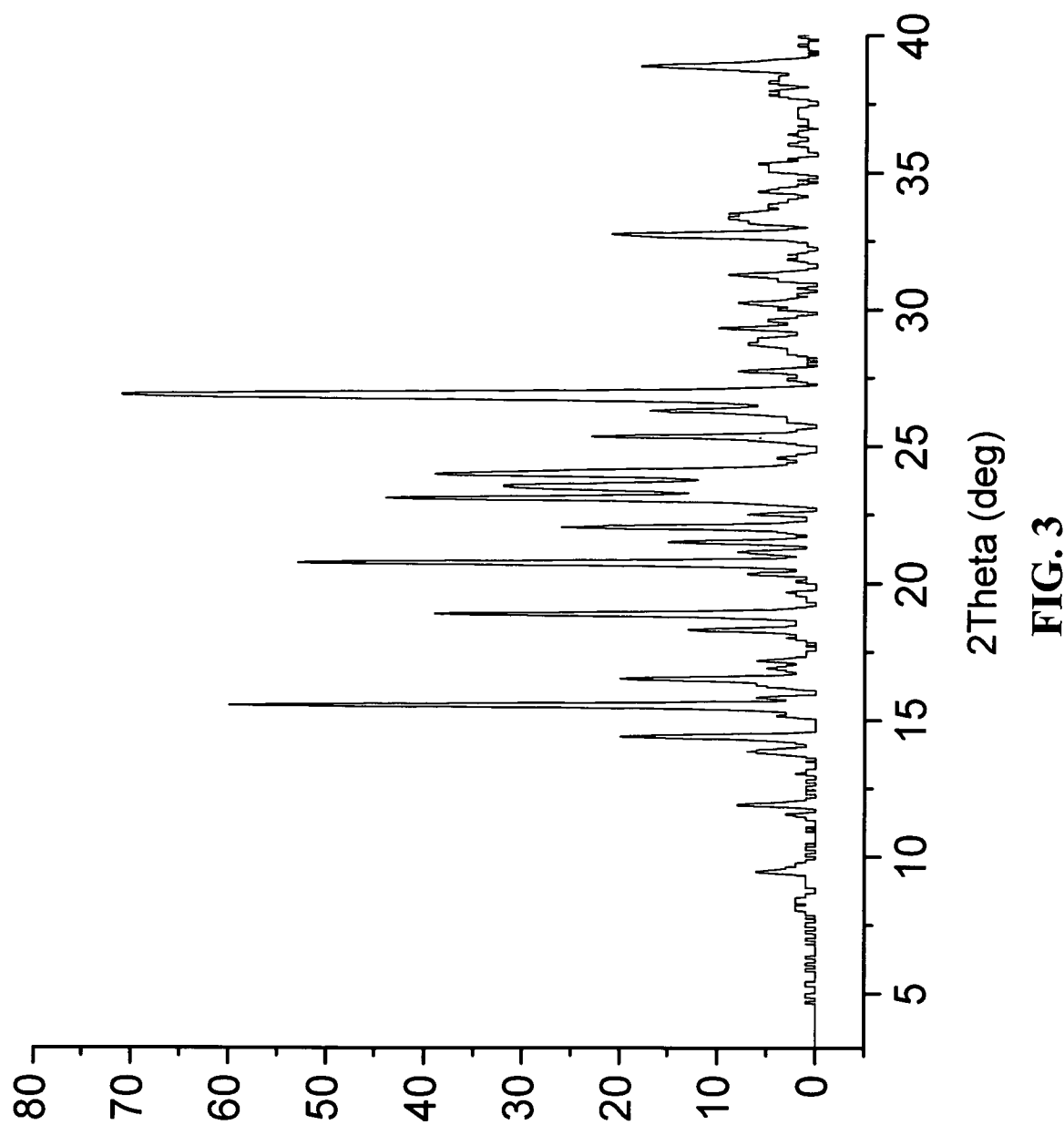
FIG. 3—PXRD diffractogram of a co-crystal comprising lamotrigine and methylparaben (Form II).

The co-crystal of lamotrigine and methylparaben form II has been evaluated by a PXRD diffractogram shown in FIG. 3.

Figure 4:
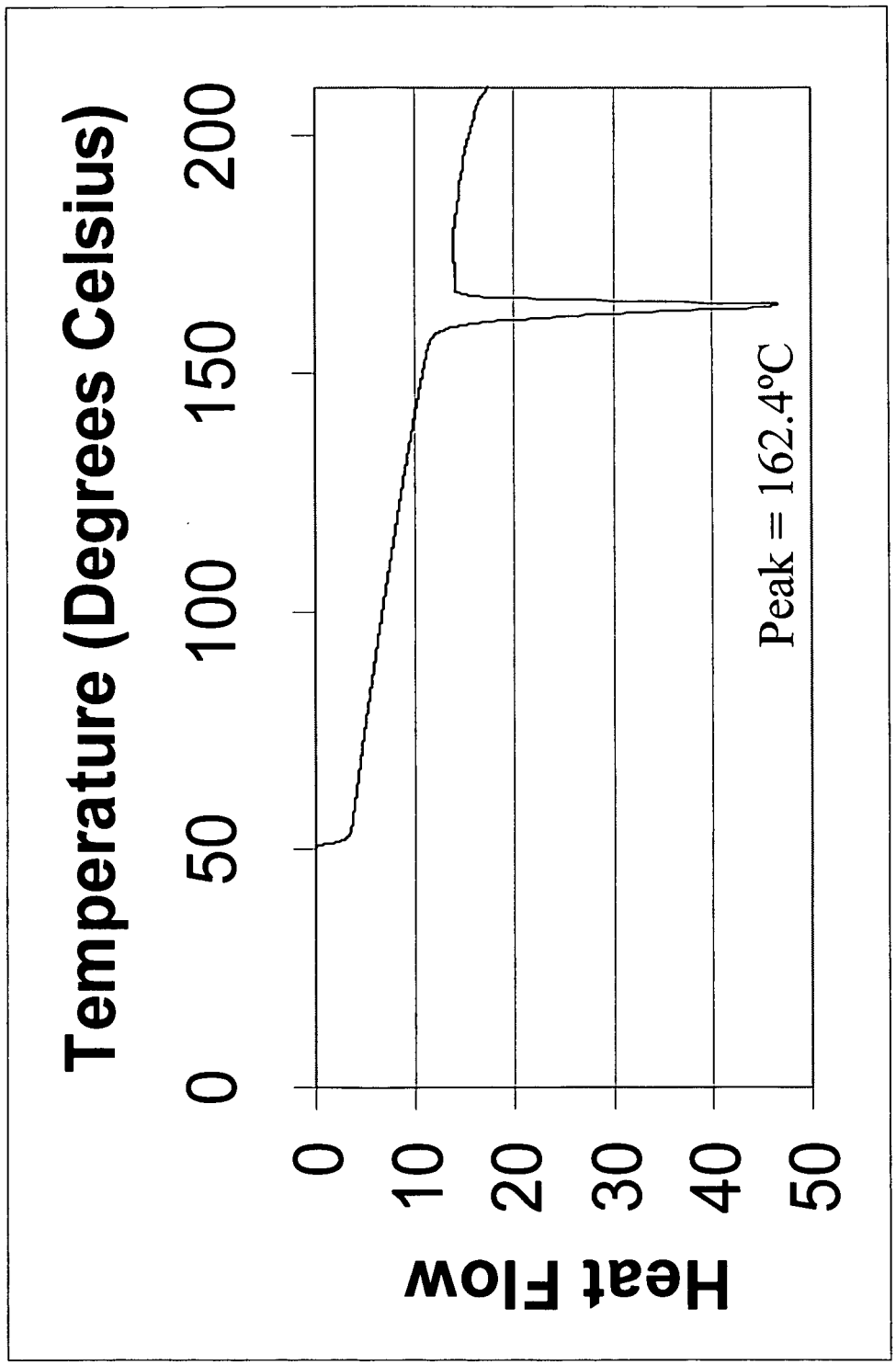
FIG. 4—DSC thermogram of a co-crystal comprising lamotrigine and methylparaben (Form II).

The co-crystal of lamotrigine and methylparaben form II has been evaluated by a DSC phase transition shown in FIG. 4.

Figure 5:
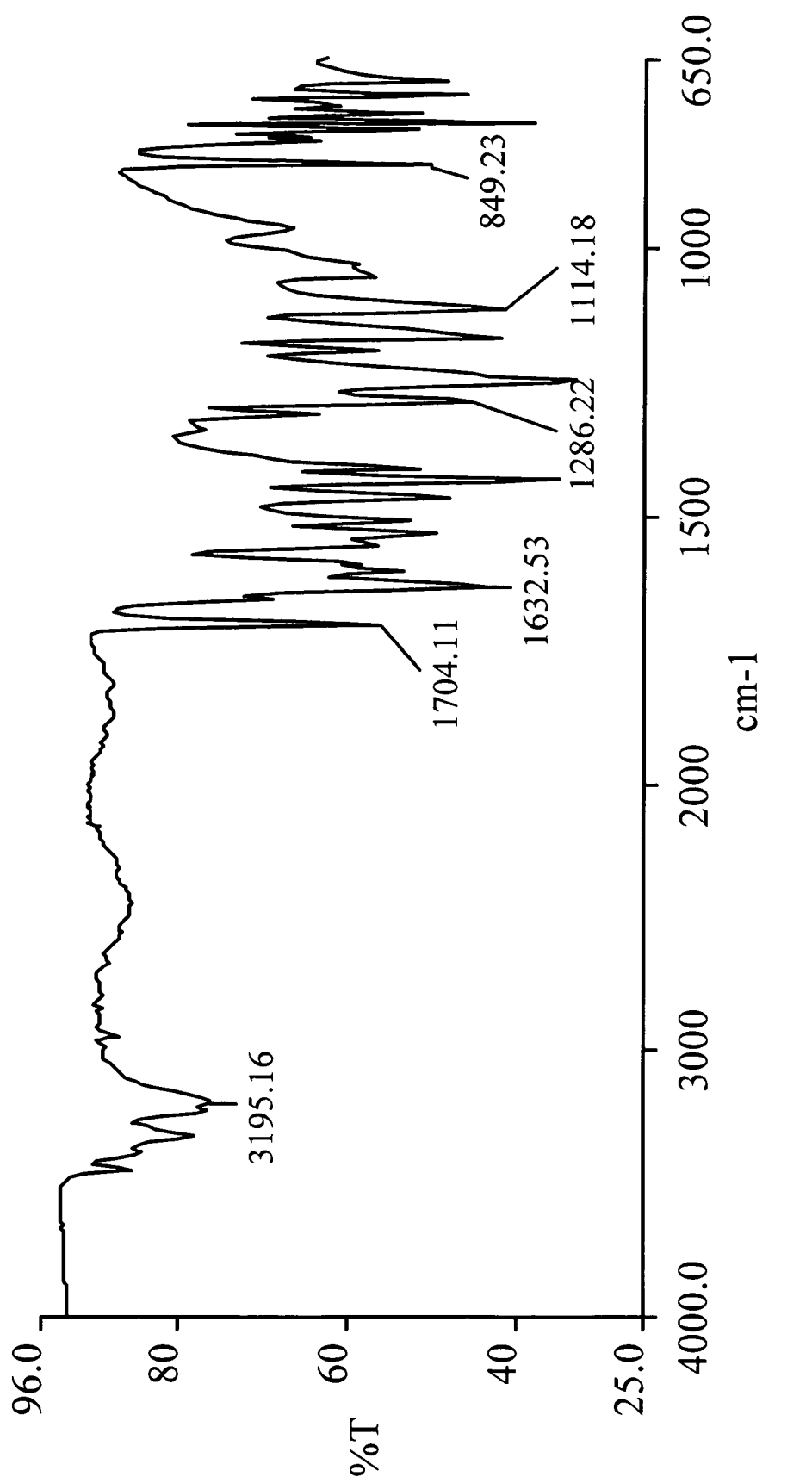
FIG. 5—Infrared spectrum of a co-crystal comprising lamotrigine and methylparaben (Form II).
Figure 6:
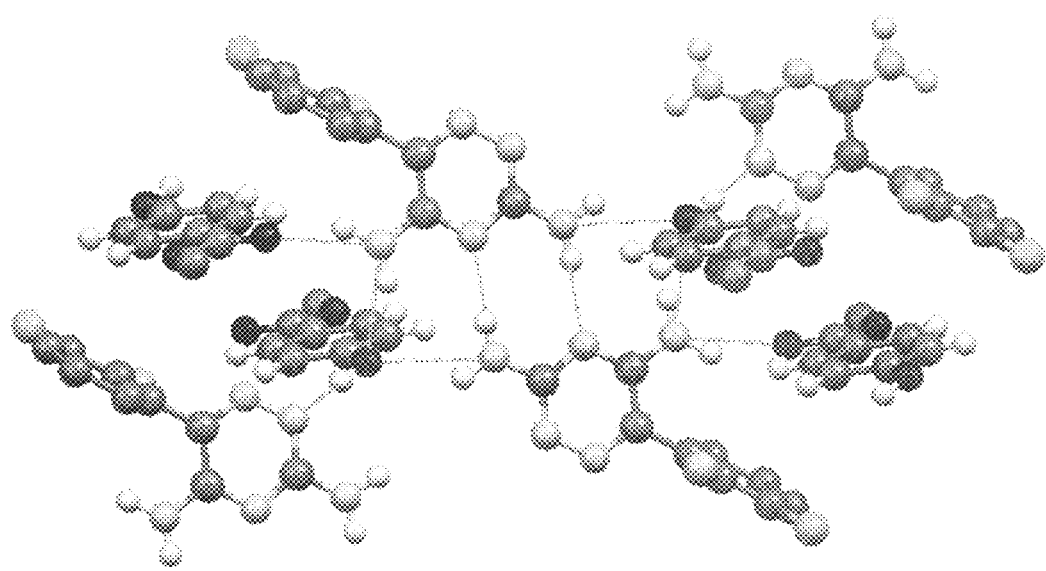
FIG. 6—Packing diagram for lamotrigine:methylparaben co-crystal (Form II).

The co-crystal of lamotrigine and methylparaben form II has been evaluated by an FT-IR spectrum pattern as shown substantially in FIG. 5.

Another aspect of the present invention provides a co-crystal of lamotrigine and nicotinamide, such that the lamotrigine and nicotinamide are capable of co-crystallizing from, for example, a solution phase under crystallization conditions; or from the solid-state, for example, through grinding or heating.

Co-crystals of lamotrigine and nicotinamide have been evaluated by x-ray powder diffraction, differential scanning calorimetry and infra-red absorption.

Figure 7:
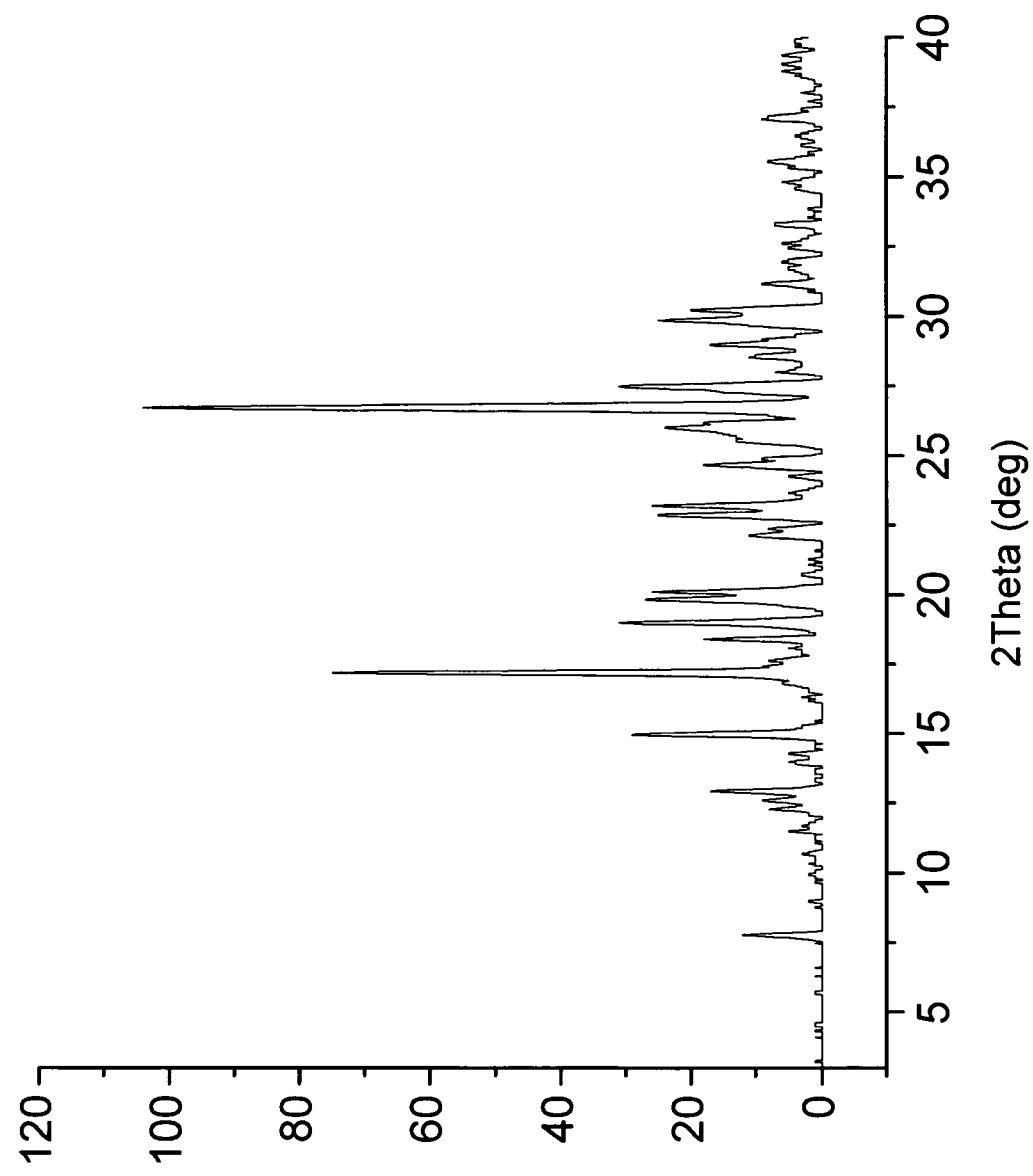
FIG. 7—PXRD diffractogram of a co-crystal comprising lamotrigine and nicotinamide.

The co-crystal of lamotrigine and nicotinamide has been evaluated by a PXRD diffractogram shown in FIG. 7.

Figure 8:
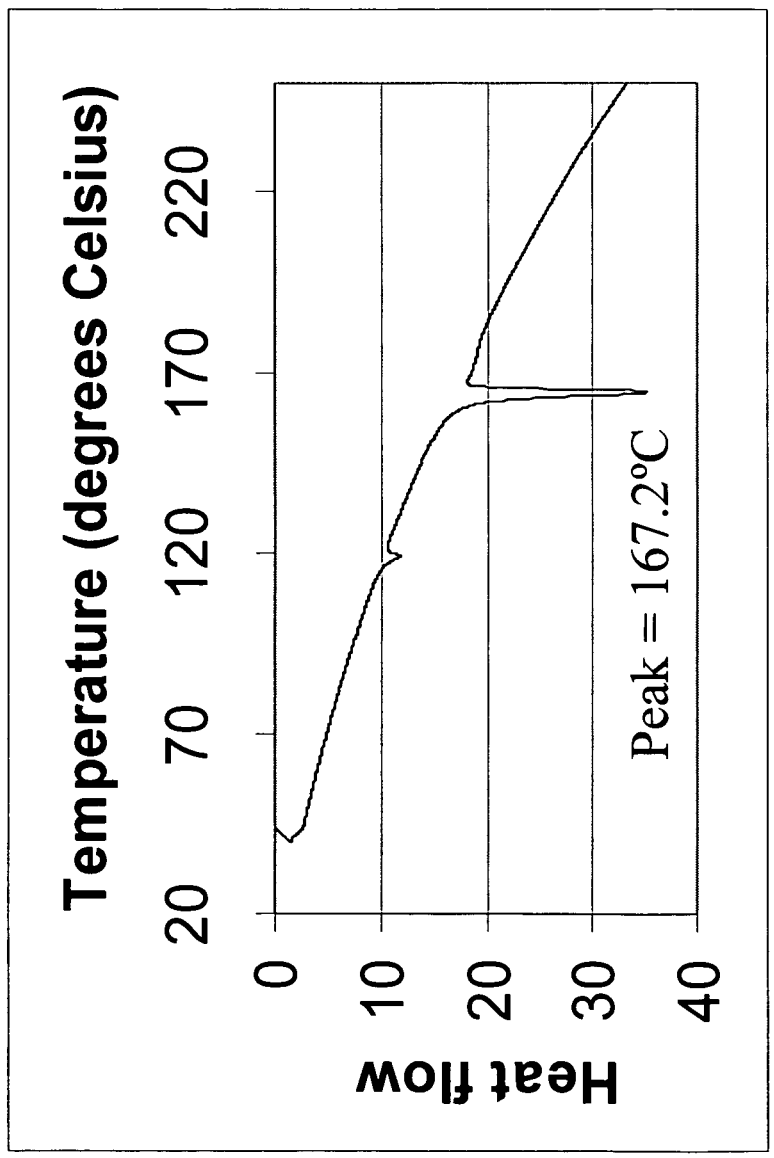
FIG. 8—DSC thermogram of a co-crystal comprising lamotrigine and nicotinamide.

The co-crystal of lamotrigine and nicotinamide is identified by a DSC phase transition shown in FIG. 8.

Figure 9:
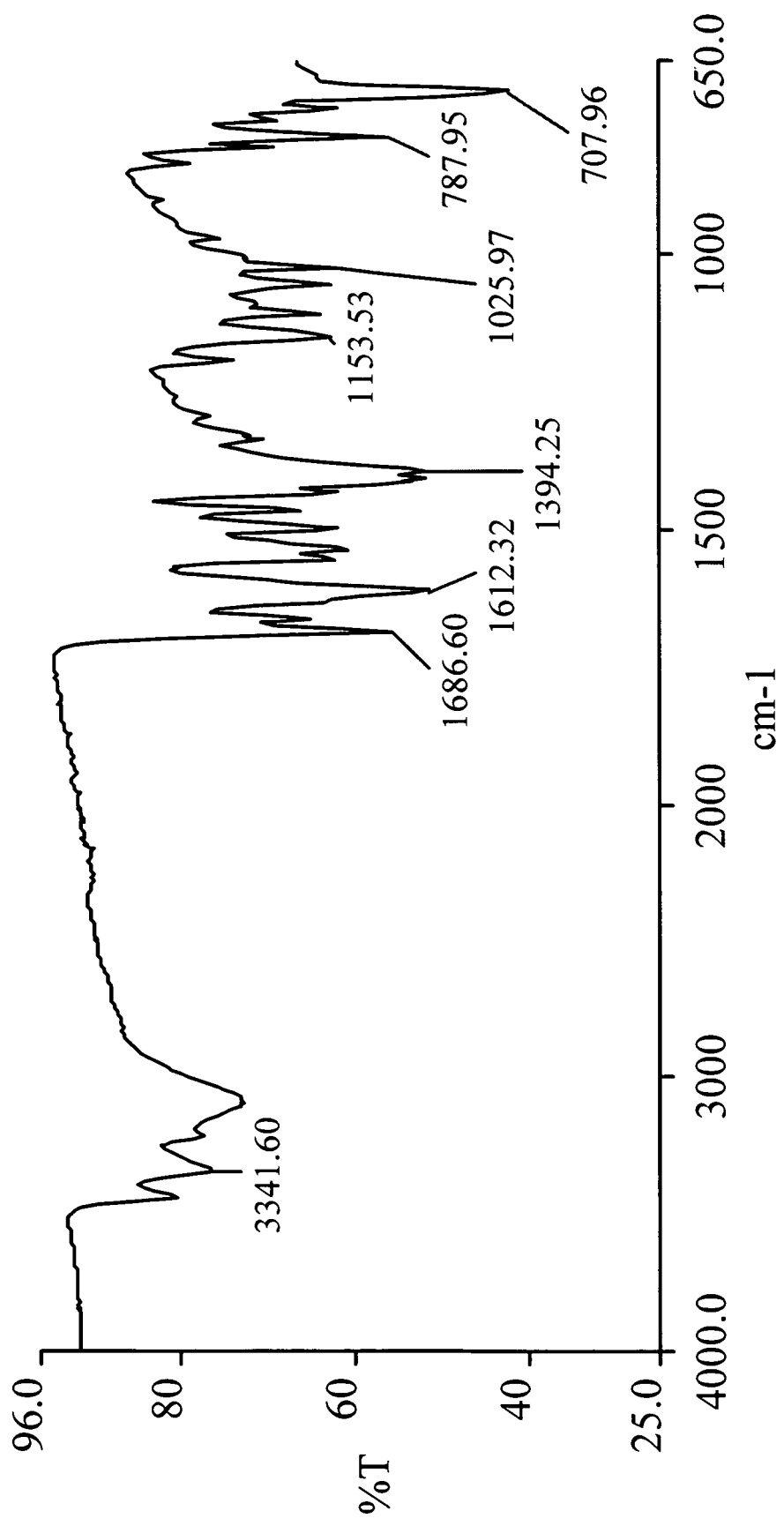
FIG. 9—Infrared spectrum of a co-crystal comprising lamotrigine and nicotinamide.

The co-crystal of lamotrigine and nicotinamide is identified by an FT-IR spectrum pattern as shown substantially in FIG. 9.

Another aspect of the present invention provides a salt comprising lamotrigine and saccharin, which has been evaluated by its x-ray single crystal structure, x-ray powder diffraction pattern, differential scanning calorimetry curve and infra-red absorption spectrum.

More specifically, crystalline lamotrigine saccharinate has been evaluated by the single crystal x-ray diffraction data as shown in Example 7.

Figure 10:
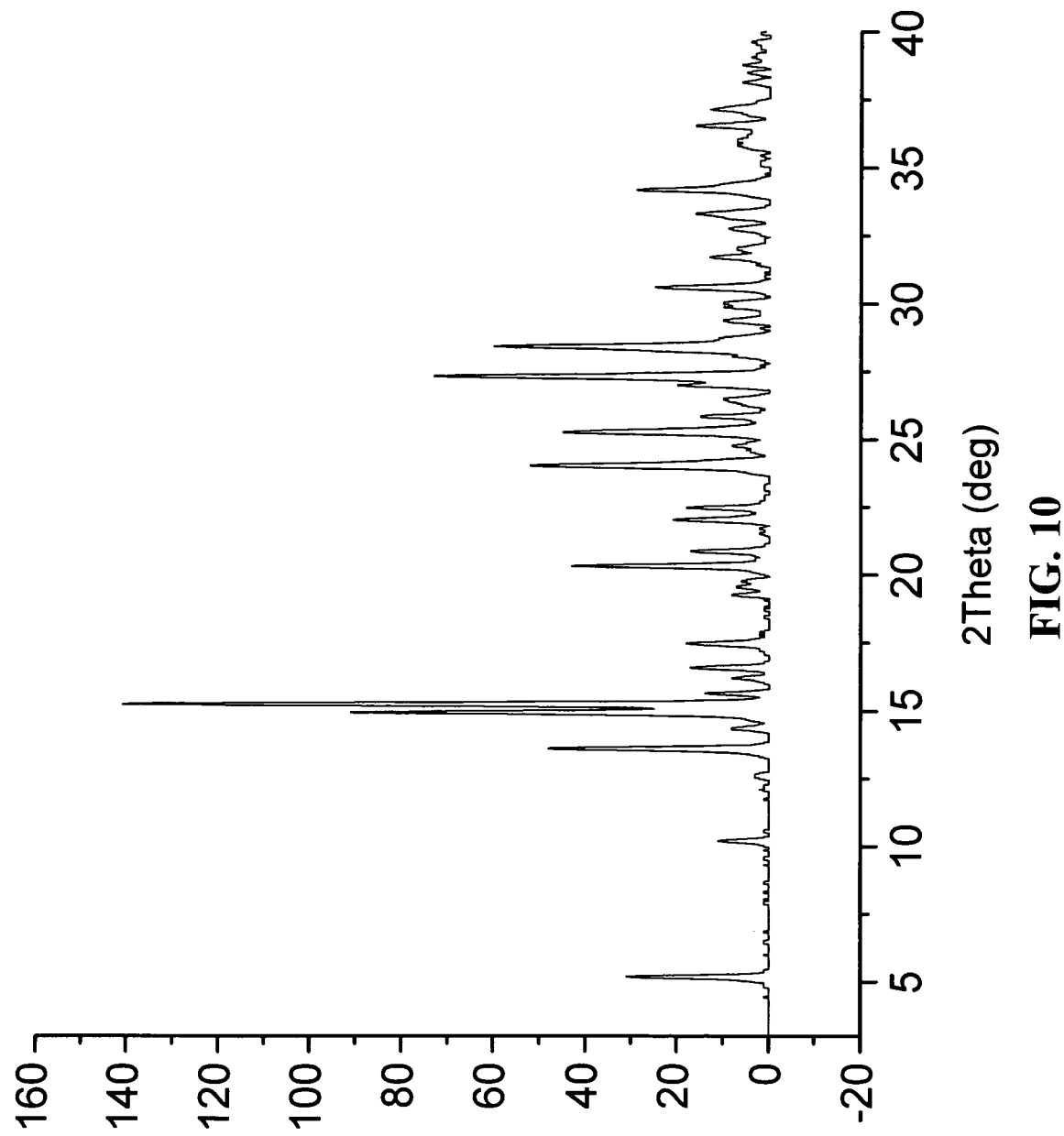
FIG. 10—PXRD diffractogram of lamotrigine saccharinate salt.

Crystalline lamotrigine saccharinate also has been evaluated by a PXRD diffractogram shown in FIG. 10.

Figure 11:
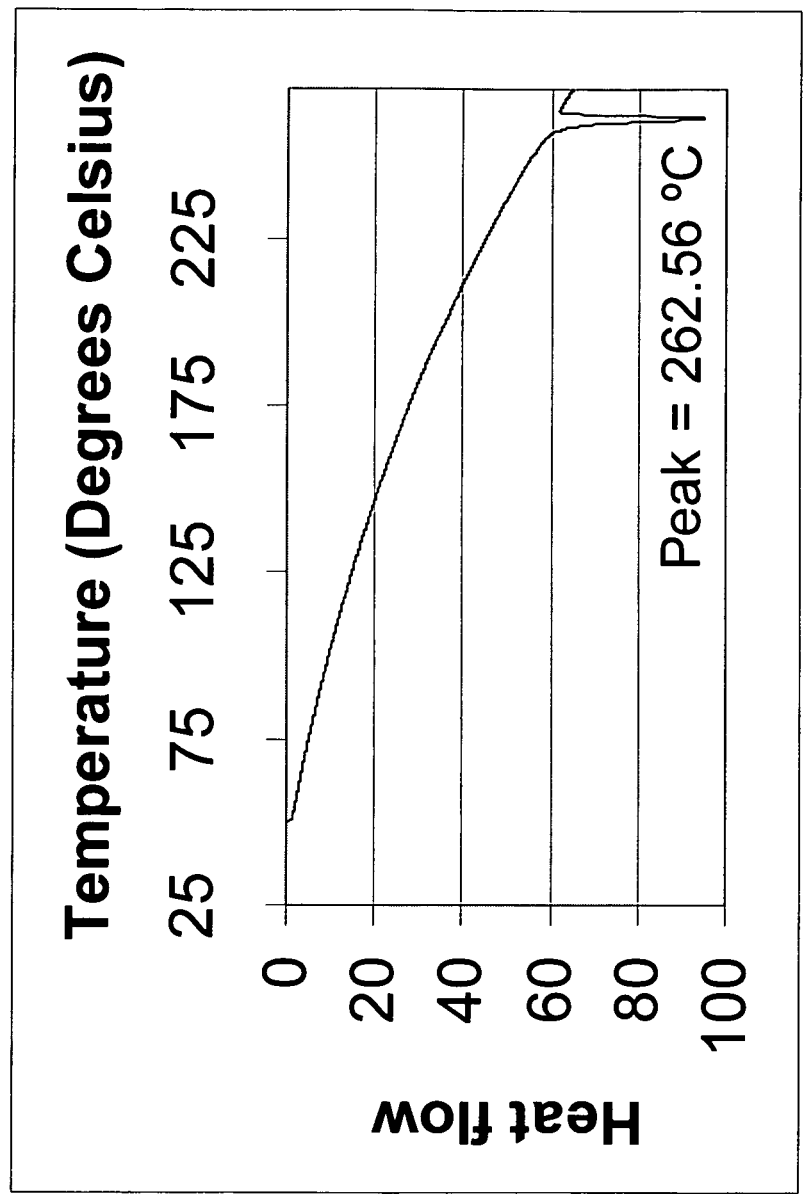
FIG. 11—DSC thermogram of lamotrigine saccharinate salt.

Crystalline lamotrigine saccharinate has been evaluated by a DSC phase transition shown in FIG. 11.

Figure 12:
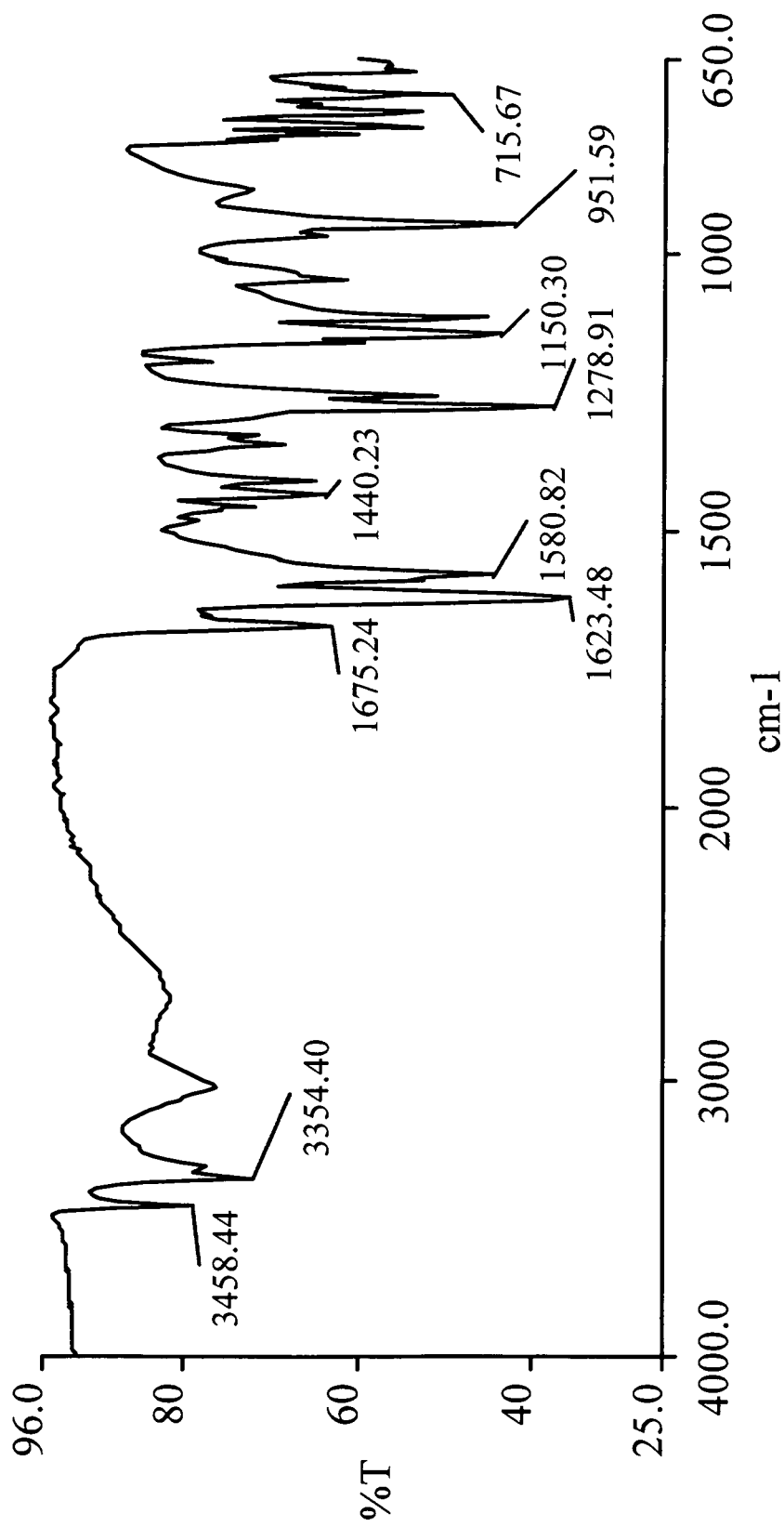
FIG. 12—Infrared spectrum for lamotrigine saccharinate salt.
Figure 13:
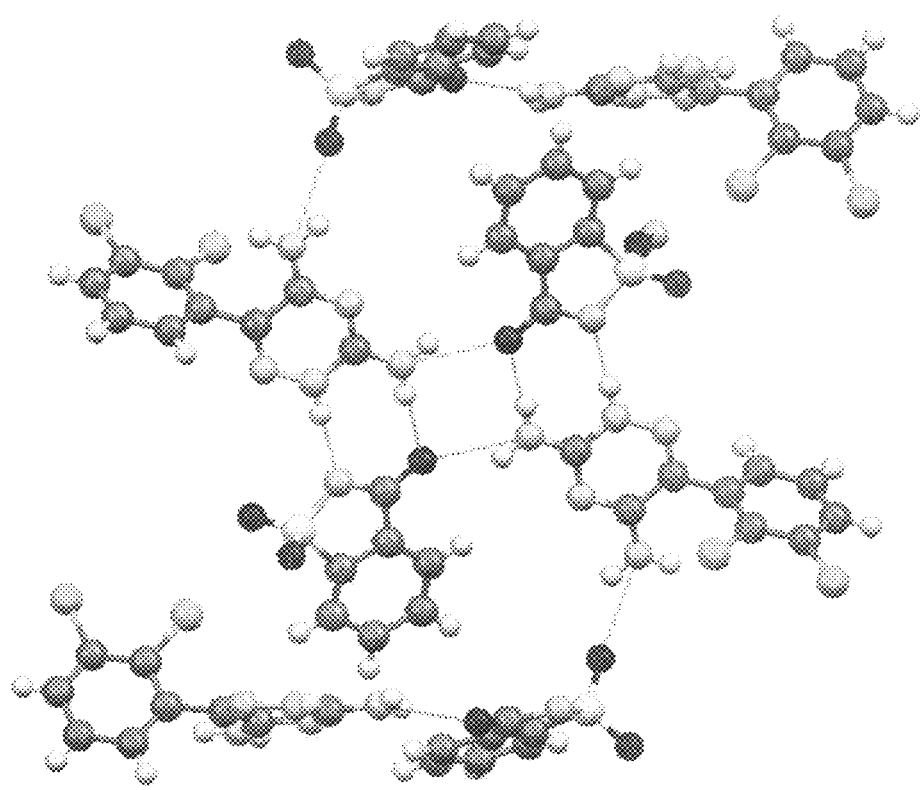
FIG. 13—Packing diagram for lamotrigine saccharinate salt.

Crystalline lamotrigine saccharinate has been evaluated by an FT-IR spectrum pattern as shown substantially in FIG. 12.

Another aspect of the present invention provides a salt comprising lamotrigine and adipic acid, which has been evaluated by its x-ray single crystal structure, x-ray powder diffraction pattern, and infra-red absorption spectrum.

Crystalline lamotrigine adipate has been evaluated by the single crystal x-ray diffraction data as shown in Example 8.

Figure 14:
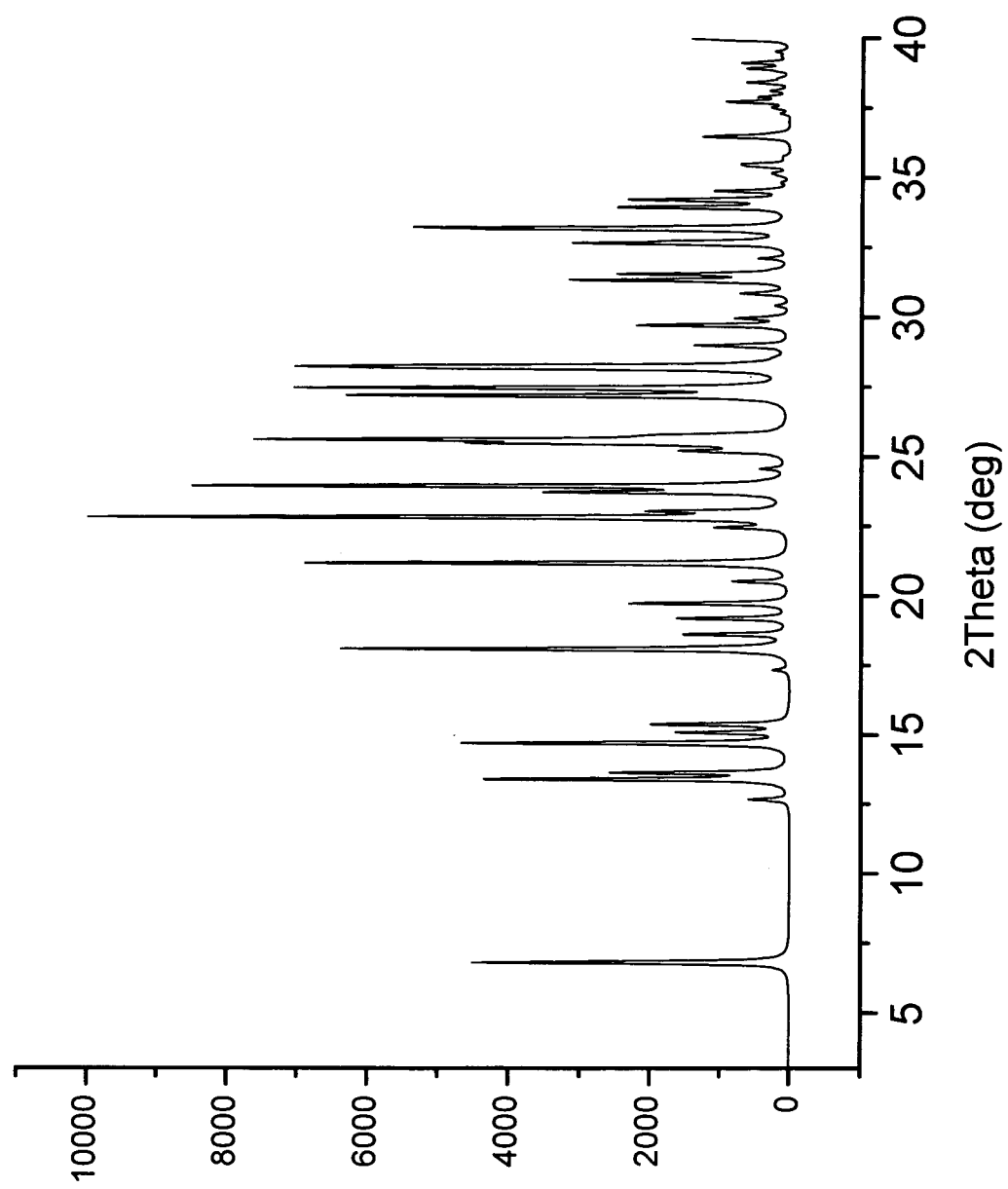
FIG. 14—Calculated PXRD diffractogram for lamotrigine adipate salt.

Crystalline lamotrigine and adipate has been evaluated by a calculated PXRD diffractogram shown in FIG. 14.

Figure 15:
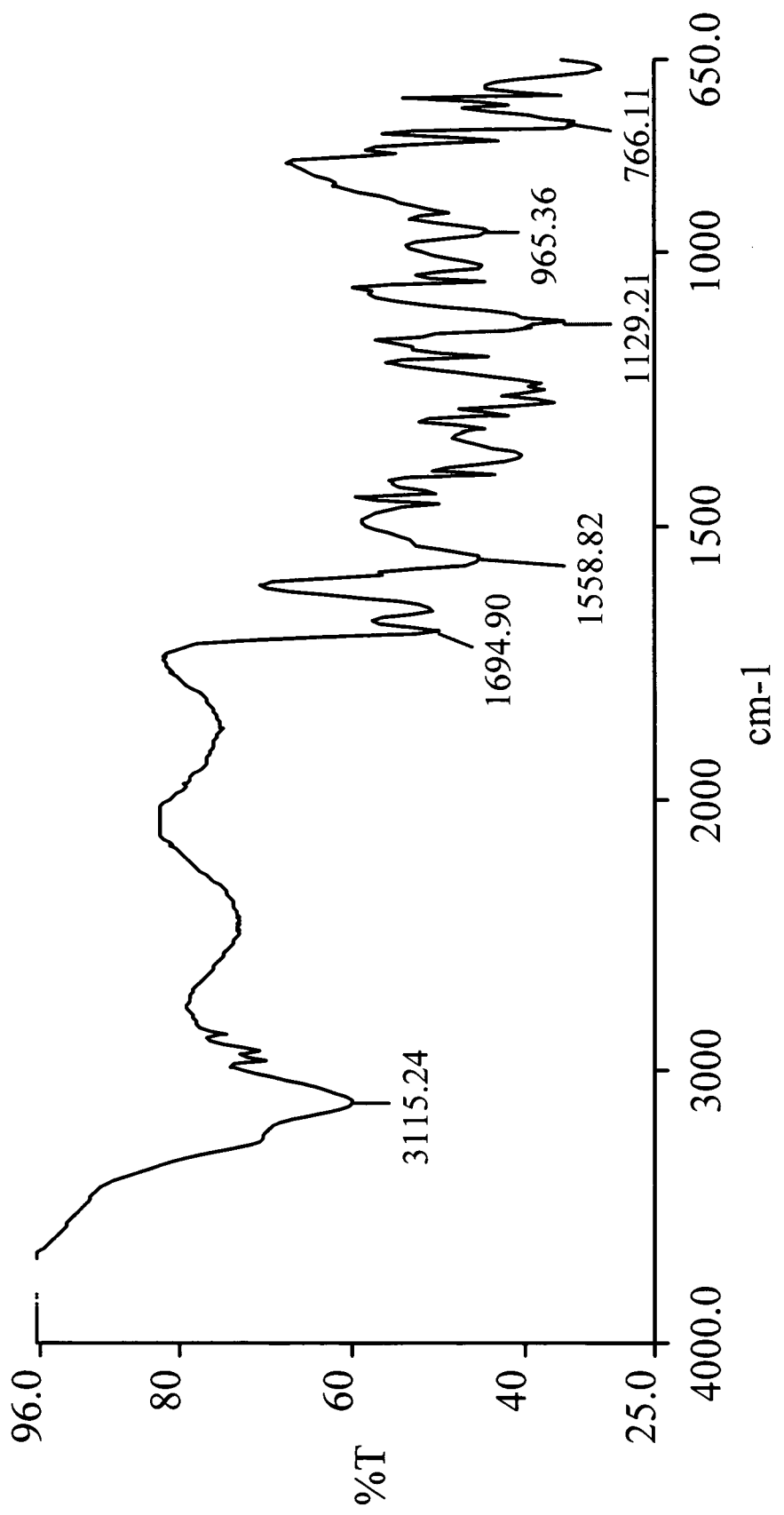
FIG. 15—Infrared spectrum for lamotrigine adipate salt.
Figure 16:
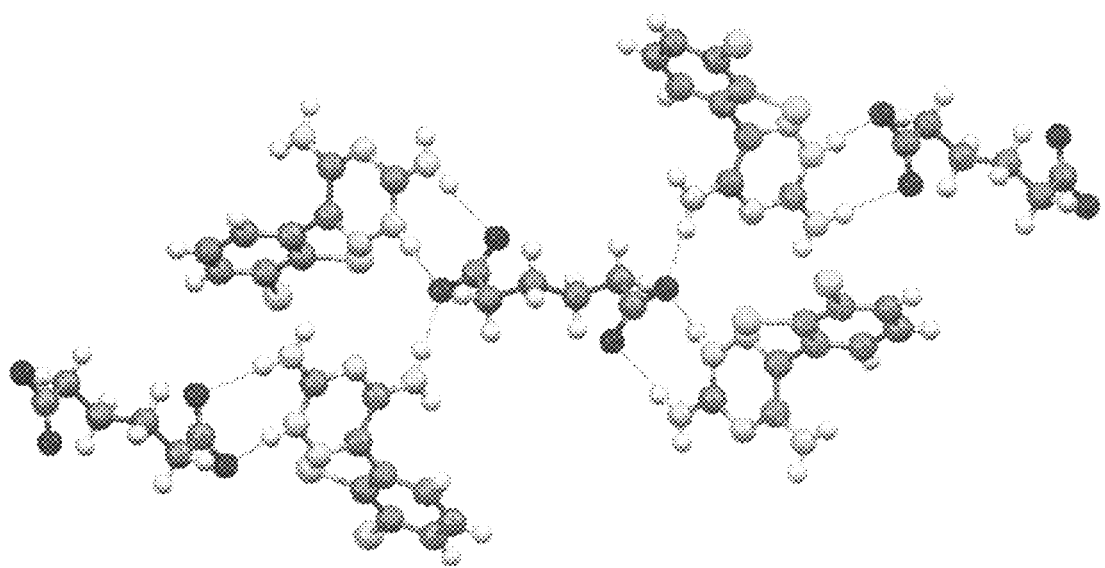
FIG. 16—Packing diagram for lamotrigine adipate salt.

Crystalline lamotrigine adipate has been evaluated by an FT-IR spectrum pattern as shown substantially in FIG. 15.

Another aspect of the present invention provides a salt comprising lamotrigine and malic acid, which has been evaluated by its x-ray single crystal structure, x-ray powder diffraction pattern, and infra-red absorption spectrum.

Crystalline lamotrigine malate has been evaluated by the single crystal x-ray diffraction data as shown in Example 9.

Figure 17:
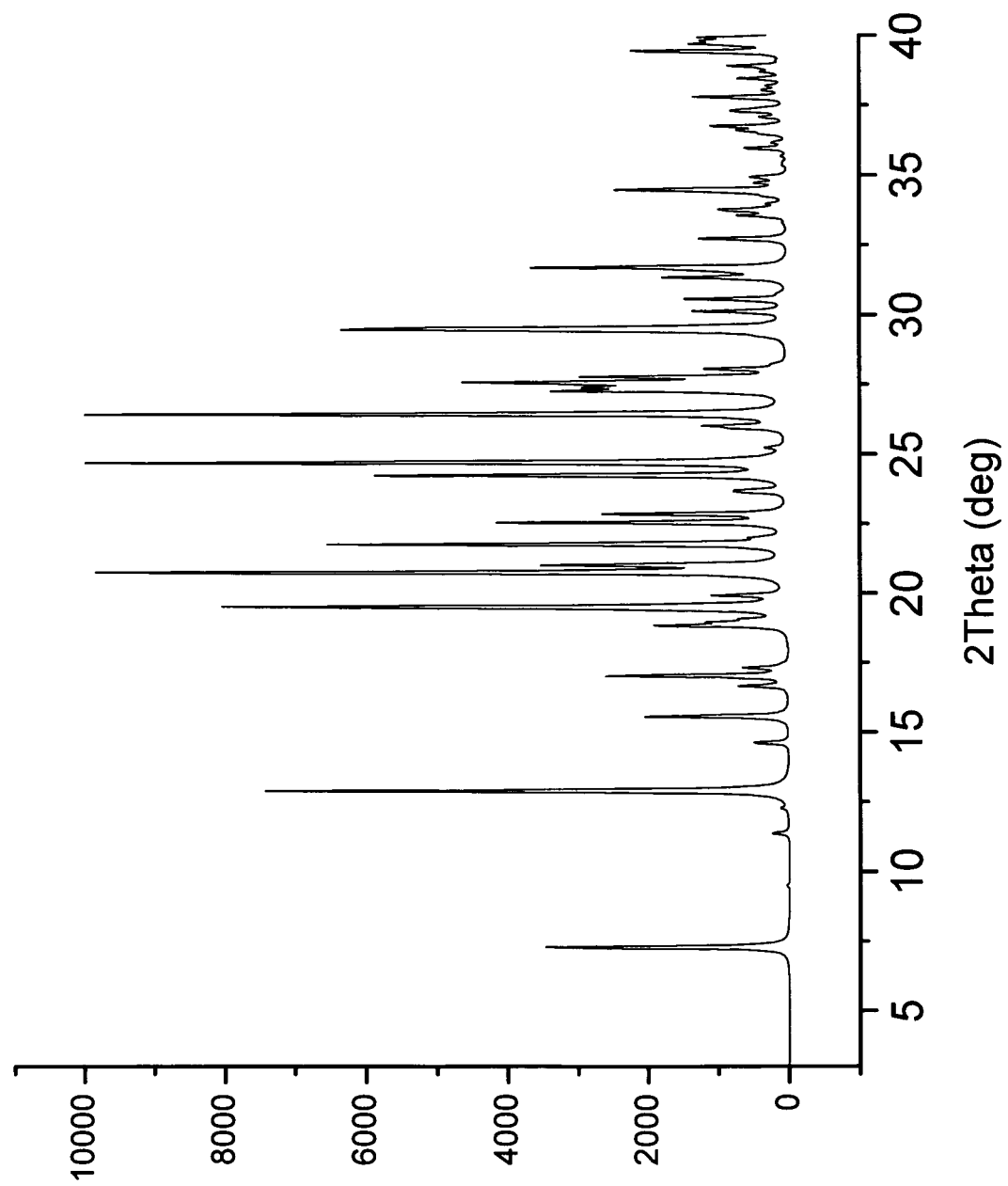
FIG. 17—Calculated PXRD diffractogram for lamotrigine malate salt.

Crystalline lamotrigine malate has been evaluated by a calculated PXRD diffractogram shown in FIG. 17.

Figure 18:
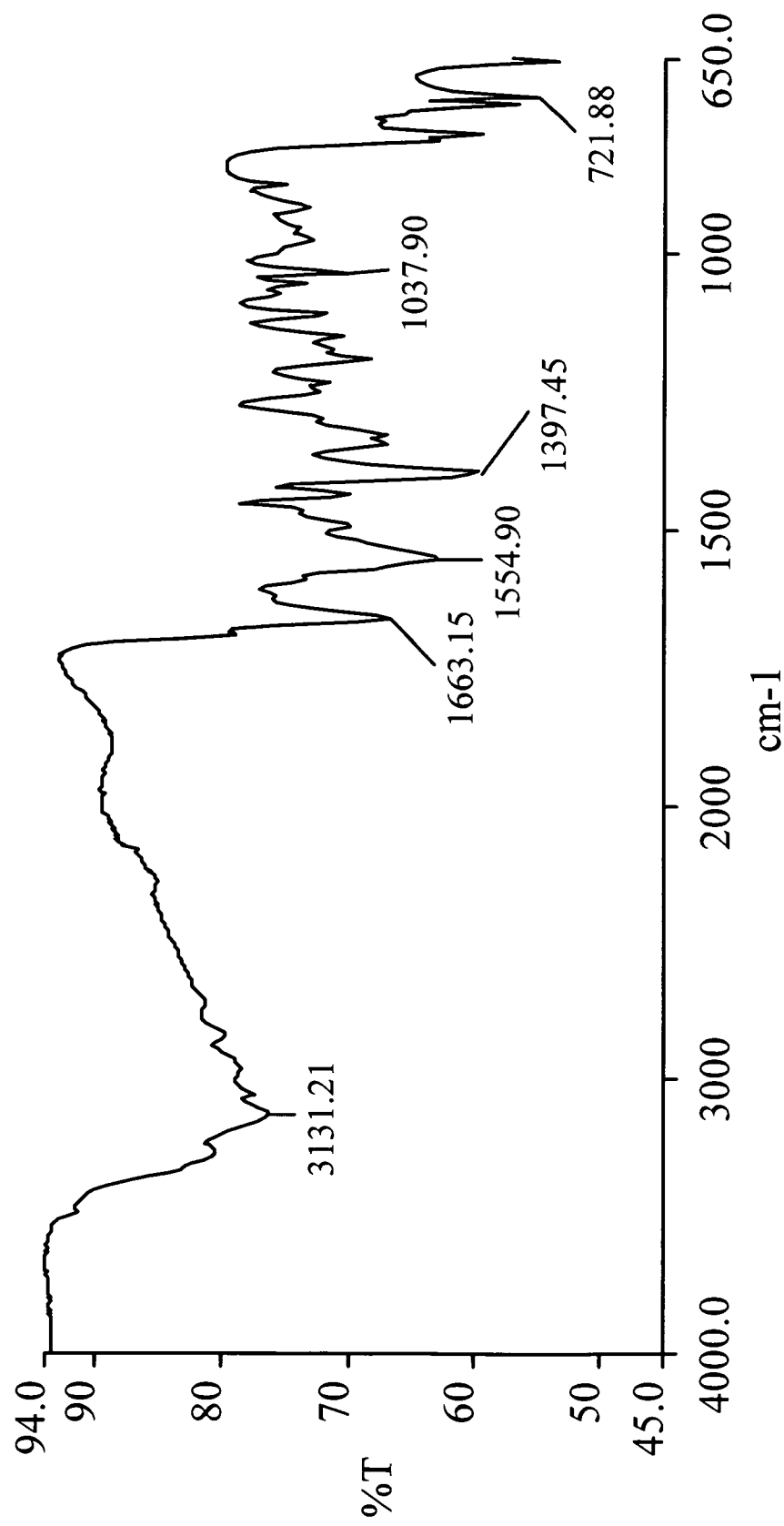
FIG. 18—Infrared spectrum for lamotrigine malate salt.
Figure 19:
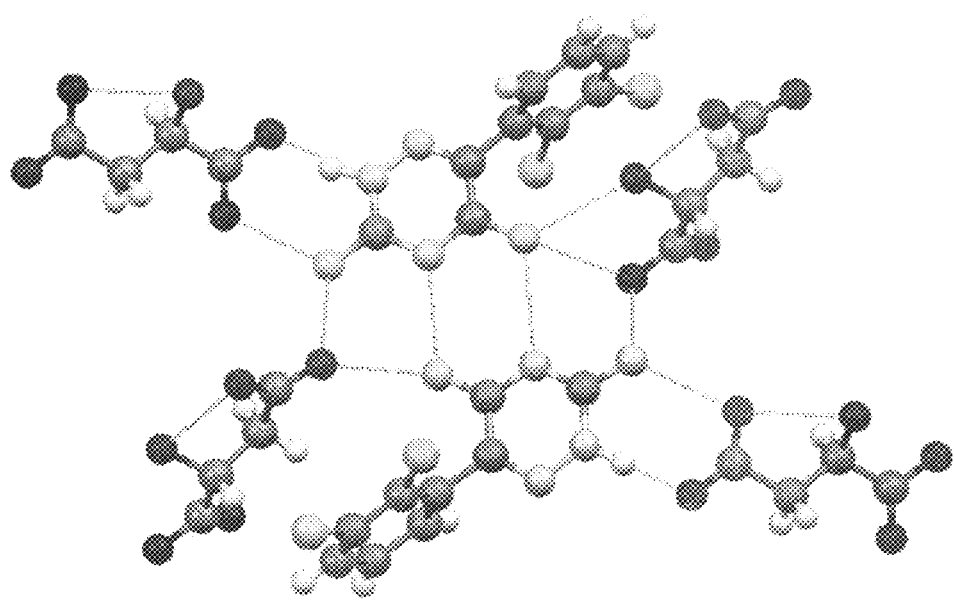
FIG. 19—Packing diagram for lamotrigine malate salt.

Crystalline lamotrigine malate has been evaluated by an FT-IR spectrum pattern as shown substantially in FIG. 18.

Another aspect of the present invention provides a methanol solvate of the salt comprising lamotrigine and nicotinic acid, which has been evaluated by its x-ray single crystal structure, x-ray powder diffraction pattern, and infra-red absorption spectrum.

More specifically, crystalline lamotrigine nicotinate methanolate has been evaluated by the single crystal x-ray diffraction data as shown in Example 10.

Figure 20:
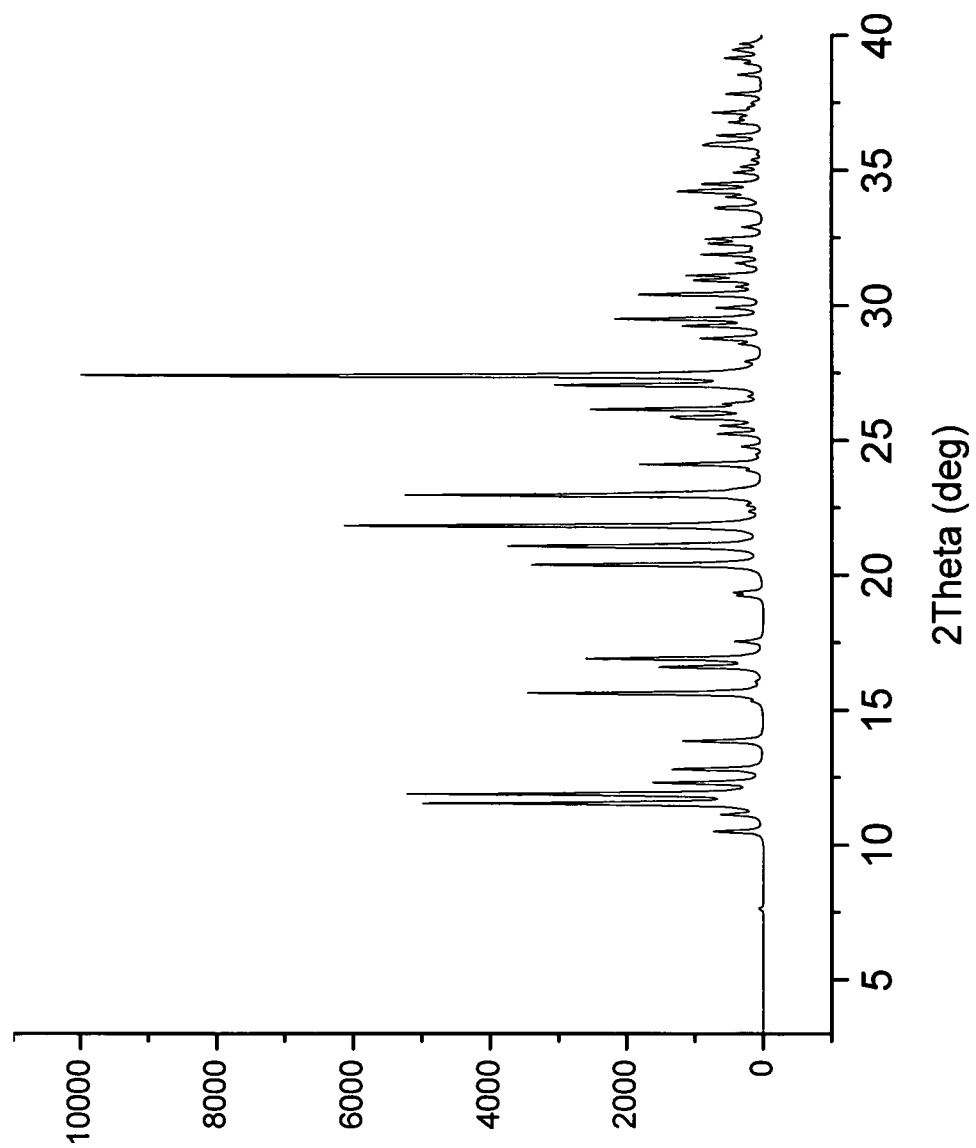
FIG. 20—Calculated PXRD diffractogram for lamotrigine methanol solvate of lamotrigine nicotinate salt.

Crystalline lamotrigine nicotinate methanolate has been evaluated by a calculated PXRD diffractogram shown in FIG. 20.

Figure 21:
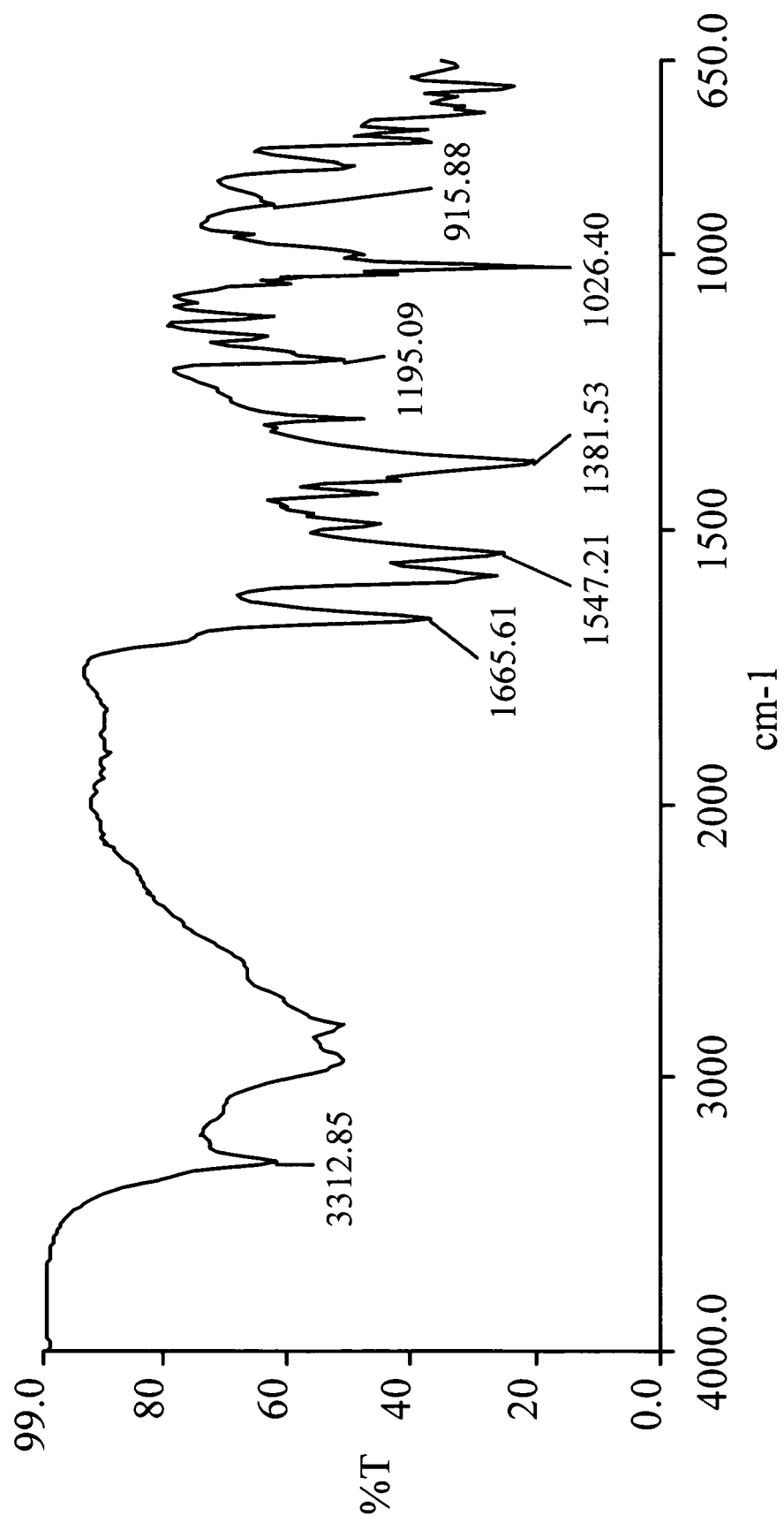
FIG. 21—Infrared spectrum for lamotrigine methanol solvate of lamotrigine nicotinate salt.
Figure 22:
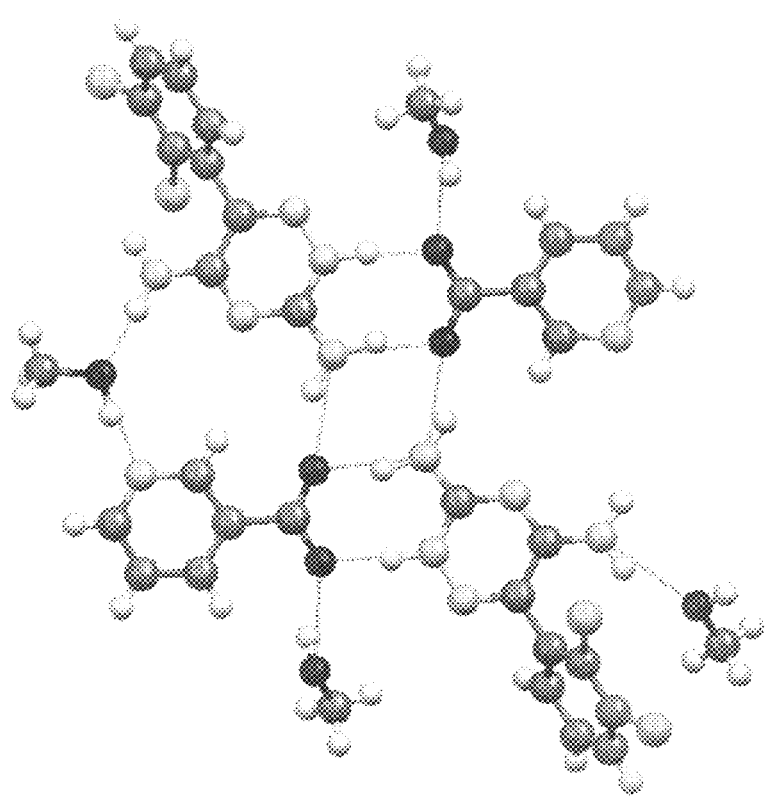
FIG. 22—Packing diagram for methanol solvate of lamotrigine nicotinate salt.

Crystalline lamotrigine nicotinate methanolate is identified by an FT-IR spectrum pattern as shown substantially in FIG. 21.

Another aspect of the present invention provides a disolvate of lamotrigine (dimethanolate), which has been evaluated by its x-ray single crystal structure, x-ray powder diffraction pattern, and infra-red absorption spectrum.

Crystalline lamotrigine methanolate has been evaluated by the single crystal x-ray diffraction data as shown in Example 11.

Figure 23:
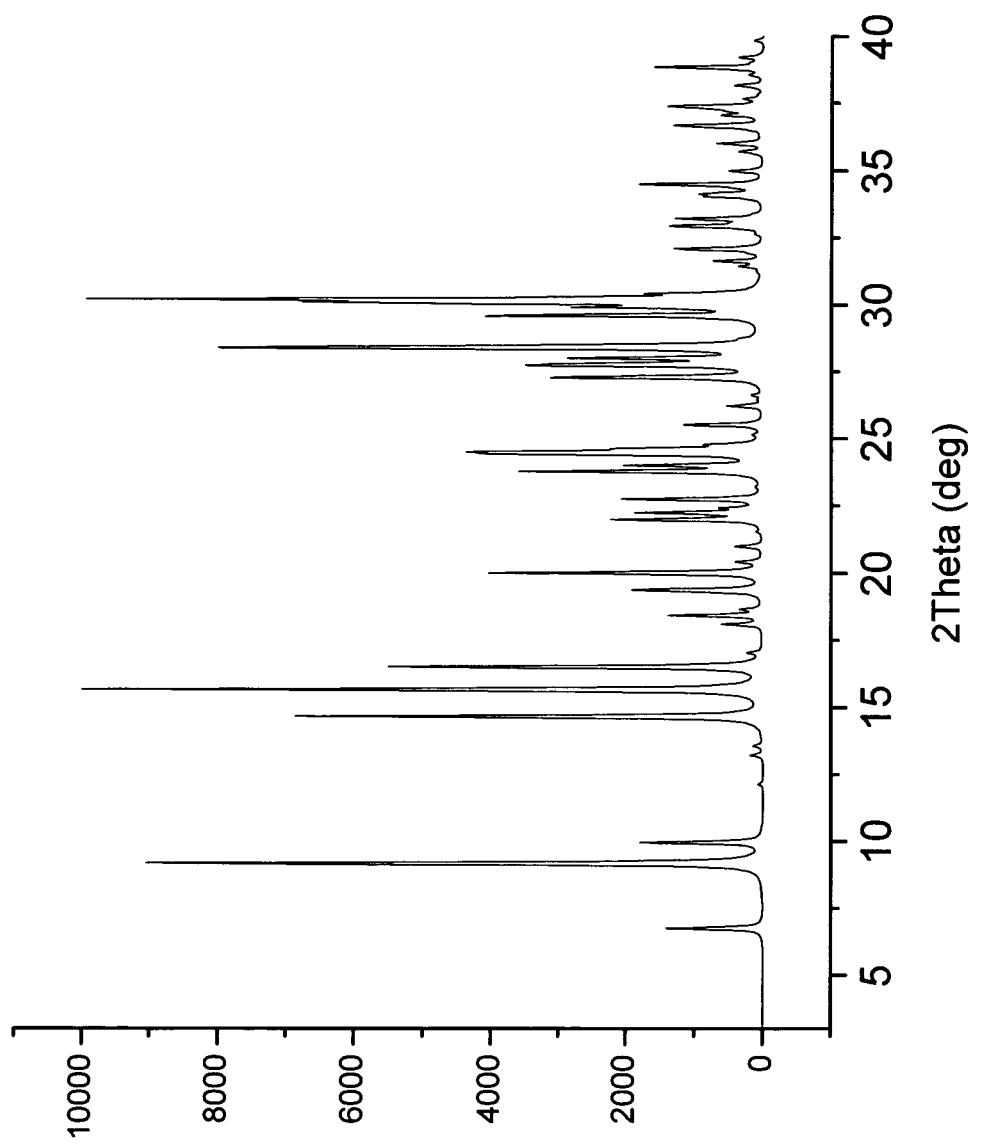
FIG. 23—Calculated PXRD diffractogram of a solvate comprising lamotrigine and methanol.

Crystalline lamotrigine methanolate has been evaluated by a calculated PXRD diffractogram shown in FIG. 23.

Figure 24:
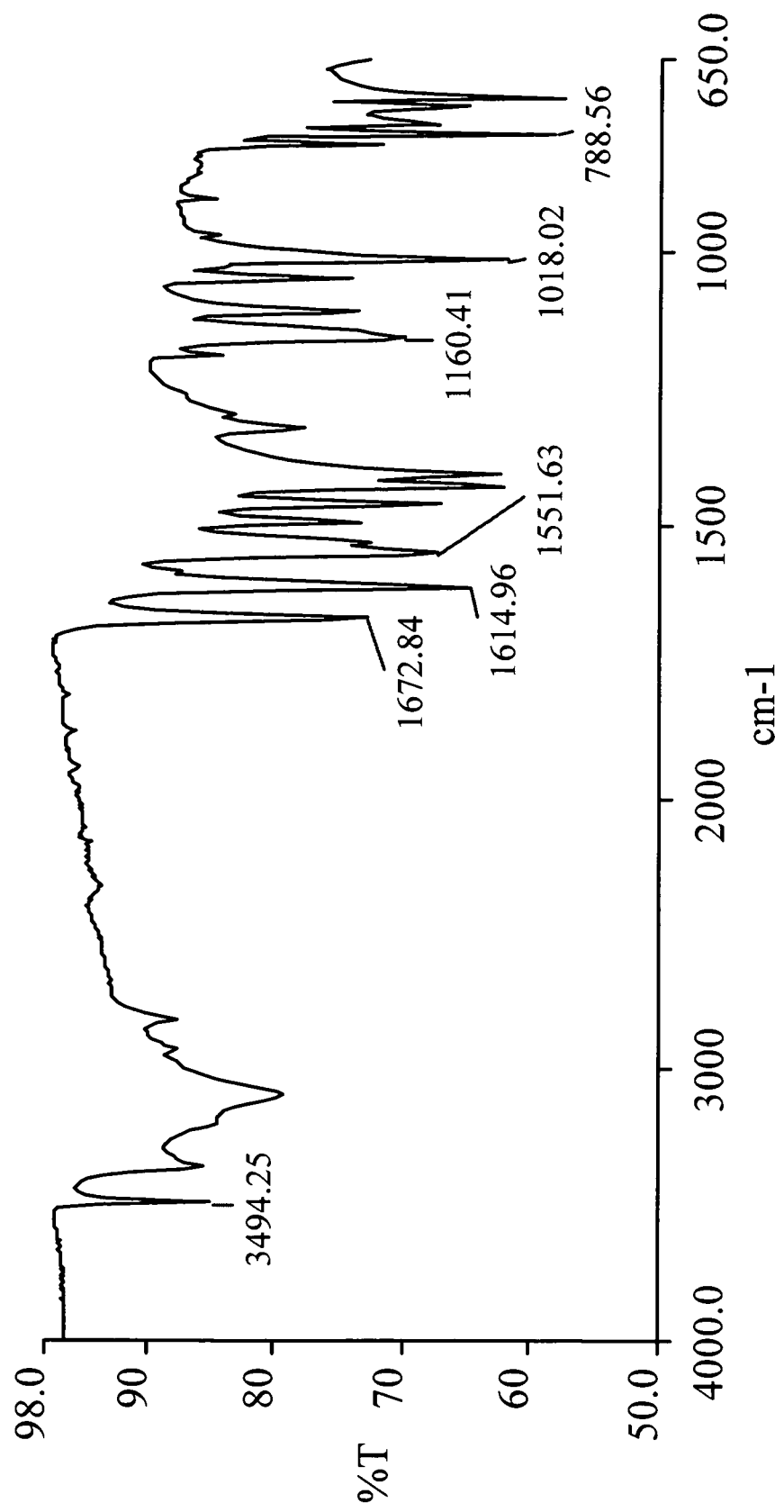
FIG. 24—Infrared spectrum for lamotrigine and methanol.
Figure 25:
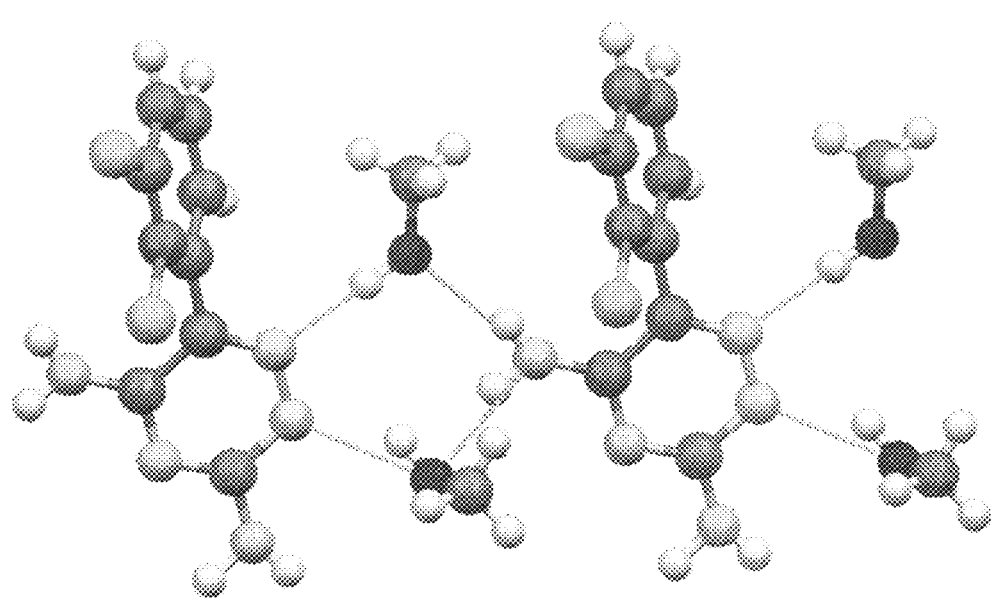
FIG. 25—Packing diagram for methanol solvate of lamotrigine dimethanol solvate.

Crystalline lamotrigine methanolate has been evaluated by an FT-IR spectrum pattern as shown substantially in FIG. 24.

Another aspect of the present invention provides a hydrate of larnotrigine ethanolate, which has been evaluated by its x-ray single crystal structure, x-ray powder diffraction pattern, and infra-red absorption spectrum.

Crystalline lamotrigine ethanolate hydrate has been evaluated by the single crystal x-ray diffraction data as shown in Example 12.

Figure 26:
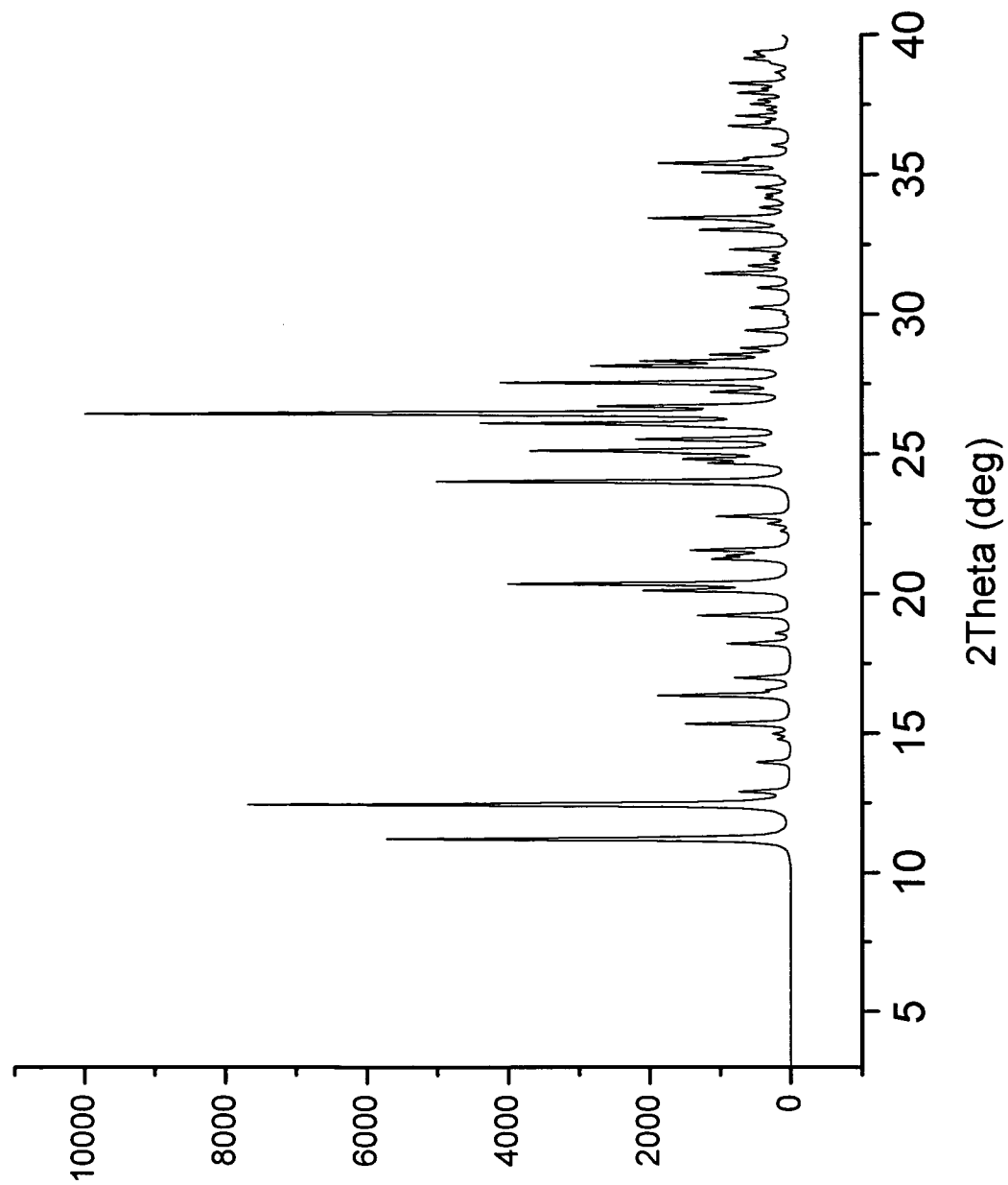
FIG. 26—Calculated PXRD diffractogram of a solvate comprising lamotrigine, ethanol and water.

Crystalline lamotrigine ethanolate hydrate has been evaluated by a calculated PXRD diffractogram shown in FIG. 26.

Figure 27:
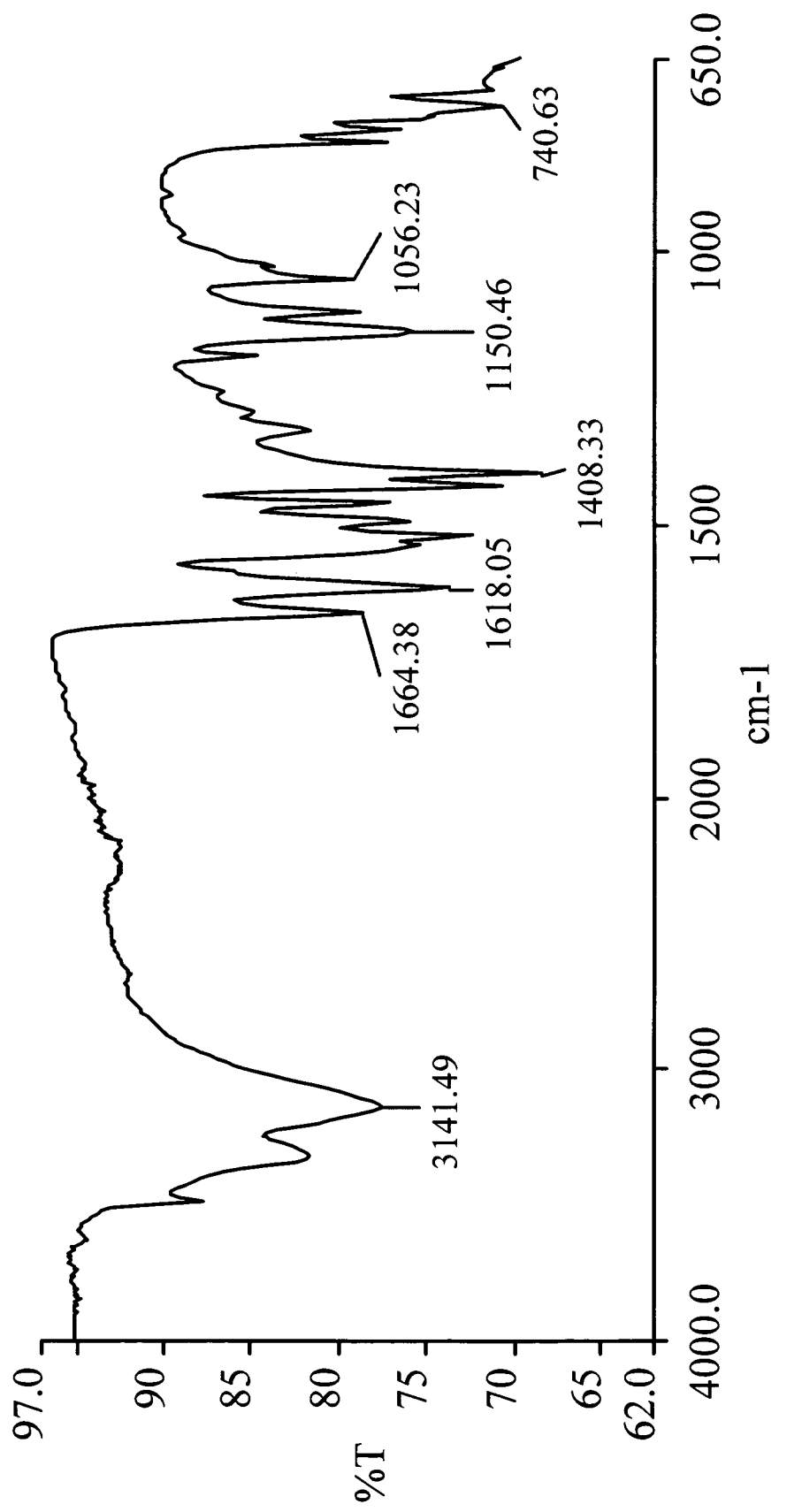
FIG. 27—Infrared spectrum for lamotrigine ethanolate hydrate.
Figure 28:
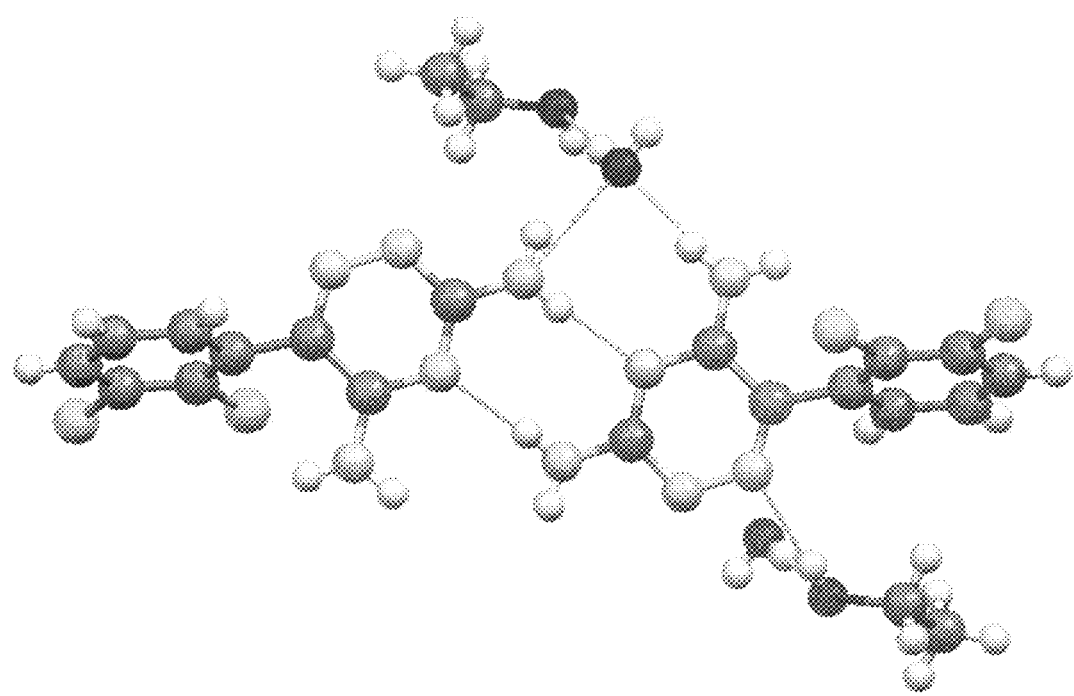
FIG. 28—Packing diagram for lamotrigine ethanolate hydrate.

Crystalline lamotrigine ethanolate hydrate has been evaluated by an FT-IR spectrum pattern as shown substantially in FIG. 27.

Another aspect of the present invention provides a hydrate of lamotrigine, which has been evaluated by its x-ray powder diffraction pattern, differential scanning calorimetry curve and infra-red absorption spectrum.

Figure 29:
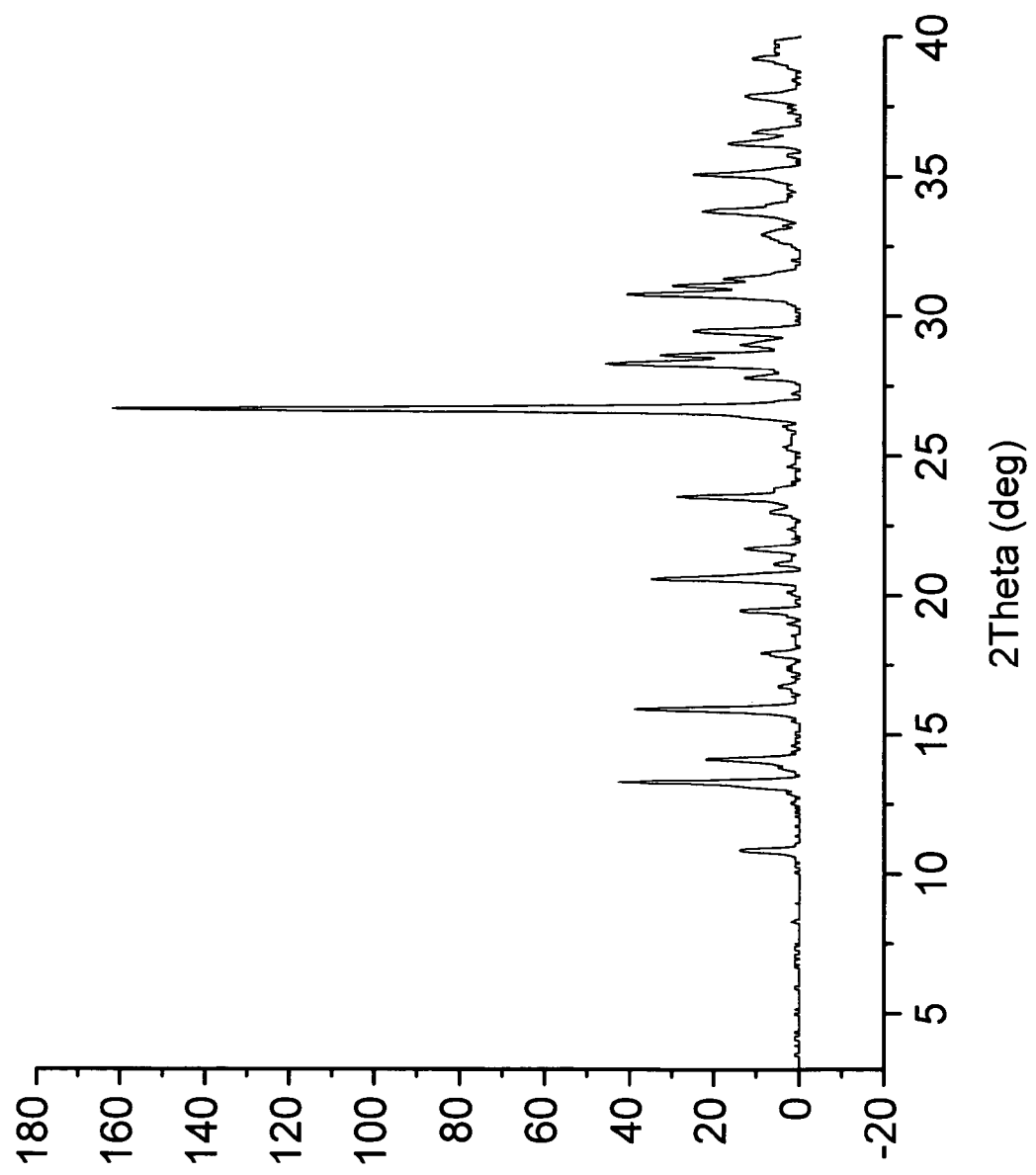
FIG. 29—PXRD diffractogram for lamotrigine hydrate form II (from the conversion of lamotrigine in water).

More specifically, crystalline lamotrigine hydrate form II has been evaluated by a PXRD diffractogram shown in FIG. 29.

Figure 30:
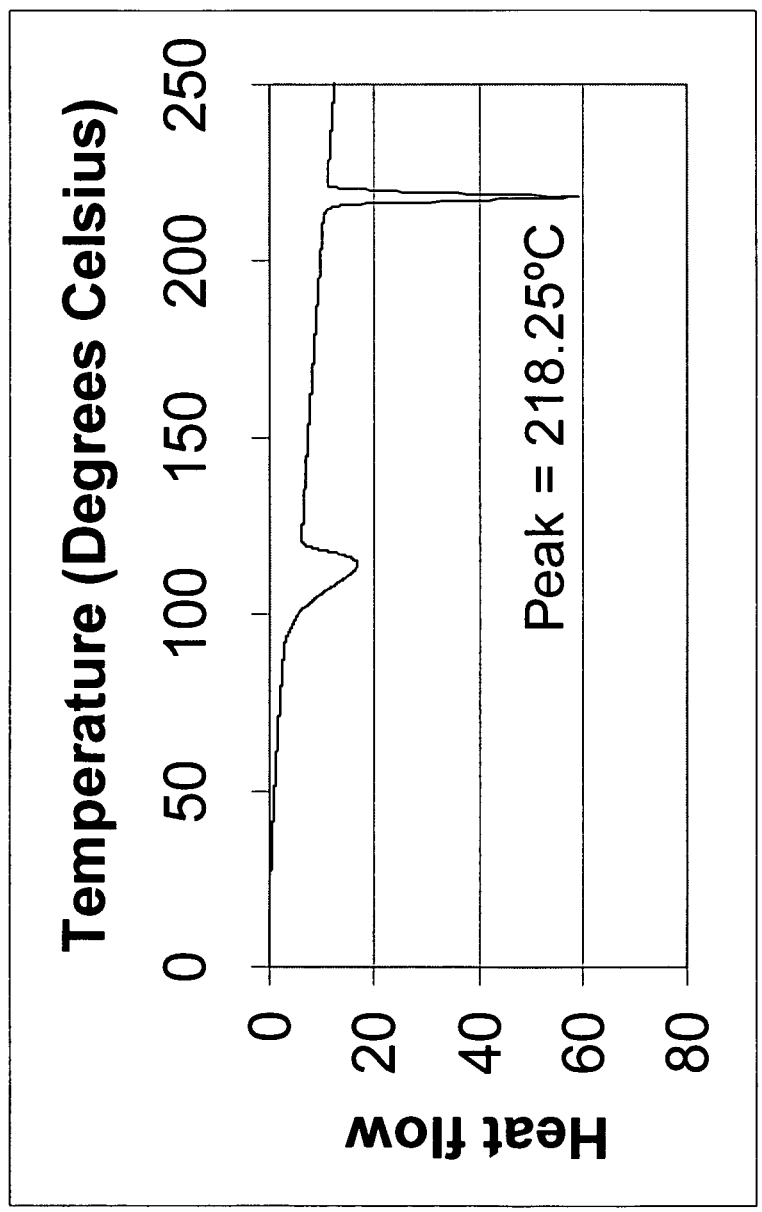
FIG. 30—DSC thermogram of lamotrigine hydrate form II (from the conversion of lamotrigine in water).

Crystalline lamotrigine hydrate form II has been evaluated by two DSC phase transitions shown in FIG. 30.

Another aspect of the invention provides co-crystals of: lamotrigine:methylparaben form I, lamotrigine:methylparaben form II and lamotrigine:nicotinamide co-crystal, salts of lamotrigine saccharinate, lamotrigine adipate, lamotrigine malate, methanol solvate of lamotrigine nicotinate salt, dimethanol solvate, ethanolate hydrate and hydrate of lamotrigine suitable for a pharmaceutical formulation than can be delivered via different routes to the human body.

Pharmaceutical compositions of the present invention contain any of the lamotrigine forms disclosed therein, either alone or in combination, and optionally in combination with other active ingredients. In addition to the active ingredient(s), the pharmaceutical compositions of the present invention may contain one or more excipients. Excipients are added to the composition for a variety of purposes.

Diluents increase the bulk of a solid pharmaceutical composition, and may make a pharmaceutical dosage form containing the composition easier for the patient and care giver to handle. Diluents for solid compositions include, for example, microcrystalline cellulose (e.g. Avicel®), microfine cellulose, lactose, starch, pregelitinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol and talc.

Solid pharmaceutical compositions that are compacted into a dosage form such as a tablet may include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate and starch.

The dissolution rate of a compacted solid pharmaceutical composition in the patient's stomach may be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®) and starch.

Glidants can be added to improve the flowability of a non-compacted solid composition and to improve the accuracy of dosing. Excipients that may function as glidants include colloidal silicon dixoide, magnesium trisilicate, powdered cellulose, starch, talc and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

Flavoring agents and flavor enhancers make the dosage form more palatable to the patient. Common flavoring agents and flavor enhancers for pharmaceutical products that may be included in the composition of the present invention include maltol, vanillin, ethyl vanillin, menthol, citric acid, fumaric acid, ethyl maltol, and tartaric acid.

Solid and liquid compositions may also be dyed using any pharmaceutically acceptable colorant to improve their appearance and/or facilitate patient identification of the product and unit dosage level.

In liquid pharmaceutical compositions of the present invention, the lamotrigine co-crystals and any other solid excipients are dissolved or suspended in a liquid carrier such as water, vegetable oil, alcohol, polyethylene glycol, propylene glycol or glycerin.

Liquid pharmaceutical compositions may contain emulsifying agents to disperse uniformly throughout the composition an active ingredient or other excipient that is not soluble in the liquid carrier. Emulsifying agents that may be useful in liquid compositions of the present invention include, for example, gelatin, egg yolk, casein, cholesterol, acacia, tragacanth, chondrus, pectin, methyl cellulose, carbomer, cetostearyl alcohol and cetyl alcohol.

Liquid pharmaceutical compositions of the present invention may also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

Sweetening agents such as sorbitol, saccharin, sodium saccharin, sucrose, aspartame, fructose, mannitol and invert sugar may be added to improve the taste.

Preservatives and chelating agents such as alcohol, sodium benzoate, butylated hydroxy toluene, butylated hydroxyanisole and ethylenediamine tetraacetic acid may be added at levels safe for ingestion to improve storage stability.

According to the present invention, a liquid composition may also contain a buffer such as guconic acid, lactic acid, citric acid or acetic acid, sodium guconate, sodium lactate, sodium citrate or sodium acetate.

Selection of excipients and the amounts used may be readily determined by the formulation scientist based upon experience and consideration of standard procedures and reference works in the field.

The solid compositions of the present invention include powders, granulates, aggregates and compacted compositions. The dosages include dosages suitable for oral, buccal, rectal, parenteral (including subcutaneous, intramuscular, and intravenous), inhalant and ophthalmic administration. Although the most suitable administration in any given case will depend on the nature and severity of the condition being treated, the most preferred route of the present invention is oral. The dosages may be conveniently presented in unit dosage form and prepared by any of the methods well-known in the pharmaceutical arts.

Dosage forms include solid dosage forms like tablets, powders, capsules, suppositories, sachets, troches and losenges, as well as liquid syrups, suspensions and elixirs.

The dosage form of the present invention may be a capsule containing the composition, preferably a powdered or granulated solid composition of the invention, within either a hard or soft shell. The shell may be made from gelatin and optionally contain a plasticizer such as glycerin and sorbitol, and an opacifying agent or colorant.

The active ingredient and excipients may be formulated into compositions and dosage forms according to methods known in the art.

A tableting composition may be prepared conventionally by dry blending. For example, the blended composition of the actives and excipients may be compacted into a slug or a sheet and then comminuted into compacted granules. The compacted granules may subsequently be compressed into a tablet.

As an alternative to dry granulation, a blended composition may be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate and colloidal silica. The proper use of these and other excipients in direct compression tableting is known to those in the art with experience and skill in particular formulation challenges of direct compression tableting.

A capsule filling of the present invention may comprise any of the aforementioned blends and granulates that were described with reference to tableting, only they are not subjected to a final tableting step.

Another aspect of the invention includes those crystalline forms of lamotrigine (and/or dosage forms containing one or more of such forms) that are capable of achieving certain dissolution profiles for lamotrigine at pH 1 (0.1 M HCl, 37° C.) and/or in water (25° C.).

Another aspect of the invention includes those crystalline forms of lamotrigine (and/or dosage forms containing one or more of such forms) that lead to dissolution profiles which show an increase in the solubility of lamotrigine:methylparaben co-crystal form II and lamotrigine:nicotinamide co-crystal in comparison with lamotrigine at pH 1.

Another aspect of the invention includes those crystalline forms of lamotrigine (and/or dosage forms containing one or more of such forms) that lead to dissolution profiles which show an increase in the solubility of lamotrigine:methylparaben form II co-crystal, lamotrigine:nicotinamide co-crystal, and lamotrigine saccharinate in comparison with lamotrigine in water.

Another aspect of the invention includes those novel crystalline forms of lamotrigine (and/or dosage forms containing one or more of such forms) that lead to substantially improved in-vivo absorption profile of lamotrigine:saccharine in comparison with that of pure lamotrigine in a 24 hr rat study (N=5).

Another aspect of the invention includes those novel crystalline forms of lamotrigine (and/or dosage forms containing one or more of such forms) that lead to lower in-vivo absorption profile of lamotrigine:nicotinamide in comparison with that of pure lamotrigine in a 24 hr rat study (N=5) suitable for sustained release that is beneficial in the treatment of epilepsy since it is thought that too-low troughs in the peak plasma concentration may lead to breakthrough seizures and result in some adverse events (AE) occurring in some patients.

The following examples illustrate the invention without intending to limit the scope of the invention. While the following examples use specific solvents, one of skill in the art would understand that any appropriate organic solvent could be used in the production of the various co-crystals of the present invention. Such organic solvents include, but are not limited to, methanol, mixtures of water and methanol, ethanol, mixtures of water and ethanol, propan-2-ol and mixtures of water and propan-2-ol, tetrahydrofuran (THF) and mixtures of THF and water, acetonitrile and mixtures of propan-1-ol and water.

Each of the references, patents and publications cited herein are incorporated herein by reference in their entirety.

Example 1

Preparation of Lamotrigine:Methylparaben Co-Crystal Form I 11 mg of lamotrigine was dissolved in 2 ml of THF (tetrahydrofuran), 7.5 mg of methylparaben was added to the solution to form a single solution. The solution was then allowed to stand for several hours to affect the slow evaporation of solvent. The solids gathered were stored in screw cap vials for subsequent analysis.

The single crystal x-ray diffraction data for lamotrigine:methylparaben co-crystal form I is provided below. The PXRD diffractogram is shown in FIG. 1.

TABLE 1-1

Crystal data and structure refinement for lamotrigine:methylparaben co-crystal form I

| | |
|---|---|
| Empirical formula | C17 H15 C12 N5 O3 |
| Formula weight | 408.24 |
| Temperature | 100 (2) K |
| Wavelength | 0.71073 Å |
| Crystal system | Monoclinic |
| Space group | P2 (1)/n |

TABLE 1-1-continued

Crystal data and structure refinement for lamotrigine: methylparaben co-crystal form I

| | | |
|---|---|---|
| Unit cell dimensions | a = 5.273 (2) Å | α = 90°. |
| | b = 14.330 (6) Å | β = 92.795(10)°. |
| | c = 23.822 (10) Å | γ = 90°. |
| Volume | 1797.9 (13) Å$^3$ | |
| Z | 4 | |
| Density (calculated) | 1.508 Mg/m$^3$ | |
| Absorption coefficient | 0.391 mm$^{-1}$ | |
| F(000) | 840 | |
| Theta range for data collection | 1.66 to 23.32°. | |
| Index ranges | −5 <= h <= 3, | |
| | −14 <= k <= 15, | |
| | −26 <= l <= 23 | |
| Reflections collected | 7629 | |
| Independent reflections | 2587 [R (int) = 0.1275] | |
| Completeness to theta = 23.32° | 99.8% | |
| Refinement method | Full-matrix least-squares on F$^2$ | |
| Data/restraints/parameters | 2587/0/245 | |
| Goodness-of-fit on F$^2$ | 1.000 | |
| Final R indices [I > 2sigma(I)] | R1 = 0.0615, wR2 = 0.1189 | |
| R indices (all data) | R1 = 0.1006, wR2 = 0.1313 | |
| Largest diff. peak and hole | 0.341 and −0.331 e · Å$^{-3}$ | |

TABLE 1-2

Atomic coordinates (×10$^4$) and equivalent isotropic displacement parameters (Å$^2$ × 10$^3$) for lamotrigine: methylparaben co-crystal form I. U(eq) is defined as one third of the trace of the orthogonalized U$^{ij}$ tensor.

| | x | y | z | U(eq) |
|---|---|---|---|---|
| Cl(1) | 6277 (2) | 9615 (1) | 637 (1) | 32 (1) |
| Cl(2) | 7980 (3) | 11642 (1) | 306 (1) | 45 (1) |
| N(5) | 9029 (7) | 7156 (3) | 1685 (2) | 24 (1) |
| N(2) | 6237 (7) | 8020 (3) | 2260 (2) | 24 (1) |
| N(1) | 7127 (7) | 8832 (3) | 2059 (2) | 24 (1) |
| N(3) | 6425 (7) | 6420 (3) | 2299 (2) | 36 (1) |
| C(1) | 8900 (8) | 8821 (3) | 1694 (2) | 18 (1) |
| N(4) | 11751 (7) | 7960 (3) | 1135 (2) | 27 (1) |
| C(2) | 11924 (9) | 10162 (3) | 1761 (2) | 25 (1) |
| C(3) | 8702 (8) | 10170 (3) | 1027 (2) | 24 (1) |
| C(4) | 9848 (8) | 9740 (3) | 1490 (2) | 21 (1) |
| C(5) | 7270 (8) | 7229 (3) | 2068 (2) | 21 (1) |
| C(6) | 9917 (8) | 7952 (3) | 1507 (2) | 21 (1) |
| C(7) | 12768 (9) | 11021 (3) | 1583 (2) | 28 (1) |
| C(8) | 11563 (9) | 11469 (3) | 1139 (2) | 29 (1) |
| C(9) | 9509 (9) | 11052 (3) | 858 (2) | 27 (1) |
| O(2) | 7548 (6) | 5573 (2) | 389 (1) | 26 (1) |
| O(3) | 3000 (5) | 2950 (2) | 2197 (1) | 24 (1) |
| O(1) | 4306 (6) | 6494 (2) | 610 (1) | 28 (1) |
| C(10) | 3520 (8) | 3638 (3) | 1826 (2) | 21 (1) |
| C(11) | 4791 (8) | 5008 (3) | 1053 (2) | 22 (1) |
| C(12) | 5481 (8) | 5767 (4) | 674 (2) | 23 (1) |
| C(13) | 5631 (9) | 3526 (3) | 1500 (2) | 27 (1) |
| C(14) | 2662 (8) | 5120 (3) | 1372 (2) | 23 (1) |
| C(15) | 2012 (8) | 4431 (3) | 1754 (2) | 23 (1) |
| C(16) | 6248 (8) | 4203 (3) | 1124 (2) | 23 (1) |
| C(17) | 8454 (9) | 6329 (3) | 52 (2) | 31 (1) |

TABLE 1-3

Bond lengths [Å] and angles [°] for lamotrigine: methylparaben co-crystal form I.

| | | | |
|---|---|---|---|
| Cl(1)-C(3) | 1.736 (5) | C(4)-C(2)-C(7) | 120.4 (5) |
| Cl(2)-C(9) | 1.729 (5) | C(4)-C(3)-C(9) | 120.4 (5) |
| N(5)-C(6) | 1.311 (6) | C(4)-C(3)-Cl(1) | 120.4 (4) |
| N(5)-C(5) | 1.336 (5) | C(9)-C(3)-Cl(1) | 119.2 (4) |
| N(2)-C(5) | 1.347 (5) | C(3)-C(4)-C(2) | 119.0 (4) |
| N(2)-N(1) | 1.351 (5) | C(3)-C(4)-C(1) | 120.8 (4) |
| N(1)-C(1) | 1.308 (5) | C(2)-C(4)-C(1) | 120.1 (4) |
| N(3)-C(5) | 1.368 (6) | N(5)-C(5)-N(2) | 127.1 (4) |
| C(1)-C(6) | 1.436 (6) | N(5)-C(5)-N(3) | 117.3 (4) |
| C(1)-C(4) | 1.498 (6) | N(2)-C(5)-N(3) | 115.5 (4) |
| N(4)-C(6) | 1.344 (5) | N(5)-C(6)-N(4) | 120.1 (4) |
| C(2)-C(4) | 1.382 (6) | N(5)-C(6)-C(1) | 120.6 (4) |
| C(2)-C(7) | 1.383 (6) | N(4)-C(6)-C(1) | 119.3 (4) |
| C(3)-C(4) | 1.378 (7) | C(8)-C(7)-C(2) | 120.7 (5) |
| C(3)-C(9) | 1.399 (6) | C(7)-C(8)-C(9) | 119.7 (5) |
| C(7)-C(8) | 1.366 (7) | C(8)-C(9)-C(3) | 119.6 (5) |
| C(8)-C(9) | 1.381 (6) | C(8)-C(9)-Cl(2) | 118.9 (4) |
| O(2)-C(12) | 1.340 (5) | C(3)-C(9)-Cl(2) | 121.5 (4) |
| O(2)-C(17) | 1.444 (5) | C(12)-O(2)-C(17) | 115.2 (4) |
| O(3)-C(10) | 1.361 (5) | O(3)-C(10)-C(15) | 122.6 (4) |
| O(1)-C(12) | 1.217 (5) | O(3)-C(10)-C(13) | 117.9 (4) |
| C(10)-C(15) | 1.392 (6) | C(15)-C(10)-C(13) | 119.4 (5) |
| C(10)-C(13) | 1.398 (6) | C(16)-C(11)-C(14) | 118.9 (4) |
| C(11)-C(16) | 1.392 (6) | C(16)-C(11)-C(12) | 122.3 (4) |
| C(11)-C(14) | 1.394 (6) | C(14)-C(11)-C(12) | 118.7 (4) |
| C(11)-C(12) | 1.472 (7) | O(1)-C(12)-O(2) | 122.4 (4) |
| C(13)-C(16) | 1.372 (6) | O(1)-C(12)-C(11) | 124.7 (4) |
| C(14)-C(15) | 1.397 (6) | O(2)-C(12)-C(11) | 112.9 (4) |
| C(6)-N(5)-C(5) | 115.1 (4) | C(16)-C(13)-C(10) | 120.2 (5) |
| C(5)-N(2)-N(1) | 116.8 (4) | C(11)-C(14)-C(15) | 120.2 (4) |
| C(1)-N(1)-N(2) | 119.8 (4) | C(10)-C(15)-C(14) | 120.0 (4) |
| N(1)-C(1)-C(6) | 120.4 (4) | C(13)-C(16)-C(11) | 121.2 (4) |
| N(1)-C(1)-C(4) | 117.8 (4) | | |
| C(6)-C(1)-C(4) | 121.8 (4) | | |

TABLE 1-4

Anisotropic displacement parameters (Å$^2$ × 10$^3$) for lamotrigine:methylparaben co-crystal form I. The anisotropic displacement factor exponent takes the form: $-2\pi^2[h^2 a^{*2} U^{11} + \ldots + 2 h k a^* b^* U^{12}]$

| | U$^{11}$ | U$^{22}$ | U$^{33}$ | U$^{23}$ | U$^{13}$ | U$^{12}$ |
|---|---|---|---|---|---|---|
| Cl(1) | 33(1) | 33(1) | 30(1) | 6(1) | −2(1) | −13(1) |
| Cl(2) | 55(1) | 37(1) | 41(1) | 18(1) | −8(1) | −16(1) |
| N(5) | 22(2) | 27(2) | 24(3) | −1(2) | 12(2) | 1(2) |
| N(2) | 20(2) | 22(2) | 31(3) | 1(2) | 7(2) | −2(2) |
| N(1) | 16(2) | 28(3) | 27(3) | 3(2) | 7(2) | 3(2) |
| N(3) | 35(3) | 27(3) | 48(3) | −1(2) | 20(2) | −7(2) |
| C(1) | 12(3) | 24(3) | 18(3) | −2(2) | 0(2) | 5(2) |
| N(4) | 31(3) | 21(2) | 29(3) | −3(2) | 15(2) | 2(2) |
| C(2) | 28(3) | 19(3) | 27(3) | −6(2) | −1(2) | 8(2) |
| C(3) | 18(3) | 31(3) | 25(3) | −4(3) | 7(2) | 0(2) |
| C(4) | 20(3) | 16(3) | 28(3) | −2(2) | 12(2) | 5(2) |
| C(5) | 19(3) | 17(3) | 26(3) | 1(2) | 2(2) | 1(2) |
| C(6) | 19(3) | 25(3) | 21(3) | −2(2) | 0(2) | −2(2) |
| C(7) | 16(3) | 31(3) | 39(4) | −7(3) | 0(2) | −1(2) |
| C(8) | 27(3) | 21(3) | 39(4) | −9(2) | 6(3) | −6(2) |
| C(9) | 30(3) | 24(3) | 27(3) | −1(2) | 5(2) | −3(2) |
| O(2) | 25(2) | 25(2) | 30(2) | 1(2) | 17(2) | 3(2) |
| O(3) | 22(2) | 20(2) | 32(2) | 3(2) | 13(2) | −2(1) |
| O(1) | 30(2) | 21(2) | 36(2) | 2(2) | 15(2) | 5(2) |
| C(10) | 17(3) | 27(3) | 19(3) | −6(2) | 3(2) | 0(2) |
| C(11) | 18(3) | 28(3) | 19(3) | 0(2) | 6(2) | −7(2) |
| C(12) | 15(3) | 27(3) | 29(3) | −10(3) | 4(2) | −3(2) |
| C(13) | 23(3) | 26(3) | 34(3) | −4(3) | 5(2) | −1(2) |
| C(14) | 21(3) | 21(3) | 27(3) | −4(2) | 7(2) | 0(2) |
| C(15) | 17(3) | 23(3) | 30(3) | −8(3) | 10(2) | −4(2) |
| C(16) | 21(3) | 22(3) | 27(3) | −5(2) | 10(2) | 1(2) |
| C(17) | 34(3) | 32(3) | 28(3) | 8(3) | 14(2) | −7(2) |

TABLE 1-5

Hydrogen coordinates (×10⁴) and isotropic displacement
parameters (Å² × 10³) for
lamotrigine:methylparaben co-crystal form I.

|        | x     | y     | z     | U(eq) |
|--------|-------|-------|-------|-------|
| H(3N)  | 6880  | 5846  | 2129  | 43    |
| H(2N)  | 4833  | 6455  | 2493  | 43    |
| H(5N)  | 12561 | 7373  | 1020  | 32    |
| H(4N)  | 12624 | 8540  | 1057  | 32    |
| H(2)   | 12777 | 9859  | 2071  | 30    |
| H(7)   | 14200 | 11303 | 1771  | 34    |
| H(8)   | 12135 | 12065 | 1025  | 34    |
| H(3O)  | 1459  | 3126  | 2363  | 29    |
| H(13)  | 6642  | 2979  | 1540  | 33    |
| H(14)  | 1651  | 5666  | 1329  | 28    |
| H(15)  | 543   | 4504  | 1966  | 28    |
| H(16)  | 7696  | 4121  | 907   | 27    |
| H(17A) | 7138  | 6500  | -235  | 46    |
| H(17B) | 9987  | 6130  | -132  | 46    |
| H(17C) | 8852  | 6869  | 292   | 46    |

Example 2

Preparation of Lamotrigine:Methylparaben Co-Crystal Form I 58 mg of lamotrigine was dissolved in 2 ml of hot THF (tetrahydrofuran), 38 mg of methylparaben was added to the solution to form a single solution. The solution was then allowed to stand for several hours to effect the slow evaporation of solvent. The solids gathered were stored in screw cap vials for subsequent analysis.

Example 3

Preparation of Lamotrigine:Methylparaben Co-Crystal Form II 500 mg of lamotrigine was ground with 317 mg of methylparaben and 400 μL of methanol was added to the solid mixture. The solids gathered after grinding were stored in screw cap vials for subsequent analysis.

Example 4

Preparation of Lamotrigine:Methylparaben Co-Crystal Form II 1 g of lamotrigine and 598 mg of methylparaben was slurried in 5 ml of DI water overnight. The solids gathered after filtration were dried and stored in screw cap vials for subsequent analysis.

Example 5

Preparation of Lamotrigine:Methylparaben Co-Crystal Form II 75 mg of lamotrigine and 48 mg of methylparaben were recrystallized from melt at 115° C. for 2 hours, the melt was cooled down to room temperature. The solid phase was gathered and stored in screw cap vials for subsequent analysis.

The single crystal x-ray diffraction data for lamotrigine:methylparaben co-crystal form II is provided below in FIG. 3. The DSC thermogram is shown in FIG. 4. The infrared spectrum of the co-crystal is shown in FIG. 5.

TABLE 5-1

Crystal data and structure refinement for
lamotrigine:methylparaben co-crystal form II.

| Empirical formula | C17H15Cl2N5O3 |
|---|---|
| Formula weight | 408.24 |
| Temperature | 100(2) K |
| Wavelength | 0.71073 Å |
| Crystal system | Triclinic |
| Space group | P-1 |
| Unit cell dimensions | a = 8.625(3) Å    α = 106.884(8)°. |
|  | b = 11.043(4) Å   β = 102.178(9)°. |
|  | c = 11.717(5) Å   γ = 112.621(6)°. |
| Volume | 917.6(6) Å³ |
| Z | 2 |
| Density (calculated) | 1.478 Mg/m³ |
| Absorption coefficient | 0.383 mm⁻¹ |
| F(000) | 420 |
| Theta range for data collection | 1.95 to 24.76°. |
| Index ranges | -7 <= h <= 10, -13 <= k <= 12, |
|  | -13 <= l <= 10 |
| Reflections collected | 4601 |
| Independent reflections | 3092 [R(int) = 0.0456] |
| Completeness to theta = 24.76° | 98.5% |
| Refinement method | Full-matrix least-squares on F² |
| Data/restraints/parameters | 3092/0/263 |
| Goodness-of-fit on F² | 1.075 |
| Final R indices [I > 2sigma(I)] | R1 = 0.0927, wR2 = 0.2199 |
| R indices (all data) | R1 = 0.1259, wR2 = 0.2403 |
| Largest diff. peak and hole | 0.885 and -0.893 e · Å⁻³ |

TABLE 5-2

Atomic coordinates (×10⁴) and equivalent isotropic displacement
parameters (Å² × 10³) for lamotrigine:methylparaben
co-crystal form II. U(eq) is defined as one third of the trace of
the orthogonalized U$^{ij}$ tensor.

|        | x       | y       | z        | U(eq)  |
|--------|---------|---------|----------|--------|
| Cl(1A) | 3116(4) | 5719(3) | 4348(5)  | 118(2) |
| Cl(2A) | 4330(3) | 9005(3) | 5546(3)  | 58(1)  |
| Cl(2B) | 7418(5) | 9103(4) | 9636(3)  | 32(1)  |
| Cl(1B) | 6231(6) | 5862(4) | 8145(5)  | 51(1)  |
| C(1)   | 4100(11)| 6746(8) | 5705(12) | 110(5) |
| C(2)   | 4670(10)| 8179(7) | 6330(9)  | 72(3)  |
| C(3)   | 5647(8) | 8957(7) | 7607(9)  | 61(2)  |
| C(4)   | 6143(10)| 8263(8) | 8335(11) | 88(3)  |
| C(5)   | 5538(13)| 6746(11)| 7658(16) | 118(5) |
| C(6)   | 4529(14)| 6030(10)| 6399(18) | 132(7) |
| N(1)   | 5010(6) | 10896(5)| 8378(5)  | 42(1)  |
| N(2)   | 5466(6) | 12296(4)| 8906(4)  | 34(1)  |
| N(3)   | 8536(5) | 12974(4)| 9139(4)  | 26(1)  |
| N(4)   | 7614(6) | 14648(5)| 9766(5)  | 39(1)  |
| N(5)   | 9339(6) | 11214(5)| 8484(4)  | 35(1)  |
| O(1)   | 2899(4) | 3012(4) | 8500(3)  | 30(1)  |
| O(2)   | 243(5)  | 1267(4) | 2472(4)  | 38(1)  |
| O(3)   | -819(5) | 2768(4) | 3179(4)  | 38(1)  |
| C(7)   | 6239(7) | 10512(6)| 8238(6)  | 39(1)  |
| C(8)   | 8075(7) | 11584(5)| 8632(5)  | 27(1)  |
| C(9)   | 7188(6) | 13263(5)| 9252(5)  | 28(1)  |
| C(10)  | 2212(7) | 2737(5) | 7232(5)  | 29(1)  |
| C(11)  | 2489(7) | 1846(6) | 6292(5)  | 32(1)  |
| C(12)  | 1753(7) | 1610(5) | 5032(5)  | 31(1)  |
| C(13)  | 750(7)  | 2262(5) | 4694(5)  | 28(1)  |
| C(14)  | 445(7)  | 3121(6) | 5641(5)  | 33(1)  |
| C(15)  | 1172(7) | 3358(6) | 6909(5)  | 31(1)  |
| C(16)  | 55(7)   | 2036(6) | 3350(5)  | 30(1)  |
| C(17)  | -1491(8)| 2638(7) | 1873(6)  | 43(2)  |

TABLE 5-3

Bond lengths [Å] and angles [°] for
lamotrigine:methylparaben co-crystal form II.

| Cl(1A)—C(1) | 1.476(12) |
|---|---|
| Cl(2A)—C(2) | 1.530(10) |
| Cl(2B)—C(4) | 1.443(11) |

TABLE 5-3-continued

Bond lengths [Å] and angles [°] for lamotrigine:methylparaben co-crystal form II.

| | |
|---|---|
| Cl(1B)—C(5) | 1.504(10) |
| C(1)—C(2) | 1.364(10) |
| C(1)—C(6) | 1.378(19) |
| C(2)—C(3) | 1.360(12) |
| C(3)—C(4) | 1.406(12) |
| C(3)—C(7) | 1.479(8) |
| C(4)—C(5) | 1.445(13) |
| C(5)—C(6) | 1.346(19) |
| N(1)—C(7) | 1.307(7) |
| N(1)—N(2) | 1.343(6) |
| N(2)—C(9) | 1.336(6) |
| N(3)—C(8) | 1.330(6) |
| N(3)—C(9) | 1.340(6) |
| N(4)—C(9) | 1.333(7) |
| N(5)—C(8) | 1.328(6) |
| O(1)—C(10) | 1.371(6) |
| O(2)—C(16) | 1.214(6) |
| O(3)—C(16) | 1.328(6) |
| O(3)—C(17) | 1.460(7) |
| C(7)—C(8) | 1.434(7) |
| C(10)—C(15) | 1.378(7) |
| C(10)—C(11) | 1.379(7) |
| C(11)—C(12) | 1.380(8) |
| C(12)—C(13) | 1.387(7) |
| C(13)—C(14) | 1.380(7) |
| C(13)—C(16) | 1.469(7) |
| C(14)—C(15) | 1.387(8) |
| C(2)—C(1)—C(6) | 118.5(12) |
| C(2)—C(1)—Cl(1A) | 133.3(13) |
| C(6)—C(1)—Cl(1A) | 108.2(9) |
| C(3)—C(2)—C(1) | 124.0(10) |
| C(3)—C(2)—Cl(2A) | 117.1(6) |
| C(1)—C(2)—Cl(2A) | 118.6(10) |
| C(2)—C(3)—C(4) | 118.8(7) |
| C(2)—C(3)—C(7) | 121.9(7) |
| C(4)—C(3)—C(7) | 119.4(8) |
| C(3)—C(4)—Cl(2B) | 119.7(6) |
| C(3)—C(4)—C(5) | 116.6(10) |
| Cl(2B)—C(4)—C(5) | 123.0(9) |
| C(6)—C(5)—C(4) | 121.7(11) |
| C(6)—C(5)—Cl(1B) | 111.2(10) |
| C(4)—C(5)—Cl(1B) | 125.9(12) |
| C(5)—C(6)—C(1) | 120.4(9) |
| C(7)—N(1)—N(2) | 120.2(5) |
| C(9)—N(2)—N(1) | 117.9(4) |
| C(8)—N(3)—C(9) | 115.4(4) |
| C(16)—O(3)—C(17) | 116.0(4) |
| N(1)—C(7)—C(8) | 120.2(5) |
| N(1)—C(7)—C(3) | 117.8(5) |
| C(8)—C(7)—C(3) | 122.0(5) |
| N(5)—C(8)—N(3) | 118.8(5) |
| N(5)—C(8)—C(7) | 121.0(5) |
| N(3)—C(8)—C(7) | 120.1(5) |
| N(4)—C(9)—N(2) | 117.1(4) |
| N(4)—C(9)—N(3) | 116.7(4) |
| N(2)—C(9)—N(3) | 126.2(5) |
| O(1)—C(10)—C(15) | 117.5(5) |
| O(1)—C(10)—C(11) | 122.4(5) |
| C(15)—C(10)—C(11) | 120.1(5) |
| C(10)—C(11)—C(12) | 119.5(5) |
| C(11)—C(12)—C(13) | 121.2(5) |
| C(14)—C(13)—C(12) | 118.7(5) |
| C(14)—C(13)—C(16) | 121.7(5) |
| C(12)—C(13)—C(16) | 119.7(5) |
| C(13)—C(14)—C(15) | 120.5(5) |
| C(10)—C(15)—C(14) | 120.0(5) |
| O(2)—C(16)—O(3) | 122.4(5) |
| O(2)—C(16)—C(13) | 124.7(5) |
| O(3)—C(16)—C(13) | 112.9(4) |

TABLE 5-4

Anisotropic displacement parameters (Å$^2$ × 10$^3$) for lamotrigine:methylparaben co-crystal form II. The anisotropic displacement factor exponent takes the form: $-2\pi^2[h^2 a^{*2} U^{11} + \ldots + 2 h k a^* b^* U^{12}]$

| | $U^{11}$ | $U^{22}$ | $U^{33}$ | $U^{23}$ | $U^{13}$ | $U^{12}$ |
|---|---|---|---|---|---|---|
| Cl(1A) | 38(2) | 44(2) | 178(4) | −49(2) | 33(2) | 5(1) |
| Cl(2A) | 33(1) | 45(2) | 60(2) | −16(1) | 4(1) | 18(1) |
| Cl(2B) | 38(2) | 30(2) | 31(2) | 17(2) | 11(2) | 16(2) |
| Cl(1B) | 46(2) | 28(2) | 75(3) | 25(2) | 15(2) | 16(2) |
| C(1) | 59(5) | 24(4) | 197(12) | −15(6) | 82(7) | −4(4) |
| C(2) | 48(4) | 30(4) | 125(8) | 3(5) | 50(5) | 16(3) |
| C(3) | 29(3) | 28(3) | 128(7) | 20(4) | 44(4) | 16(3) |
| C(4) | 47(5) | 43(4) | 195(11) | 51(6) | 56(6) | 31(4) |
| C(5) | 56(6) | 57(6) | 290(17) | 89(9) | 95(8) | 44(5) |
| C(6) | 46(6) | 29(5) | 282(19) | 15(8) | 81(9) | 5(4) |
| N(1) | 24(2) | 27(3) | 67(4) | 8(2) | 17(2) | 12(2) |
| N(2) | 25(2) | 24(2) | 46(3) | 5(2) | 12(2) | 14(2) |
| N(3) | 23(2) | 22(2) | 30(2) | 4(2) | 9(2) | 12(2) |
| N(4) | 21(2) | 25(2) | 57(3) | 2(2) | 13(2) | 10(2) |
| N(5) | 25(2) | 24(2) | 48(3) | 5(2) | 14(2) | 13(2) |
| O(1) | 24(2) | 33(2) | 34(2) | 9(2) | 12(2) | 18(2) |
| O(2) | 45(2) | 38(2) | 32(2) | 7(2) | 17(2) | 26(2) |
| O(3) | 45(2) | 40(2) | 36(2) | 14(2) | 16(2) | 29(2) |
| C(7) | 32(3) | 29(3) | 59(4) | 13(3) | 22(3) | 18(3) |
| C(8) | 25(3) | 28(3) | 30(3) | 11(2) | 10(2) | 14(2) |
| C(9) | 23(3) | 28(3) | 29(3) | 6(2) | 8(2) | 14(2) |
| C(10) | 23(3) | 23(3) | 37(3) | 8(2) | 13(2) | 9(2) |
| C(11) | 29(3) | 32(3) | 40(3) | 10(3) | 14(2) | 21(2) |
| C(12) | 34(3) | 26(3) | 28(3) | 2(2) | 14(2) | 16(2) |
| C(13) | 26(3) | 24(3) | 34(3) | 8(2) | 13(2) | 13(2) |
| C(14) | 29(3) | 31(3) | 43(4) | 13(3) | 16(2) | 20(2) |
| C(15) | 28(3) | 29(3) | 33(3) | 3(2) | 12(2) | 17(2) |
| C(16) | 26(3) | 27(3) | 38(3) | 11(2) | 16(2) | 13(2) |
| C(17) | 50(4) | 50(4) | 32(3) | 18(3) | 10(3) | 30(3) |

TABLE 5-5

Hydrogen coordinates (×10$^4$) and isotropic displacement parameters (Å$^2$ × 10$^3$) for lamotrigine:methylparaben co-crystal form II.

| | x | y | z | U(eq) |
|---|---|---|---|---|
| H(3N) | 8664 | 15427 | 9984 | 46 |
| H(4N) | 6851 | 14929 | 10033 | 46 |
| H(5N) | 9002 | 10205 | 8035 | 41 |
| H(6N) | 10490 | 11951 | 8733 | 41 |
| H(1O) | 3773 | 2725 | 8693 | 36 |
| H(11) | 3181 | 1398 | 6510 | 38 |
| H(12) | 1936 | 989 | 4384 | 37 |
| H(14) | −268 | 3554 | 5422 | 39 |
| H(15) | 952 | 3949 | 7555 | 37 |

Example 6

Preparation of Lamotrigine:Nicotinamide Co-Crystal 714 mg lamotrigine and 350 mg of nicotinamide were recrystallized from melt at 125° C. for 2 hours and cooled down to room temperature. The solids gathered were stored in screw cap vials for subsequent analysis. The PXRD diffractogram is shown in FIG. 7. The DSC thermogram is shown in FIG. 8. The infrared spectrum of the co-crystal is shown in FIG. 9.

Example 7

Preparation of Lamotrigine Saccharinate 514 mg of lamotrigine was dissolved in 50 ml of acetonitrile, 610 mg of saccharin was dissolved in 40 ml of acetonitrile and both solutions were combined to form a single solution. The solution was then allowed to stand for several hours to effect the slow evaporation of solvent. The solids gathered were stored in screw cap vials for subsequent analysis.

The single crystal x-ray diffraction data for lamotrigine saccharinate is provided below. The PXRD diffractogram is shown in FIG. 10. The DSC thermogram is shown in FIG. 11. The infrared spectrum is shown in FIG. 12.

TABLE 7-1

Crystal data and structure refinement for lamotrigine saccharinate.

| | |
|---|---|
| Empirical formula | C16H12C12N6O3S |
| Formula weight | 439.28 |
| Temperature | 100(2) K |
| Wavelength | 0.71073 Å |
| Crystal system | Monoclinic |
| Space group | P2(1)/c |
| Unit cell dimensions | a = 18.440(13) Å   α = 90°. |
| | b = 6.949(5) Å   β = 108.20(3)°. |
| | c = 14.652(18) Å   γ = 90°. |
| Volume | 1783(3) Å$^3$ |
| Z | 4 |
| Density (calculated) | 1.636 Mg/m$^3$ |
| Absorption coefficient | 0.515 mm$^{-1}$ |
| F(000) | 896 |
| Crystal size | 0.08 × 0.02 × 0.02 mm$^3$ |
| Theta range for data collection | 1.16 to 28.33°. |
| Index ranges | −21 <= h <= 23, −8 <= k <= 6, |
| | −19 <= l <= 7 |
| Reflections collected | 4895 |
| Independent reflections | 3698 [R(int) = 0.0198] |
| Completeness to theta = 25.00° | 94.1% |
| Max. and min. transmission | 0.9898 and 0.9600 |
| Refinement method | Full-matrix least-squares on F$^2$ |
| Data/restraints/parameters | 3698/0/253 |
| Goodness-of-fit on F$^2$ | 1.100 |
| Final R indices [I > 2sigma(I)] | R1 = 0.0455, wR2 = 0.1232 |
| R indices (all data) | R1 = 0.0512, wR2 = 0.1323 |
| Largest diff. peak and hole | 1.027 and −0.504 e · Å$^{-3}$ |

TABLE 7-2

Atomic coordinates (×10$^4$) and equivalent isotropic displacement parameters (Å$^2$ × 10$^3$) for lamotrigine saccharinate. U(eq) is defined as one third of the trace of the orthogonalized U$^{ij}$ tensor.

| | x | y | z | U(eq) |
|---|---|---|---|---|
| S(1) | 2237(1) | 9112(1) | 2523(1) | 16(1) |
| Cl(1) | 3745(1) | 11921(1) | 4120(1) | 19(1) |
| Cl(2) | 5494(1) | 12289(1) | 4489(1) | 18(1) |
| O(1) | 515(1) | 7352(2) | 740(1) | 21(1) |
| O(2) | 2888(1) | 9798(2) | 2277(1) | 20(1) |
| O(3) | 2401(1) | 8306(3) | 3467(1) | 24(1) |
| N(5) | 998(1) | 11112(3) | 5101(1) | 19(1) |
| N(2) | 2249(1) | 10585(3) | 5940(1) | 17(1) |
| N(1) | 1878(1) | 13391(3) | 5027(1) | 15(1) |
| N(3) | 3005(1) | 10936(3) | 6151(1) | 16(1) |
| N(4) | 2820(1) | 15467(3) | 4967(1) | 19(1) |
| C(4) | 5591(1) | 13162(3) | 6309(2) | 18(1) |
| C(8) | 2615(1) | 13825(3) | 5259(1) | 15(1) |
| C(16) | 1018(1) | 8265(3) | 1344(2) | 17(1) |
| C(10) | 876(1) | 10188(3) | 1699(2) | 16(1) |
| C(9) | 1708(1) | 11711(3) | 5350(1) | 15(1) |
| C(6) | 4506(1) | 13295(3) | 6885(2) | 17(1) |
| N(6) | 1735(1) | 7631(3) | 1730(1) | 18(1) |
| C(15) | 1531(1) | 10904(3) | 2354(2) | 15(1) |
| C(1) | 4024(1) | 12824(3) | 5982(2) | 14(1) |
| C(2) | 4331(1) | 12562(3) | 5237(1) | 14(1) |
| C(3) | 5113(1) | 12707(3) | 5407(2) | 15(1) |
| C(11) | 213(1) | 11266(3) | 1438(2) | 19(1) |
| C(7) | 3195(1) | 12503(3) | 5809(1) | 14(1) |
| C(5) | 5287(1) | 13464(4) | 7040(2) | 19(1) |
| C(12) | 235(2) | 13071(4) | 1849(2) | 25(1) |
| C(13) | 905(1) | 13793(4) | 2491(2) | 24(1) |
| C(14) | 1569(1) | 12698(3) | 2755(2) | 21(1) |

TABLE 7-3

Bond lengths [Å] and angles [°] for lamotrigine saccharinate.

| | |
|---|---|
| S(1)—O(3) | 1.434(2) |
| S(1)—O(2) | 1.4367(19) |
| S(1)—N(6) | 1.611(2) |
| S(1)—C(15) | 1.763(2) |
| Cl(1)—C(2) | 1.715(3) |
| Cl(2)—C(3) | 1.725(3) |
| O(1)—C(16) | 1.238(3) |
| N(5)—C(9) | 1.312(3) |
| N(5)—H(5A) | 0.8800 |
| N(5)—H(5B) | 0.8800 |
| N(2)—C(9) | 1.349(3) |
| N(2)—N(3) | 1.352(3) |
| N(2)—H(2) | 0.8800 |
| N(1)—C(8) | 1.327(3) |
| N(1)—C(9) | 1.333(3) |
| N(3)—C(7) | 1.293(3) |
| N(4)—C(8) | 1.315(3) |
| N(4)—H(4A) | 0.8800 |
| N(4)—H(4B) | 0.8800 |
| C(4)—C(5) | 1.373(3) |
| C(4)—C(3) | 1.377(3) |
| C(4)—H(4) | 0.9500 |
| C(8)—C(7) | 1.449(3) |
| C(16)—N(6) | 1.340(3) |
| C(16)—C(10) | 1.487(3) |
| C(10)—C(15) | 1.379(3) |
| C(10)—C(11) | 1.383(3) |
| C(6)—C(1) | 1.384(3) |
| C(6)—C(5) | 1.391(3) |
| C(6)—H(6) | 0.9500 |
| C(15)—C(14) | 1.370(3) |
| C(1)—C(2) | 1.390(3) |
| C(1)—C(7) | 1.486(3) |
| C(2)—C(3) | 1.388(3) |
| C(11)—C(12) | 1.386(4) |
| C(11)—H(11) | 0.9500 |
| C(5)—H(5) | 0.9500 |
| C(12)—C(13) | 1.392(4) |
| C(12)—H(12) | 0.9500 |
| C(13)—C(14) | 1.390(3) |
| C(13)—H(13) | 0.9500 |
| C(14)—H(14) | 0.9500 |
| O(3)—S(1)—O(2) | 115.51(10) |
| O(3)—S(1)—N(6) | 110.27(12) |
| O(2)—S(1)—N(6) | 111.53(12) |
| O(3)—S(1)—C(15) | 109.60(11) |
| O(2)—S(1)—C(15) | 111.64(11) |
| N(6)—S(1)—C(15) | 96.71(11) |
| C(9)—N(5)—H(5A) | 120.0 |
| C(9)—N(5)—H(5B) | 120.0 |
| H(5A)—N(5)—H(5B) | 120.0 |
| C(9)—N(2)—N(3) | 123.09(19) |
| C(9)—N(2)—H(2) | 118.5 |
| N(3)—N(2)—H(2) | 118.5 |
| C(8)—N(1)—C(9) | 116.35(19) |
| C(7)—N(3)—N(2) | 116.61(18) |
| C(8)—N(4)—H(4A) | 120.0 |
| C(8)—N(4)—H(4B) | 120.0 |
| H(4A)—N(4)—H(4B) | 120.0 |
| C(5)—C(4)—C(3) | 119.3(2) |
| C(5)—C(4)—H(4) | 120.3 |
| C(3)—C(4)—H(4) | 120.3 |
| N(4)—C(8)—N(1) | 119.3(2) |
| N(4)—C(8)—C(7) | 119.6(2) |
| N(1)—C(8)—C(7) | 121.1(2) |
| O(1)—C(16)—N(6) | 123.6(2) |
| O(1)—C(16)—C(10) | 122.4(2) |
| N(6)—C(16)—C(10) | 113.98(19) |
| C(15)—C(10)—C(11) | 120.2(2) |
| C(15)—C(10)—C(16) | 110.88(19) |
| C(11)—C(10)—C(16) | 128.9(2) |
| N(5)—C(9)—N(1) | 120.3(2) |
| N(5)—C(9)—N(2) | 117.9(2) |
| N(1)—C(9)—N(2) | 121.7(2) |
| C(1)—C(6)—C(5) | 120.0(2) |
| C(1)—C(6)—H(6) | 120.0 |
| C(5)—C(6)—H(6) | 120.0 |
| C(16)—N(6)—S(1) | 111.30(16) |

TABLE 7-3-continued

Bond lengths [Å] and angles [°] for lamotrigine saccharinate.

| | |
|---|---|
| C(14)—C(15)—C(10) | 122.9(2) |
| C(14)—C(15)—S(1) | 130.20(18) |
| C(10)—C(15)—S(1) | 106.91(17) |
| C(6)—C(1)—C(2) | 118.9(2) |
| C(6)—C(1)—C(7) | 121.3(2) |
| C(2)—C(1)—C(7) | 119.74(19) |
| C(3)—C(2)—C(1) | 120.33(19) |
| C(3)—C(2)—Cl(1) | 120.02(17) |
| C(1)—C(2)—Cl(1) | 119.55(18) |
| C(4)—C(3)—C(2) | 120.5(2) |
| C(4)—C(3)—Cl(2) | 119.51(19) |
| C(2)—C(3)—Cl(2) | 120.03(17) |
| C(10)—C(11)—C(12) | 117.8(2) |
| C(10)—C(11)—H(11) | 121.1 |
| C(12)—C(11)—H(11) | 121.1 |
| N(3)—C(7)—C(8) | 120.5(2) |
| N(3)—C(7)—C(1) | 116.68(19) |
| C(8)—C(7)—C(1) | 122.8(2) |
| C(4)—C(5)—C(6) | 120.9(2) |
| C(4)—C(5)—H(5) | 119.5 |
| C(6)—C(5)—H(5) | 119.5 |
| C(11)—C(12)—C(13) | 121.3(2) |
| C(11)—C(12)—H(12) | 119.4 |
| C(13)—C(12)—H(12) | 119.4 |
| C(14)—C(13)—C(12) | 120.6(2) |
| C(14)—C(13)—H(13) | 119.7 |
| C(12)—C(13)—H(13) | 119.7 |
| C(15)—C(14)—C(13) | 117.1(2) |
| C(15)—C(14)—H(14) | 121.4 |
| C(13)—C(14)—H(14) | 121.4 |

TABLE 7-4

Anisotropic displacement parameters (Å$^2$ × 10$^3$) for lamotrigine saccharinate. The anisotropic displacement factor exponent takes the form: $-2\pi^2[h^2 a^{*2} U^{11} + \ldots + 2 h k a^* b^* U^{12}]$

| | U$^{11}$ | U$^{22}$ | U$^{33}$ | U$^{23}$ | U$^{13}$ | U$^{12}$ |
|---|---|---|---|---|---|---|
| S(1) | 12(1) | 16(1) | 16(1) | 0(1) | 0(1) | 0(1) |
| Cl(1) | 12(1) | 26(1) | 16(1) | −4(1) | 1(1) | −4(1) |
| Cl(2) | 13(1) | 20(1) | 21(1) | −2(1) | 7(1) | −2(1) |
| O(1) | 12(1) | 21(1) | 26(1) | −5(1) | 0(1) | −1(1) |
| O(2) | 12(1) | 25(1) | 19(1) | −1(1) | 1(1) | −3(1) |
| O(3) | 22(1) | 26(1) | 20(1) | 7(1) | 1(1) | −2(1) |
| N(5) | 9(1) | 18(1) | 26(1) | 5(1) | 1(1) | 0(1) |
| N(2) | 9(1) | 19(1) | 22(1) | 5(1) | 3(1) | −1(1) |
| N(1) | 11(1) | 18(1) | 16(1) | 1(1) | 2(1) | 1(1) |
| N(3) | 8(1) | 20(1) | 19(1) | 0(1) | 2(1) | −1(1) |
| N(4) | 11(1) | 20(1) | 23(1) | 6(1) | 2(1) | 0(1) |
| C(4) | 10(1) | 18(1) | 22(1) | 3(1) | 2(1) | −1(1) |
| C(8) | 12(1) | 19(1) | 14(1) | −2(1) | 3(1) | −1(1) |
| C(16) | 13(1) | 18(1) | 20(1) | 1(1) | 3(1) | −1(1) |
| C(10) | 15(1) | 17(1) | 17(1) | 3(1) | 6(1) | 0(1) |
| C(9) | 11(1) | 18(1) | 16(1) | −2(1) | 4(1) | 0(1) |
| C(6) | 15(1) | 20(1) | 16(1) | 2(1) | 4(1) | 0(1) |
| N(6) | 12(1) | 16(1) | 22(1) | −4(1) | −2(1) | 0(1) |
| C(15) | 14(1) | 17(1) | 16(1) | 3(1) | 6(1) | 3(1) |
| C(1) | 9(1) | 13(1) | 18(1) | 2(1) | 2(1) | −1(1) |
| C(2) | 12(1) | 11(1) | 15(1) | 1(1) | 0(1) | −2(1) |
| C(3) | 13(1) | 15(1) | 17(1) | 0(1) | 5(1) | 0(1) |
| C(11) | 15(1) | 24(1) | 19(1) | 5(1) | 6(1) | 4(1) |
| C(7) | 12(1) | 17(1) | 14(1) | −1(1) | 3(1) | 0(1) |
| C(5) | 13(1) | 23(1) | 17(1) | 1(1) | −1(1) | −3(1) |
| C(12) | 23(1) | 26(1) | 27(1) | 5(1) | 11(1) | 10(1) |
| C(13) | 31(1) | 20(1) | 24(1) | −1(1) | 13(1) | 4(1) |
| C(14) | 23(1) | 21(1) | 18(1) | −2(1) | 6(1) | 0(1) |

TABLE 7-5

Hydrogen coordinates (×10$^4$) and isotropic displacement parameters (Å$^2$ × 10$^3$) for lamotrigine saccharinate.

| | x | y | z | U(eq) |
|---|---|---|---|---|
| H(5A) | 632 | 11820 | 4719 | 23 |
| H(5B) | 888 | 10003 | 5315 | 23 |
| H(2) | 2104 | 9573 | 6200 | 20 |
| H(4A) | 2470 | 16264 | 4621 | 23 |
| H(4B) | 3307 | 15768 | 5116 | 23 |
| H(4) | 6126 | 13265 | 6423 | 21 |
| H(6) | 4304 | 13504 | 7399 | 21 |
| H(11) | −244 | 10786 | 991 | 23 |
| H(5) | 5615 | 13792 | 7662 | 23 |
| H(12) | −216 | 13830 | 1690 | 29 |
| H(13) | 909 | 15047 | 2751 | 29 |
| H(14) | 2029 | 13172 | 3195 | 25 |

Example 8

Preparation of Lamotrigine Adipate 16 mg of lamotrigine was dissolved in 2 ml of methanol, 11 mg of adipic acid was added to the solution to form a single solution. The solution was then allowed to stand for several hours to effect the slow evaporation of solvent. The solids gathered were stored in screw cap vials for subsequent analysis.

The single crystal x-ray diffraction data for lamotrigine adipate is provided below. The PXRD diffractogram is shown in FIG. 14. The infrared spectrum is shown in FIG. 15.

TABLE 8-1

Crystal data and structure refinement for lamotrigine adipate.

| | |
|---|---|
| Empirical formula | C12H12Cl2N5O2 |
| Formula weight | 329.17 |
| Temperature | 100(2) K |
| Wavelength | 0.71073 Å |
| Crystal system | Monoclinic |
| Space group | P2(1)/c |
| Unit cell dimensions | a = 13.068(3) Å    α = 90°. |
| | b = 7.4983(18) Å   β = 96.755(4)°. |
| | c = 14.069(3) Å    γ = 90°. |
| Volume | 1369.0(6) Å$^3$ |
| Z | 4 |
| Density (calculated) | 1.597 Mg/m$^3$ |
| Absorption coefficient | 0.486 mm$^{-1}$ |
| F(000) | 676 |
| Crystal size | 0.6 × 0.4 × 0.2 mm$^3$ |
| Theta range for data collection | 1.57 to 28.35°. |
| Index ranges | −16 <= h <= 17, −9 <= k <= 9, −13 <= l <= 18 |
| Reflections collected | 7865 |
| Independent reflections | 3144 [R(int) = 0.0197] |
| Completeness to theta = 28.35° | 92.1% |
| Absorption correction | None |
| Refinement method | Full-matrix least-squares on F$^2$ |
| Data/restraints/parameters | 3144/0/190 |
| Goodness-of-fit on F$^2$ | 1.037 |
| Final R indices [I > 2sigma(I)] | R1 = 0.0353, wR2 = 0.0956 |
| R indices (all data) | R1 = 0.0393, wR2 = 0.0984 |
| Largest diff. peak and hole | 0.429 and −0.281 e · Å$^{-3}$ |

TABLE 8-2

Atomic coordinates (×10⁴) and equivalent isotropic displacement parameters (Å² × 10³) for lamotrigine adipate. U(eq) is defined as one third of the trace of the orthogonalized $U^{ij}$ tensor.

|       | x        | y        | z         | U(eq)  |
|-------|----------|----------|-----------|--------|
| Cl(1) | 10132(1) | 2561(1)  | 3338(1)   | 17(1)  |
| Cl(2) | 11943(1) | −147(1)  | 3906(1)   | 23(1)  |
| O(1)  | 4099(1)  | 2426(1)  | 11230(1)  | 15(1)  |
| O(2)  | 3232(1)  | 790(1)   | 10094(1)  | 15(1)  |
| N(1)  | 7513(1)  | −538(2)  | 1819(1)   | 16(1)  |
| N(2)  | 6492(1)  | 1776(2)  | 2181(1)   | 13(1)  |
| N(3)  | 5577(1)  | 4246(2)  | 2550(1)   | 16(1)  |
| N(4)  | 7044(1)  | 3506(2)  | 3546(1)   | 14(1)  |
| N(5)  | 7840(1)  | 2415(2)  | 3834(1)   | 14(1)  |
| C(1)  | 3925(1)  | 1926(2)  | 10381(1)  | 13(1)  |
| C(2)  | 9876(1)  | 389(2)   | 3647(1)   | 14(1)  |
| C(3)  | 6375(1)  | 3167(2)  | 2758(1)   | 12(1)  |
| C(4)  | 7307(1)  | 738(2)   | 2415(1)   | 13(1)  |
| C(5)  | 7978(1)  | 1042(2)  | 3305(1)   | 13(1)  |
| C(6)  | 10675(1) | −801(2)  | 3910(1)   | 16(1)  |
| C(7)  | 9450(1)  | −3101(2) | 4130(1)   | 18(1)  |
| C(8)  | 8851(1)  | −177(2)  | 3613(1)   | 13(1)  |
| C(9)  | 8643(1)  | −1937(2) | 3855(1)   | 16(1)  |
| C(10) | 5291(1)  | 4141(2)  | 9927(1)   | 15(1)  |
| C(11) | 10463(1) | −2544(2) | 4155(1)   | 18(1)  |
| C(12) | 4575(1)  | 2594(2)  | 9627(1)   | 17(1)  |

TABLE 8-3

Bond lengths [Å] and angles [°] for lamotrigine adipate.

| | |
|---|---|
| Cl(1)—C(2)     | 1.7286(16) |
| Cl(2)—C(6)     | 1.7286(17) |
| O(1)—C(1)      | 1.247(2)   |
| O(2)—C(1)      | 1.2740(19) |
| N(1)—C(4)      | 1.320(2)   |
| N(2)—C(4)      | 1.329(2)   |
| N(2)—C(3)      | 1.342(2)   |
| N(3)—C(3)      | 1.324(2)   |
| N(4)—N(5)      | 1.3481(18) |
| N(4)—C(3)      | 1.352(2)   |
| N(5)—C(5)      | 1.295(2)   |
| C(1)—C(12)     | 1.519(2)   |
| C(2)—C(6)      | 1.390(2)   |
| C(2)—C(8)      | 1.401(2)   |
| C(4)—C(5)      | 1.460(2)   |
| C(5)—C(8)      | 1.486(2)   |
| C(6)—C(11)     | 1.388(2)   |
| C(7)—C(11)     | 1.384(2)   |
| C(7)—C(9)      | 1.388(2)   |
| C(8)—C(9)      | 1.397(2)   |
| C(10)—C(12)    | 1.519(2)   |
| C(10)—C(10)#1  | 1.522(3)   |
| C(4)—N(2)—C(3) | 116.78(13) |
| N(5)—N(4)—C(3) | 122.31(13) |
| C(5)—N(5)—N(4) | 117.64(13) |
| O(1)—C(1)—O(2) | 123.13(14) |
| O(1)—C(1)—C(12)| 121.08(14) |
| O(2)—C(1)—C(12)| 115.74(13) |
| C(6)—C(2)—C(8) | 120.01(15) |
| C(6)—C(2)—Cl(1)| 120.65(12) |
| C(8)—C(2)—Cl(1)| 119.33(12) |
| N(3)—C(3)—N(2) | 118.93(14) |
| N(3)—C(3)—N(4) | 118.86(14) |
| N(2)—C(3)—N(4) | 122.21(14) |
| N(1)—C(4)—N(2) | 118.97(14) |
| N(1)—C(4)—C(5) | 120.75(14) |
| N(2)—C(4)—C(5) | 120.26(14) |
| N(5)—C(5)—C(4) | 120.47(14) |
| N(5)—C(5)—C(8) | 118.39(14) |
| C(4)—C(5)—C(8) | 121.11(13) |
| C(2)—C(6)—C(11)| 120.33(15) |
| C(2)—C(6)—Cl(2)| 120.52(13) |
| C(11)—C(6)—Cl(2)| 119.14(12) |
| C(11)—C(7)—C(9)| 120.67(15) |
| C(9)—C(8)—C(2) | 119.33(14) |

TABLE 8-3-continued

Bond lengths [Å] and angles [°] for lamotrigine adipate.

| | |
|---|---|
| C(9)—C(8)—C(5)       | 119.21(14) |
| C(2)—C(8)—C(5)       | 121.45(14) |
| C(7)—C(9)—C(8)       | 119.94(15) |
| C(12)—C(10)—C(10)#1  | 112.49(16) |
| C(7)—C(11)—C(6)      | 119.72(15) |
| C(1)—C(12)—C(10)     | 115.72(13) |

Symmetry transformations used to generate equivalent atoms:
1 −x + 1, −y + 1, −z + 2

TABLE 8-4

Anisotropic displacement parameters (Å² × 10³) for lamotrigine adipate. The anisotropic displacement factor exponent takes the form: $-2\pi^2[h^2 a^{*2} U^{11} + \ldots + 2 h k a^* b^* U^{12}]$

|       | $U^{11}$ | $U^{22}$ | $U^{33}$ | $U^{23}$ | $U^{13}$ | $U^{12}$ |
|-------|-------|-------|-------|-------|-------|-------|
| Cl(1) | 16(1) | 16(1) | 18(1) | 2(1)  | 4(1)  | −2(1) |
| Cl(2) | 12(1) | 30(1) | 26(1) | −1(1) | 2(1)  | 2(1)  |
| O(1)  | 18(1) | 16(1) | 11(1) | 1(1)  | 1(1)  | −3(1) |
| O(2)  | 19(1) | 15(1) | 12(1) | 1(1)  | 1(1)  | −4(1) |
| N(1)  | 16(1) | 18(1) | 13(1) | −3(1) | −1(1) | 4(1)  |
| N(2)  | 13(1) | 14(1) | 12(1) | −1(1) | 1(1)  | 0(1)  |
| N(3)  | 16(1) | 15(1) | 14(1) | −3(1) | −2(1) | 2(1)  |
| N(4)  | 14(1) | 14(1) | 13(1) | −4(1) | 1(1)  | 3(1)  |
| N(5)  | 13(1) | 16(1) | 14(1) | 0(1)  | 2(1)  | 1(1)  |
| C(1)  | 14(1) | 11(1) | 14(1) | 3(1)  | 2(1)  | 1(1)  |
| C(2)  | 17(1) | 14(1) | 10(1) | −1(1) | 3(1)  | 0(1)  |
| C(3)  | 13(1) | 13(1) | 12(1) | 1(1)  | 3(1)  | −2(1) |
| C(4)  | 13(1) | 14(1) | 12(1) | 0(1)  | 2(1)  | −1(1) |
| C(5)  | 12(1) | 14(1) | 12(1) | 0(1)  | 2(1)  | 0(1)  |
| C(6)  | 12(1) | 23(1) | 12(1) | −3(1) | 0(1)  | 1(1)  |
| C(7)  | 24(1) | 16(1) | 14(1) | 0(1)  | 3(1)  | 2(1)  |
| C(8)  | 14(1) | 16(1) | 9(1)  | −2(1) | 1(1)  | 1(1)  |
| C(9)  | 19(1) | 16(1) | 13(1) | −1(1) | 4(1)  | 1(1)  |
| C(10) | 15(1) | 15(1) | 16(1) | 2(1)  | 5(1)  | −1(1) |
| C(11) | 19(1) | 20(1) | 13(1) | −1(1) | 0(1)  | 7(1)  |
| C(12) | 22(1) | 15(1) | 16(1) | −2(1) | 8(1)  | −3(1) |

TABLE 8-5

Hydrogen coordinates (×10⁴) and isotropic displacement parameters (Å² × 10³) for lamotrigine adipate.

|        | x     | y     | z     | U(eq) |
|--------|-------|-------|-------|-------|
| H(1A)  | 7162  | −548  | 1212  | 19    |
| H(1B)  | 8060  | −1324 | 1999  | 19    |
| H(3A)  | 5139  | 3948  | 2089  | 19    |
| H(3B)  | 5518  | 5199  | 2917  | 19    |
| H(4A)  | 6969  | 4326  | 3977  | 16    |
| H(7)   | 9306  | −4291 | 4303  | 21    |
| H(9)   | 7951  | −2336 | 3831  | 19    |
| H(10A) | 5756  | 4339  | 9430  | 18    |
| H(10B) | 5722  | 3829  | 10530 | 18    |
| H(11)  | 11010 | −3351 | 4340  | 21    |
| H(12A) | 4106  | 2962  | 9056  | 21    |
| H(12B) | 4995  | 1588  | 9433  | 21    |

Example 9

Preparation of Lamotrigine Malate 20 mg of lamotrigine was dissolved in 2 ml of methanol, 12 mg of malic acid sodium salt was added to the solution to form a single solution. The solution was then allowed to stand for several hours to effect the slow evaporation of solvent. The solids gathered were stored in screw cap vials for subsequent analysis.

The single crystal x-ray diffraction data for lamotrigine malate is provided below. The PXRD diffractogram is shown in FIG. 17. The infrared spectrum is shown in FIG. 18.

TABLE 9-1

Crystal data and structure refinement for lamotrigine malate

| | |
|---|---|
| Empirical formula | C11H9Cl2N6O2.5 |
| Formula weight | 336.14 |
| Temperature | 293(2) K |
| Wavelength | 0.71073 Å |
| Crystal system | Monoclinic |
| Space group | P2(1)/c |
| Unit cell dimensions | a = 12.686(6) Å  α = 90°. |
| | b = 10.146(5) Å  β = 107.364(8)°. |
| | c = 10.720(5) Å  γ = 90°. |
| Volume | 1317.0(11) Å$^3$ |
| Z | 4 |
| Density (calculated) | 1.695 Mg/m$^3$ |
| Absorption coefficient | 0.512 mm$^{-1}$ |
| F(000) | 684 |
| Theta range for data collection | 2.62 to 28.29°. |
| Index ranges | −16 <= h <= 15, −10 <= k <= 13, −14 <= l <= 14 |
| Reflections collected | 7297 |
| Independent reflections | 3004 [R(int) = 0.1034] |
| Completeness to theta = 28.29° | 91.6% |
| Refinement method | Full-matrix least-squares on F$^2$ |
| Data/restraints/parameters | 3004/0/194 |
| Goodness-of-fit on F$^2$ | 1.033 |
| Final R indices [I > 2sigma(I)] | R1 = 0.1098, wR2 = 0.2425 |
| R indices (all data) | R1 = 0.1991, wR2 = 0.2797 |
| Largest diff. peak and hole | 0.870 and −0.526 e · Å$^{-3}$ |

TABLE 9-2

Atomic coordinates (×10$^4$) and equivalent isotropic displacement parameters (Å$^2$ × 10$^3$) for lamotrigine malate. U(eq) is defined as one third of the trace of the orthogonalized U$^{ij}$ tensor.

| | x | y | z | U(eq) |
|---|---|---|---|---|
| Cl(1) | 6329(2) | 10354(2) | 6057(2) | 39(1) |
| Cl(2) | 8735(2) | 10126(2) | 5853(2) | 46(1) |
| N(1) | 3728(4) | 7743(6) | 6601(6) | 25(1) |
| N(2) | 4756(5) | 7587(7) | 6492(6) | 28(2) |
| N(3) | 4312(5) | 8962(6) | 8534(7) | 31(2) |
| N(4) | 2487(5) | 8487(6) | 7571(7) | 31(2) |
| N(5) | 6156(6) | 9346(7) | 9382(7) | 44(2) |
| C(1) | 7135(6) | 9012(8) | 6688(8) | 31(2) |
| C(2) | 8204(7) | 8896(9) | 6590(9) | 39(2) |
| C(3) | 8820(7) | 7828(9) | 7086(10) | 48(2) |
| C(4) | 8404(7) | 6835(10) | 7705(10) | 52(3) |
| C(5) | 7332(7) | 6923(9) | 7834(10) | 46(2) |
| C(6) | 6691(6) | 8028(8) | 7280(7) | 29(2) |
| C(7) | 5556(6) | 8149(8) | 7409(7) | 28(2) |
| C(8) | 5336(7) | 8838(8) | 8474(8) | 34(2) |
| C(9) | 3514(6) | 8408(7) | 7583(8) | 29(2) |
| O(1) | 7853(4) | 1227(6) | 9929(5) | 41(2) |
| O(2) | 9185(4) | 2184(6) | 9299(6) | 44(2) |
| O(3) | 8726(8) | −961(10) | 9818(10) | 28(2) |
| C(10) | 8802(6) | 1266(9) | 9772(8) | 38(2) |
| C(11) | 9505(6) | 36(8) | 10248(8) | 35(2) |

TABLE 9-3

Bond lengths [Å] and angles [°] for lamotrigine malate.

| | |
|---|---|
| Cl(1)—C(1) | 1.716(8) |
| Cl(2)—C(2) | 1.718(9) |
| N(1)—C(9) | 1.345(9) |
| N(1)—N(2) | 1.353(8) |
| N(2)—C(7) | 1.314(9) |
| N(3)—C(9) | 1.328(10) |
| N(3)—C(8) | 1.325(10) |
| N(4)—C(9) | 1.302(9) |
| N(5)—C(8) | 1.300(10) |
| C(1)—C(6) | 1.389(11) |
| C(1)—C(2) | 1.397(11) |
| C(2)—C(3) | 1.349(12) |
| C(3)—C(4) | 1.393(13) |
| C(4)—C(5) | 1.410(12) |
| C(5)—C(6) | 1.408(12) |
| C(6)—C(7) | 1.493(10) |
| C(7)—C(8) | 1.435(11) |
| O(1)—C(10) | 1.266(9) |
| O(2)—C(10) | 1.228(8) |
| O(3)—C(11) | 1.393(12) |
| C(10)—C(11) | 1.530(12) |
| C(11)—C(11)#1 | 1.506(16) |
| C(9)—N(1)—N(2) | 123.4(6) |
| C(7)—N(2)—N(1) | 115.7(6) |
| C(9)—N(3)—C(8) | 117.2(7) |
| C(6)—C(1)—C(2) | 120.6(8) |
| C(6)—C(1)—Cl(1) | 118.4(6) |
| C(2)—C(1)—Cl(1) | 121.0(6) |
| C(3)—C(2)—C(1) | 119.9(8) |
| C(3)—C(2)—Cl(2) | 120.3(7) |
| C(1)—C(2)—Cl(2) | 119.8(7) |
| C(2)—C(3)—C(4) | 120.8(8) |
| C(3)—C(4)—C(5) | 120.9(8) |
| C(6)—C(5)—C(4) | 117.5(8) |
| C(1)—C(6)—C(5) | 120.2(7) |
| C(1)—C(6)—C(7) | 121.2(7) |
| C(5)—C(6)—C(7) | 118.5(7) |
| N(2)—C(7)—C(8) | 121.1(7) |
| N(2)—C(7)—C(6) | 116.5(7) |
| C(8)—C(7)—C(6) | 122.4(7) |
| N(5)—C(8)—N(3) | 120.2(8) |
| N(5)—C(8)—C(7) | 119.1(8) |
| N(3)—C(8)—C(7) | 120.7(7) |
| N(4)—C(9)—N(3) | 120.9(7) |
| N(4)—C(9)—N(1) | 117.3(7) |
| N(3)—C(9)—N(1) | 121.8(7) |
| O(2)—C(10)—O(1) | 126.0(8) |
| O(2)—C(10)—C(11) | 119.6(7) |
| O(1)—C(10)—C(11) | 114.4(7) |
| O(3)—C(11)—C(11)#1 | 115.6(10) |
| O(3)—C(11)—C(10) | 101.3(7) |
| C(11)#1—C(11)—C(10) | 112.7(9) |

Symmetry transformations used to generate equivalent atoms: #1 −x + 2, −y, −z + 2

TABLE 9-4

Anisotropic displacement parameters (Å$^2$ × 10$^3$) for lamotrigine malate. The anisotropic displacement factor exponent takes the form: −2π$^2$[h$^2$ a*$^2$U$^{11}$ + ... + 2 h k a* b* U$^{12}$]

| | U$^{11}$ | U$^{22}$ | U$^{33}$ | U$^{23}$ | U$^{13}$ | U$^{12}$ |
|---|---|---|---|---|---|---|
| Cl(1) | 32(1) | 34(1) | 52(1) | 6(1) | 16(1) | −3(1) |
| Cl(2) | 38(1) | 52(2) | 55(1) | 2(1) | 25(1) | −11(1) |
| N(1) | 16(3) | 30(4) | 32(3) | −1(3) | 14(3) | −4(3) |
| N(2) | 18(3) | 34(4) | 36(4) | 1(3) | 13(3) | −4(3) |
| N(3) | 34(4) | 23(4) | 42(4) | −4(3) | 22(3) | −6(3) |
| N(4) | 31(4) | 28(4) | 39(4) | −4(3) | 20(3) | −1(3) |
| N(5) | 42(4) | 52(5) | 44(4) | −10(4) | 21(3) | −23(4) |
| C(1) | 25(4) | 37(5) | 34(4) | −3(4) | 12(3) | −3(3) |
| C(2) | 37(5) | 38(5) | 43(5) | −7(4) | 15(4) | −10(4) |
| C(3) | 28(4) | 40(6) | 81(7) | −1(5) | 24(5) | −1(4) |
| C(4) | 29(5) | 38(6) | 82(7) | 14(5) | 7(5) | 3(4) |
| C(5) | 34(5) | 32(5) | 68(6) | 9(5) | 8(4) | −5(4) |
| C(6) | 22(4) | 37(5) | 31(4) | −3(4) | 9(3) | −6(3) |
| C(7) | 22(4) | 28(5) | 37(5) | −2(4) | 12(3) | −3(3) |
| C(8) | 49(6) | 30(4) | 30(4) | −6(4) | 19(4) | −18(4) |
| C(9) | 39(5) | 15(4) | 39(5) | −1(3) | 21(4) | −3(3) |
| O(1) | 25(3) | 59(4) | 39(3) | 17(3) | 10(2) | 0(3) |
| O(2) | 31(3) | 38(4) | 75(4) | 14(3) | 36(3) | 1(3) |
| O(3) | 26(5) | 31(6) | 34(6) | 6(5) | 19(5) | −5(4) |

TABLE 9-4-continued

Anisotropic displacement parameters (Å$^2$ × 10$^3$) for lamotrigine malate. The anisotropic displacement factor exponent takes the form: $-2\pi^2[h^2 a^{*2} U^{11} + \ldots + 2 h k a^* b^* U^{12}]$

|  | U$^{11}$ | U$^{22}$ | U$^{33}$ | U$^{23}$ | U$^{13}$ | U$^{12}$ |
|---|---|---|---|---|---|---|
| C(10) | 29(4) | 44(5) | 38(5) | 7(4) | 8(4) | 4(4) |
| C(11) | 34(4) | 39(5) | 32(4) | 7(4) | 12(4) | −11(4) |

TABLE 9-5

Hydrogen coordinates (× 10$^4$) and isotropic displacement parameters (Å$^2$ × 10$^3$) for lamotrigine malate

|  | x | y | z | U(eq) |
|---|---|---|---|---|
| H(1N) | 3055 | 7226 | 6065 | 30 |
| H(2N) | 2380 | 8613 | 8375 | 37 |
| H(3N) | 1839 | 8091 | 6994 | 37 |
| H(4N) | 6778 | 9495 | 9501 | 53 |
| H(5N) | 6022 | 9738 | 9948 | 53 |
| H(3) | 9530 | 7752 | 7013 | 58 |
| H(4) | 8840 | 6105 | 8039 | 62 |
| H(5) | 7059 | 6275 | 8268 | 55 |
| H(3A) | 8217 | −851 | 10132 | 42 |
| H(11) | 9760(60) | 40(90) | 11210(80) | 42 |

Example 10

Preparation of Lamotrigine Nicotinate Methanolate 15 mg of lamotrigine was dissolved in 2 ml of methanol, 7 mg of nicotinic acid was added to the solution to form a single solution. The solution was then allowed to stand for several hours to effect the slow evaporation of solvent. The solids gathered were stored in screw cap vials for subsequent analysis.

The single crystal x-ray diffraction data for lamotrigine nicotinate methanolate is provided below. The PXRD diffractogram is shown in FIG. 20. The infrared spectrum is shown in FIG. 21.

TABLE 10-1

Crystal data and structure refinement for lamotrigine nicotinate methanolate.

| Empirical formula | C17H20Cl2N6O4 |
|---|---|
| Formula weight | 443.29 |
| Temperature | 100(2) K |
| Wavelength | 0.71073 Å |
| Crystal system | Monoclinic |
| Space group | P2(1)/c |
| Unit cell dimensions | a = 7.657(3) Å  α = 90°. |
|  | b = 15.882(6) Å  β = 90.000(8)°. |
|  | c = 16.826(7) Å  γ = 90°. |
| Volume | 2046.3(14) Å$^3$ |
| Z | 4 |
| Density (calculated) | 1.439 Mg/m$^3$ |
| Absorption coefficient | 0.354 mm$^{-1}$ |
| F(000) | 920 |
| Crystal size | 0.1 × 0.2 × 0.4 mm$^3$ |
| Theta range for data collection | 1.76 to 28.27°. |
| Index ranges | −9 <= h <= 9, −20 <= k <= 12, |
|  | −21 <= l <= 22 |
| Reflections collected | 12207 |
| Independent reflections | 4730 [R(int) = 0.1366] |
| Completeness to theta = 28.27° | 93.0% |
| Absorption correction | None |
| Refinement method | Full-matrix least-squares on F$^2$ |
| Data/restraints/parameters | 4730/0/264 |
| Goodness-of-fit on F$^2$ | 0.768 |
| Final R indices [I>2sigma(I)] | R1 = 0.0521, wR2 = 0.1090 |
| R indices (all data) | R1 = 0.0995, wR2 = 0.1182 |
| Largest diff. peak and hole | 0.485 and −0.433 e · Å$^{-3}$ |

TABLE 10-2

Atomic coordinates (× 10$^4$) and equivalent isotropic displacement parameters (Å$^2$ × 10$^3$) for lamotrigine nicotinate methanolate. U(eq) is defined as one third of the trace of the orthogonalized U$^{ij}$ tensor.

|  | x | y | z | U(eq) |
|---|---|---|---|---|
| Cl(1) | 10173(1) | 1106(1) | 693(1) | 22(1) |
| Cl(2) | 7051(1) | −168(1) | 882(1) | 31(1) |
| N(1) | 11773(3) | 3630(1) | 1290(1) | 17(1) |
| N(2) | 10507(3) | 3978(1) | 57(1) | 17(1) |
| N(3) | 9212(3) | 3407(1) | 123(1) | 16(1) |
| N(4) | 10427(3) | 2654(1) | 2056(1) | 20(1) |
| N(5) | 13057(3) | 4606(2) | 451(1) | 20(1) |
| C(1) | 8066(4) | 1468(2) | 824(2) | 18(1) |
| C(2) | 6691(4) | 908(2) | 894(2) | 20(1) |
| C(3) | 5010(4) | 1190(2) | 972(2) | 24(1) |
| C(4) | 4677(4) | 2047(2) | 982(2) | 26(1) |
| C(5) | 6037(4) | 2611(2) | 909(2) | 21(1) |
| C(6) | 7744(4) | 2336(2) | 840(2) | 16(1) |
| C(7) | 9193(4) | 2954(2) | 766(2) | 16(1) |
| C(8) | 11773(4) | 4071(2) | 606(2) | 17(1) |
| C(9) | 10482(4) | 3083(2) | 1391(2) | 16(1) |
| O(1) | 847(3) | 10297(1) | 3594(1) | 19(1) |
| O(2) | 3516(3) | 9845(1) | 3906(1) | 22(1) |
| N(6) | 4054(4) | 8543(2) | 1815(2) | 24(1) |
| C(10) | 2236(4) | 9907(2) | 3444(2) | 18(1) |
| C(11) | 2370(4) | 9450(2) | 2657(2) | 17(1) |
| C(12) | 1010(4) | 9427(2) | 2120(2) | 22(1) |
| C(13) | 1185(4) | 8956(2) | 1431(2) | 26(1) |
| C(14) | 2718(4) | 8524(2) | 1314(2) | 27(1) |
| C(15) | 3877(4) | 9011(2) | 2473(2) | 20(1) |
| O(1S) | 1434(3) | 6286(1) | 2291(1) | 28(1) |
| O(2S) | 2671(3) | 2934(2) | 3312(1) | 38(1) |
| C(1S) | 3127(5) | 6220(2) | 1975(2) | 35(1) |
| C(2S) | 2472(5) | 2350(2) | 3934(2) | 41(1) |

TABLE 10-3

Bond lengths [Å] and angles [°] for lamotrigine nicotinate methanolate.

| Cl(1)—C(1) | 1.726(3) |
|---|---|
| Cl(2)—C(2) | 1.731(3) |
| N(1)—C(9) | 1.327(4) |
| N(1)—C(8) | 1.347(3) |
| N(2)—C(8) | 1.347(4) |
| N(2)—N(3) | 1.349(3) |
| N(3)—C(7) | 1.298(3) |
| N(4)—C(9) | 1.310(3) |
| N(5)—C(8) | 1.325(4) |
| C(1)—C(2) | 1.384(4) |
| C(1)—C(6) | 1.400(4) |
| C(2)—C(3) | 1.369(4) |
| C(3)—C(4) | 1.384(4) |
| C(4)—C(5) | 1.379(4) |
| C(5)—C(6) | 1.383(4) |
| C(6)—C(7) | 1.487(4) |
| C(7)—C(9) | 1.457(4) |
| O(1)—C(10) | 1.256(3) |
| O(2)—C(10) | 1.255(4) |
| N(6)—C(14) | 1.326(4) |
| N(6)—C(15) | 1.340(3) |
| C(10)—C(11) | 1.513(4) |
| C(11)—C(12) | 1.379(4) |
| C(11)—C(15) | 1.383(4) |

TABLE 10-3-continued

Bond lengths [Å] and angles [°] for lamotrigine nicotinate methanolate.

| | |
|---|---|
| C(12)—C(13) | 1.386(4) |
| C(13)—C(14) | 1.375(4) |
| O(1S)—C(1S) | 1.406(4) |
| O(2S)—C(2S) | 1.406(3) |
| C(9)—N(1)—C(8) | 116.8(3) |
| C(8)—N(2)—N(3) | 123.0(2) |
| C(7)—N(3)—N(2) | 116.7(3) |
| C(2)—C(1)—C(6) | 119.8(3) |
| C(2)—C(1)—Cl(1) | 120.6(2) |
| C(6)—C(1)—Cl(1) | 119.6(2) |
| C(3)—C(2)—C(1) | 120.9(3) |
| C(3)—C(2)—Cl(2) | 118.3(2) |
| C(1)—C(2)—Cl(2) | 120.8(2) |
| C(2)—C(3)—C(4) | 119.8(3) |
| C(5)—C(4)—C(3) | 119.9(3) |
| C(4)—C(5)—C(6) | 121.1(3) |
| C(5)—C(6)—C(1) | 118.6(3) |
| C(5)—C(6)—C(7) | 120.2(3) |
| C(1)—C(6)—C(7) | 121.1(3) |
| N(3)—C(7)—C(9) | 121.1(3) |
| N(3)—C(7)—C(6) | 116.3(3) |
| C(9)—C(7)—C(6) | 122.5(2) |
| N(5)—C(8)—N(1) | 120.0(3) |
| N(5)—C(8)—N(2) | 118.0(3) |
| N(1)—C(8)—N(2) | 121.9(3) |
| N(4)—C(9)—N(1) | 118.3(3) |
| N(4)—C(9)—C(7) | 121.4(3) |
| N(1)—C(9)—C(7) | 120.2(3) |
| C(14)—N(6)—C(15) | 117.4(3) |
| O(2)—C(10)—O(1) | 125.2(3) |
| O(2)—C(10)—C(11) | 116.8(3) |
| O(1)—C(10)—C(11) | 118.0(3) |
| C(12)—C(11)—C(15) | 118.0(3) |
| C(12)—C(11)—C(10) | 122.3(3) |
| C(15)—C(11)—C(10) | 119.6(3) |
| C(11)—C(12)—C(13) | 119.3(3) |
| C(14)—C(13)—C(12) | 118.1(3) |
| N(6)—C(14)—C(13) | 123.8(3) |
| N(6)—C(15)—C(11) | 123.3(3) |

TABLE 10-4

Anisotropic displacement parameters ($Å^2 \times 10^3$) for lamotrigine nicotinate methanolate. The anisotropic displacement factor exponent takes the form: $-2\pi^2[h^2 a^{*2} U^{11} + \ldots + 2 h k a^* b^* U^{12}]$

| | $U^{11}$ | $U^{22}$ | $U^{33}$ | $U^{23}$ | $U^{13}$ | $U^{12}$ |
|---|---|---|---|---|---|---|
| Cl(1) | 22(1) | 15(1) | 30(1) | −1(1) | 5(1) | 3(1) |
| Cl(2) | 31(1) | 11(1) | 52(1) | 0(1) | 3(1) | 0(1) |
| N(1) | 23(2) | 12(1) | 14(1) | 1(1) | 2(1) | 2(1) |
| N(2) | 23(2) | 11(1) | 16(1) | 2(1) | 2(1) | −1(1) |
| N(3) | 22(2) | 11(1) | 16(1) | −3(1) | 4(1) | 2(1) |
| N(4) | 32(2) | 15(1) | 13(1) | 2(1) | 1(1) | −3(1) |
| N(5) | 28(2) | 19(1) | 13(1) | 4(1) | −1(1) | −5(1) |
| C(1) | 21(2) | 19(2) | 14(2) | 1(1) | 3(1) | 5(1) |
| C(2) | 27(2) | 13(2) | 19(2) | 0(1) | 3(1) | −1(1) |
| C(3) | 22(2) | 19(2) | 32(2) | 0(1) | 1(2) | −4(1) |
| C(4) | 22(2) | 21(2) | 36(2) | −3(2) | 5(2) | 2(1) |
| C(5) | 26(2) | 15(2) | 23(2) | −2(1) | 1(1) | 4(1) |
| C(6) | 22(2) | 13(2) | 13(2) | −1(1) | 2(1) | 0(1) |
| C(7) | 20(2) | 10(1) | 18(2) | −1(1) | 5(1) | 4(1) |
| C(8) | 22(2) | 11(2) | 16(2) | −3(1) | 2(1) | 6(1) |
| C(9) | 20(2) | 10(2) | 18(2) | −2(1) | 5(1) | 4(1) |
| O(1) | 24(1) | 15(1) | 17(1) | −2(1) | 3(1) | 3(1) |
| O(2) | 25(1) | 24(1) | 17(1) | −6(1) | −2(1) | 3(1) |
| N(6) | 34(2) | 19(1) | 20(1) | −3(1) | 3(1) | 4(1) |
| C(10) | 23(2) | 10(2) | 19(2) | 2(1) | 4(1) | −4(1) |
| C(11) | 24(2) | 10(2) | 16(2) | 2(1) | 4(1) | −3(1) |
| C(12) | 25(2) | 18(2) | 22(2) | −1(1) | 2(1) | 5(1) |
| C(13) | 33(2) | 25(2) | 19(2) | −5(1) | −3(2) | 4(2) |
| C(14) | 37(2) | 25(2) | 19(2) | −6(2) | −2(1) | 1(2) |
| C(15) | 29(2) | 16(2) | 14(2) | 0(1) | 2(1) | −1(1) |
| O(1S) | 30(1) | 22(1) | 31(1) | −12(1) | 6(1) | −1(1) |
| O(2S) | 40(2) | 44(2) | 29(1) | 21(1) | −9(1) | −24(1) |
| C(1S) | 40(2) | 33(2) | 32(2) | −7(2) | 4(2) | −1(2) |
| C(2S) | 60(3) | 32(2) | 29(2) | 14(2) | 8(2) | −9(2) |

TABLE 10-5

Hydrogen coordinates ($\times 10^4$) and isotropic displacement parameters ($Å^2 \times 10^3$) for lamotrigine nicotinate methanolate.

| | x | y | z | U(eq) |
|---|---|---|---|---|
| H(21) | 10516 | 4256 | −496 | 20 |
| H(41) | 11226 | 2742 | 2501 | 24 |
| H(42) | 9610 | 2238 | 2120 | 24 |
| H(51) | 13970 | 4628 | 855 | 24 |
| H(52) | 12903 | 4855 | −132 | 24 |
| H(3) | 4075 | 800 | 1017 | 29 |
| H(4) | 3514 | 2246 | 1040 | 32 |
| H(5) | 5797 | 3198 | 905 | 26 |
| H(12) | −35 | 9730 | 2222 | 26 |
| H(13) | 270 | 8933 | 1050 | 31 |
| H(14) | 2827 | 8192 | 847 | 32 |
| H(15) | 4835 | 9043 | 2831 | 23 |
| H(1S) | 806 | 5846 | 2072 | 33 |
| H(2S) | 3942 | 3148 | 3341 | 45 |
| H(1S1) | 3883 | 6645 | 2219 | 52 |
| H(1S2) | 3086 | 6310 | 1399 | 52 |
| H(1S3) | 3594 | 5657 | 2085 | 52 |
| H(2S1) | 2750 | 2622 | 4441 | 61 |
| H(2S2) | 3264 | 1873 | 3849 | 61 |
| H(2S3) | 1264 | 2147 | 3945 | 61 |

Example 11

Preparation of Lamotrigine Dimethanolate 21 mg of lamotrigine was dissolved in 2 ml of methanol, 15 mg of butylated hydroxyanisole was added to the solution to form a single solution. The solution was then allowed to stand for several hours to effect the slow evaporation of solvent. The solids gathered were stored in screw cap vials for subsequent analysis.

The single crystal x-ray diffraction data for lamotrigine dimethanolate is provided below. The PXRD diffractogram is shown in FIG. 23. The FT-IR spectrum pattern is shown in FIG. 24.

TABLE 11-1

Crystal data and structure refinement for lamotrigine dimethanolate.

| | |
|---|---|
| Empirical formula | C11H15Cl2N5O2 |
| Formula weight | 320.18 |
| Temperature | 100(2) K |
| Wavelength | 0.71073 Å |
| Crystal system | Monoclinic |
| Space group | C2/c |
| Unit cell dimensions | a = 19.430(10) Å   α = 90°. |
| | b = 17.740(9) Å   β = 97.913(10)°. |
| | c = 8.324(4) Å   γ = 90°. |
| Volume | 2842(3) Å$^3$ |
| Z | 8 |
| Density (calculated) | 1.497 Mg/m$^3$ |
| Absorption coefficient | 0.466 mm$^{-1}$ |
| F(000) | 1328 |
| Crystal size | 0.60 × 0.40 × 0.20 mm$^3$ |

TABLE 11-1-continued

Crystal data and structure refinement for lamotrigine dimethanolate.

| | |
|---|---|
| Theta range for data collection | 2.12 to 28.36°. |
| Index ranges | −25 <= h <= 17, −23 <= k <= 16, −10 <= l <= 10 |
| Reflections collected | 7952 |
| Independent reflections | 3289 [R(int) = 0.0668] |
| Completeness to theta = 28.36° | 92.6% |
| Absorption correction | None |
| Refinement method | Full-matrix least-squares on $F^2$ |
| Data/restraints/parameters | 3289/0/183 |
| Goodness-of-fit on $F^2$ | 0.781 |
| Final R indices [I > 2sigma(I)] | R1 = 0.0732, wR2 = 0.1940 |
| R indices (all data) | R1 = 0.0836, wR2 = 0.2060 |
| Largest diff. peak and hole | 1.384 and −0.803 e · Å$^{-3}$ |

TABLE 11-2

Atomic coordinates (×10$^4$) and equivalent isotropic displacement parameters (Å$^2$ × 10$^3$) for lamotrigine dimethanolate. U(eq) is defined as one third of the trace of the orthogonalized U$^{ij}$ tensor.

| | x | y | z | U(eq) |
|---|---|---|---|---|
| Cl(1) | 2324(1) | 86(1) | 463(1) | 23(1) |
| Cl(2) | 764(1) | 64(1) | −990(1) | 27(1) |
| N(1) | 3974(1) | 1568(1) | 2274(2) | 17(1) |
| N(2) | 3612(1) | 1471(1) | 4894(2) | 19(1) |
| N(3) | 2945(1) | 1413(1) | 4212(3) | 17(1) |
| N(4) | 4759(1) | 1561(1) | 4584(3) | 25(1) |
| N(5) | 3162(1) | 1646(1) | 49(1) | 20(1) |
| O(1) | 4143(1) | 1162(1) | 7948(2) | 21(1) |
| O(2) | 2173(1) | 1725(1) | 7029(2) | 28(1) |
| C(1) | 1777(1) | 793(1) | 948(3) | 18(1) |
| C(2) | 1080(1) | 769(2) | 327(3) | 20(1) |
| C(3) | 627(1) | 1319(2) | 765(3) | 23(1) |
| C(4) | 883(1) | 1885(2) | 1823(3) | 25(1) |
| C(5) | 1575(1) | 1915(2) | 2430(3) | 20(1) |
| C(6) | 2783(1) | 1433(1) | 2654(3) | 16(1) |
| C(7) | 2038(1) | 1377(1) | 1987(3) | 17(1) |
| C(8) | 3311(1) | 1548(1) | 1611(3) | 17(1) |
| C(9) | 4098(1) | 1529(1) | 3880(3) | 18(1) |
| C(10) | 1450(1) | 1603(2) | 6741(4) | 29(1) |
| C(11) | 4083(1) | 370(2) | 8183(4) | 30(1) |

TABLE 11-3

Bond lengths [Å] and angles [°] for lamotrigine dimethanolate.

| | |
|---|---|
| Cl(1)—C(1) | 1.726(2) |
| Cl(2)—C(2) | 1.720(3) |
| N(1)—C(9) | 1.327(3) |
| N(1)—C(8) | 1.331(3) |
| N(2)—N(3) | 1.344(3) |
| N(2)—C(9) | 1.355(3) |
| N(3)—C(6) | 1.292(3) |
| N(4)—C(9) | 1.336(3) |
| N(5)—C(8) | 1.304(3) |
| O(1)—C(11) | 1.426(4) |
| O(2)—C(10) | 1.410(3) |
| C(1)—C(2) | 1.383(3) |
| C(1)—C(7) | 1.399(4) |
| C(2)—C(3) | 1.394(4) |
| C(3)—C(4) | 1.381(4) |
| C(4)—C(5) | 1.371(3) |
| C(5)—C(7) | 1.396(3) |
| C(6)—C(8) | 1.447(3) |
| C(6)—C(7) | 1.479(3) |
| C(9)—N(1)—C(8) | 116.6(2) |
| N(3)—N(2)—C(9) | 117.2(2) |
| C(6)—N(3)—N(2) | 120.68(19) |
| C(2)—C(1)—C(7) | 120.4(2) |
| C(2)—C(1)—Cl(1) | 119.55(19) |
| C(7)—C(1)—Cl(1) | 120.02(18) |
| C(1)—C(2)—C(3) | 120.1(2) |
| C(1)—C(2)—Cl(2) | 120.35(19) |
| C(3)—C(2)—Cl(2) | 119.53(19) |
| C(4)—C(3)—C(2) | 119.4(2) |
| C(5)—C(4)—C(3) | 120.7(2) |
| C(4)—C(5)—C(7) | 120.8(2) |
| N(3)—C(6)—C(8) | 120.7(2) |
| N(3)—C(6)—C(7) | 117.8(2) |
| C(8)—C(6)—C(7) | 121.5(2) |
| C(5)—C(7)—C(1) | 118.5(2) |
| C(5)—C(7)—C(6) | 119.2(2) |
| C(1)—C(7)—C(6) | 122.3(2) |
| N(5)—C(8)—N(1) | 118.6(2) |
| N(5)—C(8)—C(6) | 122.6(2) |
| N(1)—C(8)—C(6) | 118.8(2) |
| N(1)—C(9)—N(4) | 118.0(2) |
| N(1)—C(9)—N(2) | 125.8(2) |
| N(4)—C(9)—N(2) | 116.1(2) |

TABLE 11-4

Anisotropic displacement parameters (Å$^2$ × 10$^3$) for lamotrigine dimethanolate. The anisotropic displacement factor exponent takes the form: $-2\pi^2[h^2 a^{*2} U^{11} + \ldots + 2 h k a^* b^* U^{12}]$

| | U$^{11}$ | U$^{22}$ | U$^{33}$ | U$^{23}$ | U$^{13}$ | U$^{12}$ |
|---|---|---|---|---|---|---|
| Cl(1) | 20(1) | 14(1) | 37(1) | −5(1) | 11(1) | 0(1) |
| Cl(2) | 24(1) | 26(1) | 32(1) | −5(1) | 4(1) | −9(1) |
| N(1) | 16(1) | 14(1) | 23(1) | 1(1) | 7(1) | −1(1) |
| N(2) | 16(1) | 17(1) | 24(1) | 2(1) | 6(1) | −1(1) |
| N(3) | 16(1) | 10(1) | 27(1) | −1(1) | 6(1) | −1(1) |
| N(4) | 16(1) | 36(2) | 24(1) | 4(1) | 2(1) | −1(1) |
| N(5) | 16(1) | 24(1) | 19(1) | 2(1) | 3(1) | −2(1) |
| O(1) | 20(1) | 18(1) | 26(1) | 3(1) | 5(1) | 0(1) |
| O(2) | 25(1) | 29(1) | 32(1) | −3(1) | 8(1) | −3(1) |
| C(1) | 17(1) | 14(1) | 25(1) | 2(1) | 10(1) | 1(1) |
| C(2) | 19(1) | 17(1) | 26(1) | 1(1) | 7(1) | −4(1) |
| C(3) | 14(1) | 23(1) | 32(1) | 5(1) | 4(1) | −1(1) |
| C(4) | 21(1) | 14(1) | 43(2) | 1(1) | 15(1) | 2(1) |
| C(5) | 21(1) | 12(1) | 29(1) | −1(1) | 11(1) | −1(1) |
| C(6) | 17(1) | 9(1) | 24(1) | 1(1) | 8(1) | 0(1) |
| C(7) | 15(1) | 13(1) | 24(1) | 4(1) | 7(1) | 1(1) |
| C(8) | 17(1) | 9(1) | 27(1) | 1(1) | 9(1) | 2(1) |
| C(9) | 16(1) | 14(1) | 25(1) | 1(1) | 5(1) | −1(1) |
| C(10) | 28(1) | 24(2) | 37(2) | 0(1) | 12(1) | −2(1) |
| C(11) | 31(2) | 22(2) | 38(2) | 2(1) | 6(1) | −1(1) |

TABLE 11-5

Hydrogen coordinates (×10$^4$) and isotropic displacement parameters (Å$^2$ × 10$^3$) for lamotrigine dimethanolate.

| | x | y | z | U(eq) |
|---|---|---|---|---|
| H(4) | 5013 | 1470 | 5395 | 30 |
| H(3) | 5103 | 1562 | 3807 | 30 |
| H(5) | 3427 | 1625 | −727 | 24 |
| H(6) | 2839 | 1668 | −662 | 24 |
| H(1O) | 3821 | 1345 | 7262 | 25 |
| H(2O) | 2408 | 1642 | 6129 | 34 |
| H(3) | 148 | 1305 | 339 | 27 |
| H(4A) | 575 | 2257 | 2133 | 30 |
| H(5A) | 1741 | 2306 | 3162 | 23 |
| H(10A) | 1233 | 1821 | 7630 | 43 |
| H(10B) | 1356 | 1060 | 6676 | 43 |
| H(10C) | 1257 | 1843 | 5716 | 43 |
| H(11A) | 4436 | 206 | 9071 | 45 |
| H(11B) | 4153 | 105 | 7185 | 45 |
| H(11C) | 3620 | 254 | 8455 | 45 |

Example 12

Preparation of Lamotrigine Ethanolate Hydrate 82 mg of lamotrigine was dissolved in 3 ml of a 1:1 ratio hot ethanol:water mix, 41 mg of nicotinamide was added to the solution to form a single solution. The solution was cooled in an ice bath and then allowed to stand at room temperature for several hours to effect the slow evaporation of solvent. The solids gathered were stored in screw cap vials for subsequent analysis.

The single crystal x-ray diffraction data for lamotrigine ethanolate hydrate is provided below. The PXRD diffractogram is shown in FIG. 26. The FT-IR spectrum pattern is shown in FIG. 27.

TABLE 12-1

Crystal data and structure refinement for lamotrigine ethanolate hydrate

| | |
|---|---|
| Empirical formula | C11H15C12N5O2 |
| Formula weight | 320.18 |
| Temperature | 100(2) K |
| Wavelength | 0.71073 Å |
| Crystal system | Monoclinic |
| Space group | P2(1)/c |
| Unit cell dimensions | a = 7.1308(14) Å  α = 90°. |
| | b = 8.3566(16) Å  β = 94.565(3)°. |
| | c = 24.018(5) Å  γ = 90°. |
| Volume | 1426.7(5) Å$^3$ |
| Z | 4 |
| Density (calculated) | 1.491 Mg/m$^3$ |
| Absorption coefficient | 0.464 mm$^{-1}$ |
| F(000) | 664 |
| Crystal size | 0.80 × 0.60 × 0.20 mm$^3$ |
| Theta range for data collection | 1.70 to 28.22°. |
| Index ranges | −9 <= h <= 9, −9 <= k <= 10, −29 <= l <= 30 |
| Reflections collected | 8317 |
| Independent reflections | 3273 [R(int) = 0.0369] |
| Completeness to theta = 28.22° | 93.1% |
| Absorption correction | None |
| Refinement method | Full-matrix least-squares on F$^2$ |
| Data/restraints/parameters | 3273/0/182 |
| Goodness-of-fit on F$^2$ | 1.026 |
| Final R indices [I > 2sigma(I)] | R1 = 0.0360, wR2 = 0.0910 |
| R indices (all data) | R1 = 0.0412, wR2 = 0.0942 |
| Largest diff. peak and hole | 0.457 and −0.292 e · Å$^{-3}$ |

TABLE 12-2

Atomic coordinates (× 10$^4$) and equivalent isotropic displacement parameters (Å$^2$ × 10$^3$) for lamotrigine ethanolate hydrate. U(eq) is defined as one third of the trace of the orthogonalized U$^{ij}$ tensor.

| | x | y | z | U(eq) |
|---|---|---|---|---|
| Cl(1) | 3636(1) | −1364(1) | 3000(1) | 20(1) |
| Cl(2) | 6781(1) | −1682(1) | 2165(1) | 24(1) |
| N(1) | 4284(2) | 2262(2) | 4086(1) | 15(1) |
| N(2) | 2968(2) | 2756(2) | 4416(1) | 15(1) |
| N(3) | 2408(2) | 26(2) | 4669(1) | 14(1) |
| N(4) | 4251(2) | −1983(2) | 4366(1) | 17(1) |
| C(1) | 6175(2) | 368(2) | 3655(1) | 14(1) |
| C(2) | 4682(2) | 731(2) | 4033(1) | 14(1) |
| N(5) | 716(2) | 2111(2) | 5004(1) | 18(1) |
| C(3) | 3766(2) | −442(2) | 4356(1) | 13(1) |
| C(4) | 8968(2) | 31(2) | 2911(1) | 20(1) |
| C(5) | 7220(2) | −660(2) | 2790(1) | 17(1) |
| C(6) | 2057(2) | 1614(2) | 4687(1) | 14(1) |
| C(7) | 7949(2) | 1042(2) | 3771(1) | 18(1) |
| C(8) | 9337(2) | 872(2) | 3404(1) | 20(1) |
| C(9) | 5825(2) | −514(2) | 3160(1) | 15(1) |
| O(1) | 3649(2) | 189(1) | 1084(1) | 21(1) |
| C(10) | 2499(2) | 278(2) | 1546(1) | 21(1) |
| C(11) | 669(3) | 1081(2) | 1355(1) | 29(1) |
| O(2) | 2421(2) | 5631(1) | 4972(1) | 18(1) |

TABLE 12-3

Bond lengths [Å] and angles [°] for lamotrigine ethanolate hydrate.

| | |
|---|---|
| Cl(1)—C(9) | 1.7306(16) |
| Cl(2)—C(5) | 1.7332(16) |
| N(1)—C(2) | 1.3190(19) |
| N(1)—N(2) | 1.3395(17) |
| N(2)—C(6) | 1.351(2) |
| N(3)—C(3) | 1.3314(19) |
| N(3)—C(6) | 1.3515(19) |
| N(4)—C(3) | 1.3326(19) |
| C(1)—C(7) | 1.392(2) |
| C(1)—C(9) | 1.404(2) |
| C(1)—C(2) | 1.484(2) |
| C(2)—C(3) | 1.439(2) |
| N(5)—C(6) | 1.335(2) |
| C(4)—C(5) | 1.384(2) |
| C(4)—C(8) | 1.385(2) |
| C(5)—C(9) | 1.390(2) |
| C(7)—C(8) | 1.383(2) |
| O(1)—C(10) | 1.4334(19) |
| C(10)—C(11) | 1.507(2) |
| C(2)—N(1)—N(2) | 121.50(13) |
| N(1)—N(2)—C(6) | 116.98(12) |
| C(3)—N(3)—C(6) | 116.81(13) |
| C(7)—C(1)—C(9) | 118.57(14) |
| C(7)—C(1)—C(2) | 118.66(13) |
| C(9)—C(1)—C(2) | 122.55(14) |
| N(1)—C(2)—C(3) | 119.87(14) |
| N(1)—C(2)—C(1) | 115.30(13) |
| C(3)—C(2)—C(1) | 124.73(13) |
| N(3)—C(3)—N(4) | 118.27(13) |
| N(3)—C(3)—C(2) | 119.11(13) |
| N(4)—C(3)—C(2) | 122.60(13) |
| C(5)—C(4)—C(8) | 119.82(15) |
| C(4)—C(5)—C(9) | 120.52(14) |
| C(4)—C(5)—Cl(2) | 118.96(12) |
| C(9)—C(5)—Cl(2) | 120.51(12) |
| N(5)—C(6)—N(2) | 116.72(13) |
| N(5)—C(6)—N(3) | 117.77(14) |
| N(2)—C(6)—N(3) | 125.51(14) |
| C(8)—C(7)—C(1) | 121.10(15) |
| C(7)—C(8)—C(4) | 119.99(15) |
| C(5)—C(9)—C(1) | 119.97(14) |
| C(5)—C(9)—Cl(1) | 120.03(12) |
| C(1)—C(9)—Cl(1) | 119.97(12) |
| O(1)—C(10)—C(11) | 108.81(13) |

TABLE 12-4

Anisotropic displacement parameters (Å$^2$ × 10$^3$) for lamotrigine ethanolate hydrate. The anisotropic displacement factor exponent takes the form: −2π$^2$[h$^2$ a*$^2$U$^{11}$ + ... + 2 h k a* b* U$^{12}$]

| | U$^{11}$ | U$^{22}$ | U$^{33}$ | U$^{23}$ | U$^{13}$ | U$^{12}$ |
|---|---|---|---|---|---|---|
| Cl(1) | 13(1) | 24(1) | 21(1) | −3(1) | −1(1) | −3(1) |
| Cl(2) | 23(1) | 31(1) | 18(1) | −7(1) | 2(1) | 5(1) |
| N(1) | 13(1) | 15(1) | 17(1) | −1(1) | 0(1) | 0(1) |
| N(2) | 16(1) | 13(1) | 18(1) | −1(1) | 2(1) | 1(1) |
| N(3) | 13(1) | 12(1) | 18(1) | 0(1) | 1(1) | −1(1) |
| N(4) | 18(1) | 12(1) | 22(1) | 2(1) | 6(1) | 2(1) |
| C(1) | 13(1) | 13(1) | 16(1) | 3(1) | 1(1) | 2(1) |
| C(2) | 13(1) | 14(1) | 15(1) | 0(1) | −1(1) | −1(1) |
| N(5) | 17(1) | 11(1) | 26(1) | −1(1) | 7(1) | −1(1) |
| C(3) | 10(1) | 15(1) | 14(1) | −2(1) | −2(1) | −1(1) |
| C(4) | 15(1) | 26(1) | 21(1) | 4(1) | 5(1) | 4(1) |
| C(5) | 17(1) | 18(1) | 15(1) | 0(1) | 1(1) | 5(1) |
| C(6) | 12(1) | 13(1) | 17(1) | −2(1) | −1(1) | −1(1) |
| C(7) | 16(1) | 19(1) | 19(1) | 0(1) | −1(1) | −1(1) |
| C(8) | 12(1) | 24(1) | 25(1) | 4(1) | 1(1) | −2(1) |
| C(9) | 11(1) | 15(1) | 19(1) | 2(1) | −1(1) | 1(1) |
| O(1) | 22(1) | 18(1) | 23(1) | 3(1) | 4(1) | 5(1) |
| C(10) | 26(1) | 17(1) | 19(1) | 0(1) | 2(1) | 0(1) |
| C(11) | 22(1) | 37(1) | 27(1) | 1(1) | 5(1) | 4(1) |
| O(2) | 21(1) | 13(1) | 21(1) | 0(1) | 2(1) | 2(1) |

TABLE 12-5

Hydrogen coordinates (× 10⁴) and isotropic displacement parameters ($Å^2 × 10^3$) for lamotrigine ethanolate hydrate.

| | x | y | z | U(eq) |
|---|---|---|---|---|
| H(3N) | 5035 | −2316 | 4130 | 20 |
| H(4N) | 3630 | −2634 | 4591 | 20 |
| H(5N) | 300 | 3075 | 5002 | 21 |
| H(6N) | −115 | 1448 | 5122 | 21 |
| H(4) | 9914 | −71 | 2655 | 24 |
| H(7) | 8210 | 1628 | 4107 | 22 |
| H(8) | 10543 | 1332 | 3491 | 24 |
| H(1O) | 4329 | −583 | 1125 | 25 |
| H(10A) | 3155 | 897 | 1854 | 25 |
| H(10B) | 2255 | −812 | 1685 | 25 |
| H(11A) | 925 | 2133 | 1198 | 43 |
| H(11B) | −95 | 1210 | 1674 | 43 |
| H(11C) | −15 | 421 | 1069 | 43 |
| H(2O) | 2750 | 4796 | 4799 | 22 |
| H(3O) | 2806 | 5390 | 5322 | 22 |

Example 13

Lamotrigine can transform into other forms of lamotrigine under certain conditions. For example, when left in aqueous suspension for a prolonged period of time, lamotrigine was found to form a new hydrate form. In a particular instance, lamotrigine was suspended in water for 12 hours at 25° C. Conversion of Lamotrigine to Lamotrigine Hydrate Form II 49 mg of lamotrigine suspended in DI water for 12 hours at 25° C. was found to form a new hydrate of lamotrigine as evidenced by X-ray diffraction. The PXRD diffractogram is shown in FIG. 29. The DSC phase transition is shown in FIG. 30.

Example 14

Rate of Dissolution Tests

Figure 31:
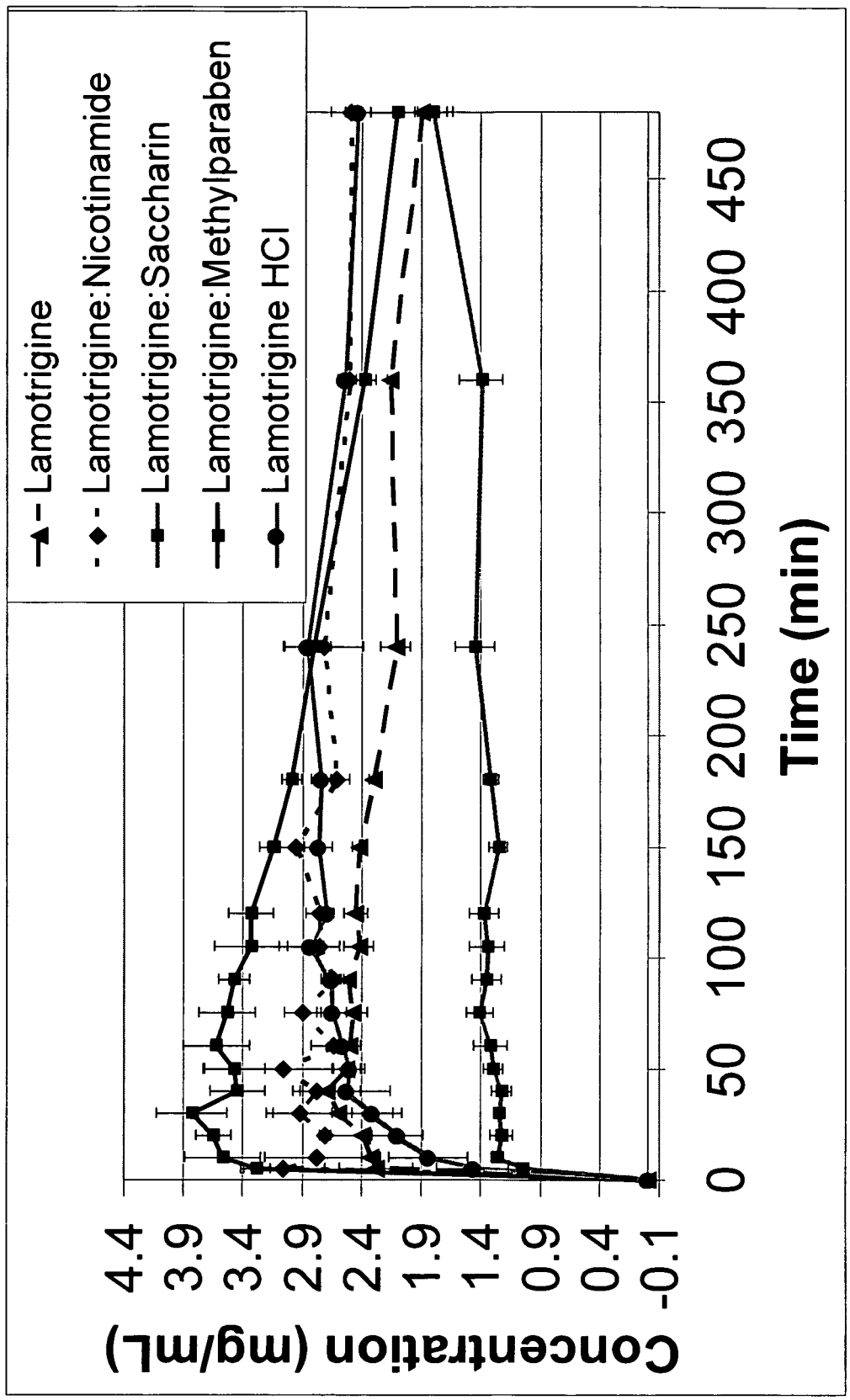
FIG. 31—Dissolution profile of lamotrigine crystalline forms at pH 1 (37° C.).
Figure 32:
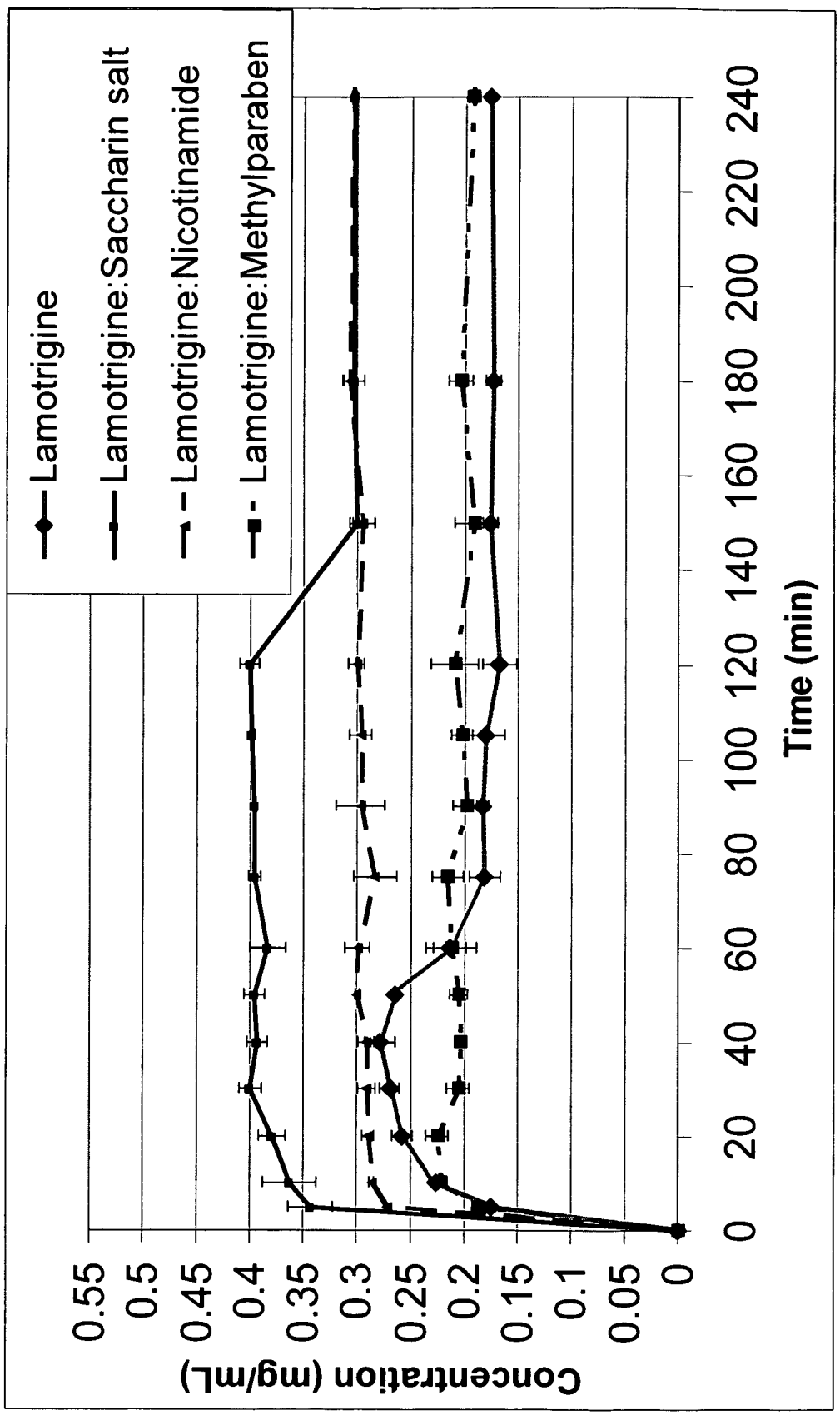
FIG. 32—Dissolution profile of lamotrigine crystalline forms in water (25° C.).

Solid lamotrigine forms were added to water, and to 0.1M HCl solution (pH 1) kept at 25° C. and 37° C. respectively. Both solutions were continuously stirred to achieve concentration homogeneity during the entire test. The solutions temperatures were kept by a heated water bath. Small volumes of solution samples were taken at set time intervals throughout the duration of the test and the lamotrigine concentration was evaluated by UV spectrometry. This procedure is well known for the person with ordinary skills in the art. The results of tests are shown in FIGS. 31 and 32.

Example 15

In-Vivo Test

Rats Sprague-Dawley, 8 weeks old weighting from 225 to 250 g, implanted with indwelling jugular vein catheter from Charles River Laboratories were purchased. Rats historically have been used in safety evaluation and PK screening studies and are recommended by appropriate regulatory agencies. The rat is established as an appropriate species for assessing the absorption of lamotrigine. The dose was 10 mg/kg of pure lamotrigine and 10 mg/kg of lamotrigine in selected lamotrigine cocrystals (dose is measured as lamotrigine, not as the cocrystal lamotrigine form).

Dose preparation: dose is prepared and suspended in 1 ml of 5% PEG 400 with 95% methylcellulose solution (weight percentage); methylcellulose solution is prepared by dissolving 0.5% methylcellulose in water (weight percentage). All lamotrigine samples are delivered by feeding needle (gavage) through oral and esophagus to stomach of the rat. 200 micro liters of blood withdrawn from the indwelling intravenous catheter at 0, 30 minutes, 1, 2, 3, 4, 8, 12 and 24 hours to provide sufficient amount of serum for analysis. 5 rats were used per pure lamotrigine as well as for selected lamotrigine co-crystals. The reason for such dosing route is that rat has been validated as an appropriate model for human oral absorption of lamotrigine.

HPLC analysis with UV detection was used to quantitatively assess lamotrigine in blood serum by the internal standard method. Analysis was performed on HPLC (Perkin Elmer Instruments LLC) comprising the following units: Series 200 Gradient Pump; 785A UV/VIS Detector; Series 200 Autosampler; NCI-900 Network Chromatography Interface and 600 Series Link. The machine was operated by Total Chrome Workstation (Perkin Elmer Instruments LLC).

Figure 33:
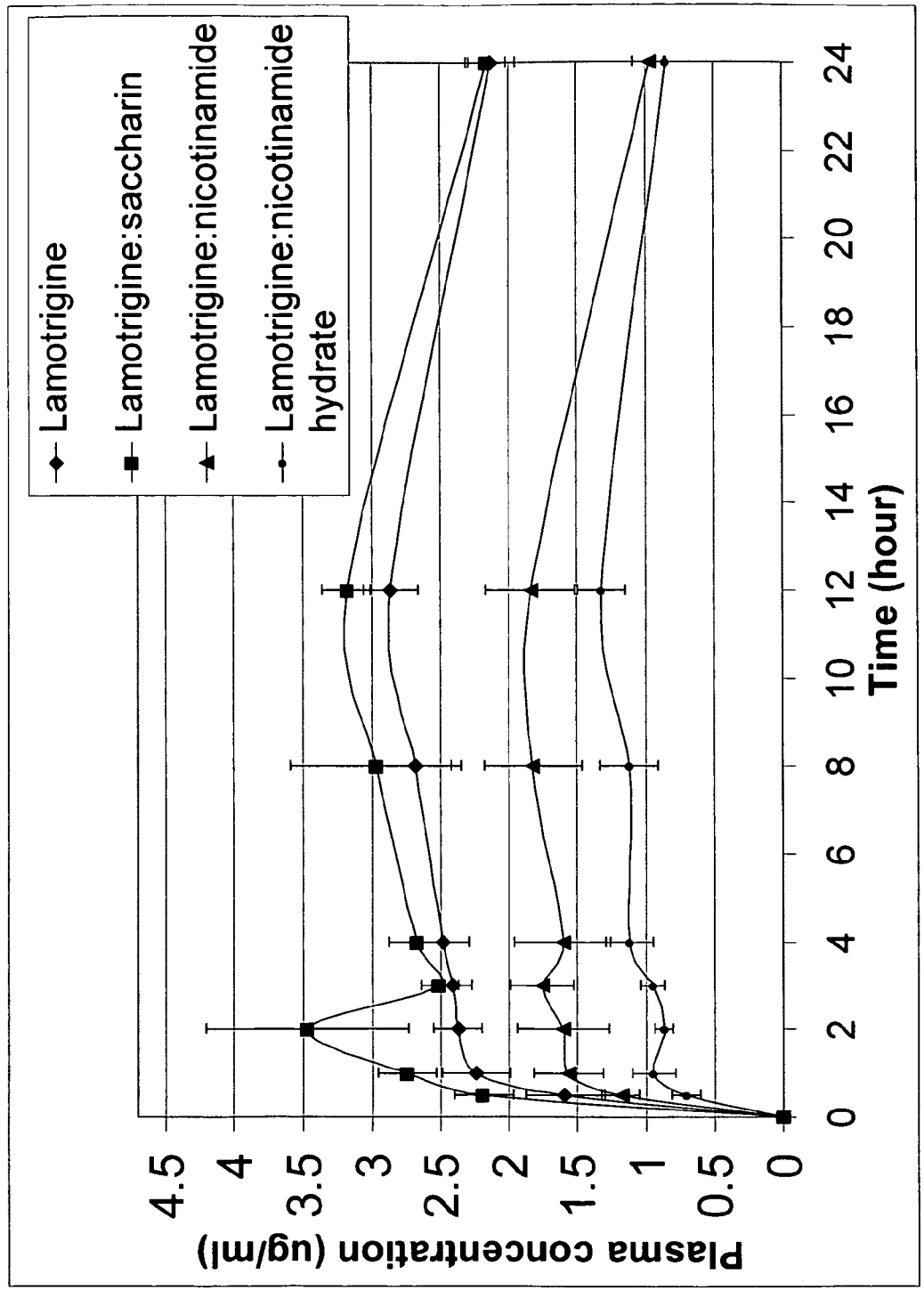
FIG. 33—Absorption profiles of selected lamotrigine cocrystals and on the market (pure) lamotrigine in rats.

This procedure is well known for the person with ordinary skills in the art. The results of tests are shown in FIG. 33 and Table 1, below.

TABLE 1

Plasma concentration of lamotrigine in rats (N = 5).

| Time (hrs) | Pure Lamotrigine (μg/ml) | Cocrystal 1 (μg/ml) | Cocrystal 2 (μg/ml) | Cocrystal 3 (μg/ml) |
|---|---|---|---|---|
| 0 | 0 | 0 | 0 | 0 |
| 0.5 | 1.5888 | 2.1874 | 1.18394 | 0.7093 |
| 1 | 2.24 | 2.74646 | 1.56064 | 0.94575 |
| 2 | 2.3744 | 3.47104 | 1.60502 | 0.869467 |
| 3 | 2.4153 | 2.50952 | 1.75738 | 0.952175 |
| 4 | 2.4796 | 2.6701 | 1.60866 | 1.12156 |
| 8 | 2.6792 | 2.96864 | 1.82258 | 1.120425 |
| 12 | 2.8617 | 3.18068 | 1.84034 | 1.31745 |
| 24 | 2.128625 | 2.15588 | 0.9718 | 0.8427 |

(Cocrystal 1 = Lamotrigine:Saccharin salt; Cocrystal 2 = Lamotrigine:Nicotinamide 1; and Cocrystal 3 = Lamotrigine:Nicotinamide 2).

This data shows that the new crystal forms of lamotrigine have an in-vivo absorption profiles that can either provide a rapid substantial increase of lamotrigine concentration in blood suitable for quick drug release or slower, steady build up of lamotrigine blood concentration suitable for drug sustained release, as compared to that of pure lamotrigine.

We claim:

1. The crystalline form of lamotrigine selected from the group consisting of co-crystals of lamotrigine and methylparaben, co-crystal of lamotrigine and nicotinamide, saccharinate salts of lamotrigine, adipate salts of lamotrigine, malate salts of lamotrigine, methanol solvates of lamotrigine nicotinate salt, dimethanol solvates, of lamotrigine, and ethanolate hydrates of lamotrigine.

2. The crystalline form of lamotrigine of claim 1, wherein said crystalline form is co-crystal lamotrigine:methylparaben form I which: a) has a PXRD diffraction pattern with peaks at about 7.19, 14.4, 16.7, 17.9, 20.75, 26.56, and 32.02+/−0.2 degrees two-theta; and/or b) has a PXRD diffraction pattern substantially as depicted in FIG. 1.

3. The crystalline form of lamotrigine of claim 1, wherein said crystalline form is co-crystal lamotrigine:methylparaben form II which: a) has a PXRD diffraction pattern with peaks at about 15.53, 18.89, 20.74, 22.0, 23.08, 23.95 and 26.89+/−0.2 degrees two-theta; b) has a PXRD diffraction pattern substantially as depicted in FIG. 3; and/or c) is characterized by a DSC thermogram with an endothermic peak at about 162.4° C.

4. The crystalline form of lamotrigine of claim 1, wherein said crystalline form is co-crystal lamotrigine:nicotinamide which: a) has a PXRD diffraction pattern with peaks at about 7.79, 14.96, 17.18, 18.98, 23.21, 26.72 and 27.47+/−0.2 degrees two-theta; b) has a PXRD diffraction pattern substantially as depicted in FIG. 7; and/or c) is characterized by a DSC thermogram with an endothermic peak at about 167.2° C.

5. The crystalline form of lamotrigine of claim 1, wherein said crystalline form is lamotrigine saccharinate which: a) has a PXRD diffraction pattern with peaks at about 5.19, 13.61, 14.96, 15.26, 24.10, 27.34 and 28.42+/−0.2 degrees two-theta; b) has a PXRD diffraction pattern substantially as depicted in FIG. 10; and/or c) is characterized by a DSC thermogram with an endothermic peak at about 262.56° C.

6. The crystalline form of lamotrigine of claim 1, wherein said crystalline form is lamotrigine adipate which: a) has a PXRD diffraction pattern with peaks at about 6.81, 18.09, 21.17, 22.81, 23.90, 25.56, and 28.20+/−0.2 degrees two-theta; and/or b) has a PXRD diffraction pattern substantially as depicted in FIG. 14.

7. The crystalline form of lamotrigine of claim 1, wherein said crystalline form is lamotrigine malate which: a) has a PXRD diffraction pattern with peaks at about 12.89, 19.49, 20.77, 21.76, 24.70, 26.44 and 29.47+/−0.2 degrees two-theta; and/or b) has a PXRD diffraction pattern substantially as depicted in FIG. 17.

8. The crystalline form of lamotrigine of claim 1, wherein said crystalline form is lamotrigine nicotinate methanolate which: a) has a PXRD diffraction pattern with peaks at about 11.54, 11.90, 16.65, 21.07, 21.85, 22.99 and 27.43+/−0.2 degrees two-theta; and/or b) has a PXRD diffraction pattern substantially as depicted in FIG. 20.

9. The crystalline form of lamotrigine of claim 1, wherein said crystalline form is lamotrigine dimethanolate which: a) has a PXRD diffraction pattern with peaks at about 9.17, 14.66, 15.65, 16.52, 19.99, 28.36 and 30.19+/−0.2 degrees two-theta; and/or b) has a PXRD diffraction pattern substantially as depicted in FIG. 23.

10. The crystalline form of lamotrigine of claim 1, wherein said crystalline form is lamotrigine ethanolate hydrate which: a) has a PXRD diffraction pattern with peaks at about 11.21, 12.44, 20.37, 24.02, 26.07, 26.47, and 27.55+/−0.2 degrees two-theta; and/or b) has a PXRD diffraction pattern substantially as depicted in FIG. 26.

11. The crystalline form of lamotrigine, wherein said crystalline form is lamotrigine hydrate form II which: a) has a PXRD diffraction pattern with peaks at about 13.28, 15.95, 20.59, 23.53, 26.65, 28.27 and 30.76+/−0.2 degrees two-theta; b) has a PXRD diffraction pattern substantially as depicted in FIG. 29.

12. A solid pharmaceutical composition comprising an effective amount of one or more of the crystalline forms of lamotrigine of claim 1 and a pharmaceutically acceptable excipient.

13. A solid pharmaceutical composition comprising an effective amount of a crystalline form of lamotrigine, wherein said crystalline form is lamotrigine hydrate form II which: a) has a PXRD diffraction pattern with peaks at t3.28, 15.95, 20.59, 23.53, 26.65, 28.27 and 30.76+/−0.2 degrees two-theta; and b) has a PXRD diffraction pattern substantially as depicted in FIG. 29.

14. The crystalline form of lamotrigine of claim 1, wherein said crystalline form of lamotrigine has one or more properties selected from the group consisting of improved solubility as compared to pure lamotrigine; an increased blood concentration as compared to pure lamotrigine; an improved absorption and pharmacokinetic (PK) profile as compared to pure lamotrigine; an increased rate of dissolution as compared to pure lamotrigine; and a sustained release profile as compared to pure lamotrigine.

* * * * *